United States Patent
Xu et al.

(10) Patent No.: US 11,883,503 B2
(45) Date of Patent: *Jan. 30, 2024

(54) METHODS AND COMPOSITIONS FOR CANCER TREATMENT

(71) Applicant: DINGFU BIOTARGET CO., LTD., Jiangsu (CN)

(72) Inventors: Ting Xu, Jiangsu (CN); Yan Luan, Jiangsu (CN); Shilong Fu, Jiangsu (CN); Songbing Qin, Jiangsu (CN); Jian Ding, Jiangsu (CN); Kai Fu, Jiangsu (CN)

(73) Assignee: DINGFU BIOTARGET CO., LTD., Jiangsu (CN)

( * ) Notice: Subject to any disclaimer, the term of this patent is extended or adjusted under 35 U.S.C. 154(b) by 450 days.

This patent is subject to a terminal disclaimer.

(21) Appl. No.: 16/649,835

(22) PCT Filed: Sep. 21, 2018

(86) PCT No.: PCT/CN2018/107101
§ 371 (c)(1),
(2) Date: Mar. 23, 2020

(87) PCT Pub. No.: WO2019/057181
PCT Pub. Date: Mar. 28, 2019

(65) Prior Publication Data
US 2020/0268902 A1   Aug. 27, 2020

(30) Foreign Application Priority Data
Sep. 25, 2017  (WO) ................ PCT/CN2017/103197

(51) Int. Cl.
*A61K 47/68* (2017.01)
*A61P 35/00* (2006.01)
*A61K 45/06* (2006.01)

(52) U.S. Cl.
CPC .......... *A61K 47/6813* (2017.08); *A61K 45/06* (2013.01); *A61P 35/00* (2018.01)

(58) Field of Classification Search
CPC ..... A61K 47/6813; A61K 45/06; A61P 35/00; C07K 14/5428
See application file for complete search history.

(56) References Cited

U.S. PATENT DOCUMENTS

| 2003/0026778 | A1 | 2/2003 | Strom et al. |
| 2017/0020963 | A1 | 1/2017 | Qu et al. |
| 2017/0368169 | A1* | 12/2017 | Loew .................. A61K 38/177 |

FOREIGN PATENT DOCUMENTS

| CN | 104220093 A | 12/2014 | |
| CN | 104540848 A | 4/2015 | |
| CN | 105198998 A | 12/2015 | |
| CN | 106061997 A | 10/2016 | |
| CN | 106883297 A | 6/2017 | |
| EP | 3093295 A1 | 11/2016 | |
| EP | 3392276 A1 | 10/2018 | |
| EP | 3093295 B1 | 5/2020 | |
| WO | 2009001219 A2 | 12/2008 | |
| WO | 2012146628 A1 | 11/2012 | |
| WO | 2014023673 A1 | 2/2014 | |
| WO | 2015103928 A1 | 7/2015 | |
| WO | WO-2015103928 A1 * | 7/2015 | ............ A61K 38/00 |
| WO | 2016082677 A1 | 6/2016 | |
| WO | 2016100788 A1 | 6/2016 | |
| WO | 2017101828 A1 | 6/2017 | |
| WO | 2018228442 A1 | 12/2018 | |

OTHER PUBLICATIONS

WO / 2015103928 Qu et al., IL-15 Heterogeneous Dimer Protein and Uses Thereof Machine Translation to English Wipo Translate [retrieved on Mar. 23, 2022]. Retrieved from the internet: <URL: https://patentscope.wipo.int/search/en/detail.jsf?docId=WO2015103928&_cid=P11-L145XG-22815-1> (Year: 2015).*
PCT/CN2018/107101 International Search Report dated Dec. 26, 2018.

* cited by examiner

*Primary Examiner* — Ruixiang Li
(74) *Attorney, Agent, or Firm* — Honigman LLP; Thomas A. Wootton, Esq.; Jonathan P. O'Brien

(57) ABSTRACT

Provided are compositions and methods for treating cancer comprising the use of a immunoconjugate in combination with a cytotoxic agent or cytotoxic therapy. The immunoconjugate in combination with a cytotoxic agent or cytotoxic therapy shows synergistic effects in cancer treatment.

5 Claims, 12 Drawing Sheets
Specification includes a Sequence Listing.

SEQUENCE LISTING

<160> NUMBER OF SEQ ID NOS: 91

<210> SEQ ID NO 1
<211> LENGTH: 227
<212> TYPE: PRT

<213> ORGANISM: Artificial Sequence
<220> FEATURE:
<223> OTHER INFORMATION: Y349C+T366W

<400> SEQUENCE: 1

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 2
<211> LENGTH: 227
<212> TYPE: PRT
<213> ORGANISM: Artificial Sequence
<220> FEATURE:
<223> OTHER INFORMATION: D356C+T366S+L368A+Y407V+F405K

<400> SEQUENCE: 2

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Cys Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 3
<211> LENGTH: 227
<212> TYPE: PRT
<213> ORGANISM: Artificial Sequence
<220> FEATURE:
<223> OTHER INFORMATION: Y349C+T366W+F405K

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 227
<212> TYPE: PRT
<213> ORGANISM: Artificial Sequence
<220> FEATURE:
<223> OTHER INFORMATION: D356C+T366S+L368A+Y407V

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Cys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 5
<211> LENGTH: 227
<212> TYPE: PRT
<213> ORGANISM: Artificial Sequence
<220> FEATURE:
<223> OTHER INFORMATION: Y349C+T366W+K409E

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

```
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Glu Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 6
<211> LENGTH: 227
<212> TYPE: PRT
<213> ORGANISM: Artificial Sequence
<220> FEATURE:
<223> OTHER INFORMATION: Y349C+T366W+K409A

<400> SEQUENCE: 6

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
            35                  40                  45

Glu Asn Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190
```

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 7
<211> LENGTH: 227
<212> TYPE: PRT
<213> ORGANISM: Artificial Sequence
<220> FEATURE:
<223> OTHER INFORMATION: Y349C+T366W+F405K+K360E+Q347E

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Cys Thr Leu Pro Pro Ser Arg Asp Glu Leu Thr Glu Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 8
<211> LENGTH: 227
<212> TYPE: PRT
<213> ORGANISM: Artificial Sequence
<220> FEATURE:
<223> OTHER INFORMATION: D356C+T366S+L368A+Y407V+Q347R

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met

```
                    20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Arg Val
        115                 120                 125

Tyr Thr Leu Pro Pro Ser Arg Cys Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 9
<211> LENGTH: 227
<212> TYPE: PRT
<213> ORGANISM: Artificial Sequence
<220> FEATURE:
<223> OTHER INFORMATION: Y349C+T366W+F405K+Q347R

<400> SEQUENCE: 9

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Arg Val
        115                 120                 125

Cys Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
```

```
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Lys Leu Tyr Ser Lys Leu Thr Val
                180                 185                 190
Asp Lys Ser Arg Trp Gln Gln Gly Asn Val Phe Ser Cys Ser Val Met
                195                 200                 205
His Glu Ala Leu His Asn His Tyr Thr Gln Lys Ser Leu Ser Leu Ser
                210                 215                 220
Pro Gly Lys
225

<210> SEQ ID NO 10
<211> LENGTH: 227
<212> TYPE: PRT
<213> ORGANISM: Artificial Sequence
<220> FEATURE:
<223> OTHER INFORMATION: D356C+T366S+L368A+Y407V+K360E+Q347E

<400> SEQUENCE: 10

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
                35                  40                  45
Glu Asp Pro Glu Val Lys Phe Asn Trp Tyr Val Asp Gly Val Glu Val
50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Glu Val
                115                 120                 125
Tyr Thr Leu Pro Pro Ser Arg Cys Glu Leu Thr Glu Asn Gln Val Ser
                130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
                180                 185                 190
Asp Lys Ser Arg Trp Gln Gln Gly Asn Val Phe Ser Cys Ser Val Met
                195                 200                 205
His Glu Ala Leu His Asn His Tyr Thr Gln Lys Ser Leu Ser Leu Ser
                210                 215                 220
Pro Gly Lys
225

<210> SEQ ID NO 11
<211> LENGTH: 227
<212> TYPE: PRT
<213> ORGANISM: Artificial Sequence
<220> FEATURE:
<223> OTHER INFORMATION: Y349C+T366W+K409A+K360E+Q347E
```

<400> SEQUENCE: 11

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Cys Thr Leu Pro Pro Ser Arg Asp Glu Leu Thr Glu Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 12
<211> LENGTH: 227
<212> TYPE: PRT
<213> ORGANISM: Artificial Sequence
<220> FEATURE:
<223> OTHER INFORMATION: D356C+T366S+L368A+Y407V+F405K+Q347R

<400> SEQUENCE: 12

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

Glu Lys Thr Ile Ser Lys Ala Lys Gly Gln Pro Arg Glu Pro Arg Val
            115                 120                 125

Tyr Thr Leu Pro Pro Ser Arg Cys Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 13
<211> LENGTH: 227
<212> TYPE: PRT
<213> ORGANISM: Artificial Sequence
<220> FEATURE:
<223> OTHER INFORMATION: Y349C+T366W+K409A+Q347R

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Arg Val
            115                 120                 125

Cys Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 14
<211> LENGTH: 227
<212> TYPE: PRT
<213> ORGANISM: Artificial Sequence
<220> FEATURE:
<223> OTHER INFORMATION: D356C+T366S+L368A+Y407V+F405K+K360E+Q347E

<400> SEQUENCE: 14

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Tyr Thr Leu Pro Pro Ser Arg Cys Glu Leu Thr Glu Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 15
<211> LENGTH: 227
<212> TYPE: PRT
<213> ORGANISM: Artificial Sequence
<220> FEATURE:
<223> OTHER INFORMATION: T366W+K409A+K392D

<400> SEQUENCE: 15

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Asp Thr Thr Pro Pro
                165                 170                 175
Val Leu Asp Ser Asp Gly Ser Phe Phe Leu Tyr Ser Ala Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 16
<211> LENGTH: 227
<212> TYPE: PRT
<213> ORGANISM: Artificial Sequence
<220> FEATURE:
<223> OTHER INFORMATION: T366S+L368A+Y407V+D399S+F405K

<400> SEQUENCE: 16

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Ser Ser Asp Gly Ser Phe Lys Leu Val Ser Lys Leu Thr Val
            180                 185                 190
Asp Lys Ser Arg Trp Gln Gln Gly Asn Val Phe Ser Cys Ser Val Met
        195                 200                 205
```

His Glu Ala Leu His Asn His Tyr Thr Gln Lys Ser Leu Ser Leu Ser
            210                 215                 220

Pro Gly Lys
225

<210> SEQ ID NO 17
<211> LENGTH: 227
<212> TYPE: PRT
<213> ORGANISM: Artificial Sequence
<220> FEATURE:
<223> OTHER INFORMATION: T366W+K409A

<400> SEQUENCE: 17

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 18
<211> LENGTH: 227
<212> TYPE: PRT
<213> ORGANISM: Artificial Sequence
<220> FEATURE:
<223> OTHER INFORMATION: T366S+L368G+Y407A+F405K

<400> SEQUENCE: 18

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His

-continued

```
                35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
130                 135                 140
Leu Ser Cys Gly Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Lys Leu Ala Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
210                 215                 220
Pro Gly Lys
225

<210> SEQ ID NO 19
<211> LENGTH: 227
<212> TYPE: PRT
<213> ORGANISM: Artificial Sequence
<220> FEATURE:
<223> OTHER INFORMATION: T366W+K409A+Y349D

<400> SEQUENCE: 19

Asp Lys Thr His Thr Cys Pro Pro Cys Pro Ala Pro Glu Leu Leu Gly
 1               5                  10                  15
Gly Pro Ser Val Phe Leu Phe Pro Pro Lys Pro Lys Asp Thr Leu Met
                 20                  25                  30
Ile Ser Arg Thr Pro Glu Val Thr Cys Val Val Val Asp Val Ser His
             35                  40                  45
Glu Asn Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Asp Thr Leu Pro Pro Ser Arg Asp Glu Leu Thr Lys Asn Gln Val Ser
130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
```

```
                165                 170                 175
Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 20
<211> LENGTH: 227
<212> TYPE: PRT
<213> ORGANISM: Artificial Sequence
<220> FEATURE:
<223> OTHER INFORMATION: T366S+L368A+Y407V+F405K+E357A

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Ala Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 21
<211> LENGTH: 227
<212> TYPE: PRT
<213> ORGANISM: Artificial Sequence
<220> FEATURE:
<223> OTHER INFORMATION: T366W+K409A+Y349D+S354D

<400> SEQUENCE: 21
```

-continued

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Asp Thr Leu Pro Pro Asp Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 22
<211> LENGTH: 227
<212> TYPE: PRT
<213> ORGANISM: Artificial Sequence
<220> FEATURE:
<223> OTHER INFORMATION: T366W+F405K

<400> SEQUENCE: 22

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

Tyr Thr Leu Pro Pro Ser Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 23
<211> LENGTH: 227
<212> TYPE: PRT
<213> ORGANISM: Artificial Sequence
<220> FEATURE:
<223> OTHER INFORMATION: T366S+L368A+Y407V+K409A

<400> SEQUENCE: 23

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Ala Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 24
<211> LENGTH: 227

```
<212> TYPE: PRT
<213> ORGANISM: Artificial Sequence
<220> FEATURE:
<223> OTHER INFORMATION: T366W+F405K+D399S

<400> SEQUENCE: 24

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Ser Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 25
<211> LENGTH: 227
<212> TYPE: PRT
<213> ORGANISM: Artificial Sequence
<220> FEATURE:
<223> OTHER INFORMATION: T366S+L368A+Y407V+K409A+K392D

<400> SEQUENCE: 25

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Asp Thr Thr Pro Pro
                165                 170                 175

Val Leu Asp Ser Asp Gly Ser Phe Phe Leu Val Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 26
<211> LENGTH: 227
<212> TYPE: PRT
<213> ORGANISM: Artificial Sequence
<220> FEATURE:
<223> OTHER INFORMATION: T366W+F405K

<400> SEQUENCE: 26

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Ser Cys Gly Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Ala Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

Pro Gly Lys
225

<210> SEQ ID NO 27
<211> LENGTH: 227
<212> TYPE: PRT
<213> ORGANISM: Artificial Sequence
<220> FEATURE:
<223> OTHER INFORMATION: T366S+L368G+Y407A+K409A

<400> SEQUENCE: 27

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Asp Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 28
<211> LENGTH: 227
<212> TYPE: PRT
<213> ORGANISM: Artificial Sequence
<220> FEATURE:
<223> OTHER INFORMATION: T366W +F405K +Y349D

<400> SEQUENCE: 28

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Ala Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 29
<211> LENGTH: 227
<212> TYPE: PRT
<213> ORGANISM: Artificial Sequence
<220> FEATURE:
<223> OTHER INFORMATION: T366S+L368A+Y407V +K409A +E357A

<400> SEQUENCE: 29

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Asp Thr Leu Pro Pro Asp Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val

```
                    180                 185                 190
Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 30
<211> LENGTH: 227
<212> TYPE: PRT
<213> ORGANISM: Artificial Sequence
<220> FEATURE:
<223> OTHER INFORMATION: wildtype human IgG1-Fc region amino acid

<400> SEQUENCE: 30

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 31
<211> LENGTH: 681
<212> TYPE: DNA
<213> ORGANISM: Artificial Sequence
<220> FEATURE:
<223> OTHER INFORMATION: Fc gene fragment

<400> SEQUENCE: 31
gacaagaccc acacctgccc cccctgcccc gccccgagc tgctgggcgg ccccagcgtg      60
ttcctgttcc cccccaagcc caaggacacc ctgatgatca gccgcacccc cgaggtgacc    120
```

```
tgcgtggtgg tggacgtgag ccacgagaac cccgaggtga agttcaactg gtacgtggac      180
ggcgtggagg tgcacaacgc caagaccaag ccccgcgagg agcagtacaa cagcacctac      240
cgcgtggtga gcgtgctgac cgtgctgcac caggactggc tgaacggcaa ggagtacaag      300
tgcaaggtga gcaacaaggc cctgcccgcc cccatcgaga agaccatcag caaggccaag      360
ggccagcccc gcgagcccca ggtgtacacc ctgcccccca gccgcgacga gctgaccaag      420
aaccaggtga gcctgacctg cctggtgaag ggcttctacc ccagcgacat cgccgtggag      480
tgggagagca acggccagcc cgagaacaac tacaagacca cccccccgt gctggacagc       540 gacggcagct tcttcctgta cagcaagctg accgtggaca agagccgctg gcagcagggc      600
aacgtgttca gctgcagcgt gatgcacgag gccctgcaca accactacac ccagaagagc      660
ctgagcctga gccccggcaa g                                                681

<210> SEQ ID NO 32
<211> LENGTH: 741
<212> TYPE: DNA
<213> ORGANISM: Artificial Sequence
<220> FEATURE:
<223> OTHER INFORMATION: polynucleotide fragment encoding a mouse
      kappaIII signal peptide

<400> SEQUENCE: 32
atggagaccg acaccctgct gctgtgggtg ctgctgctgt gggtgcccgg cagcaccggc       60
gacaagaccc acacctgccc cccctgcccc gcccccgagc tgctgggcgg cccccagcgtg     120 ttcctgttcc cccccaagcc caaggacacc ctgatgatca gccgcacccc cgaggtgacc      180
tgcgtggtgg tggacgtgag ccacgagaac cccgaggtga agttcaactg gtacgtggac      240
ggcgtggagg tgcacaacgc caagaccaag ccccgcgagg agcagtacaa cagcacctac      300
cgcgtggtga gcgtgctgac cgtgctgcac caggactggc tgaacggcaa ggagtacaag      360
tgcaaggtga gcaacaaggc cctgcccgcc cccatcgaga agaccatcag caaggccaag      420
ggccagcccc gcgagcccca ggtgtacacc ctgcccccca gccgcgacga gctgaccaag      480
aaccaggtga gcctgacctg cctggtgaag ggcttctacc ccagcgacat cgccgtggag      540
tgggagagca acggccagcc cgagaacaac tacaagacca cccccccgt gctggacagc       600 gacggcagct tcttcctgta cagcaagctg accgtggaca agagccgctg gcagcagggc      660
aacgtgttca gctgcagcgt gatgcacgag gccctgcaca accactacac ccagaagagc      720
ctgagcctga gccccggcaa g                                                741

<210> SEQ ID NO 33
<211> LENGTH: 1473
<212> TYPE: DNA
<213> ORGANISM: Artificial Sequence
<220> FEATURE:
<223> OTHER INFORMATION: gene of ScFv-Fc fusion protein

<400> SEQUENCE: 33
atggagaccg acaccctgct gctgtgggtg ctgctgctgt gggtgcccgg cagcaccggc       60
gaggtgcagc tgctggagag cggcggcggc gtggtgcagc ccggccgcag cctgcgcctg      120
agctgcatcg ccagcggctt caccttcagc agctacccca tgacctgggt cgccaggcc       180 cccggcaagg gcctggagtg ggtggccagc atcagctacg acggcagcta caagtacaag      240
gccgacagca tgaagggccg cctgaccatc agccgcgaca acagcaagaa caccctgtac      300
ctggagatga acagcctgac cgccgaggac accgccgtgt actactgcgc ccgcaccgcc      360
```

```
ttcttcaacg cctacgactt ctggggccag ggcaccctgg tgaccgtgag cagcgccagc    420
accaagggcc ccagcgtggg cggcggcggc agcggcggcg gcggcagcga gatcgtgatg    480
acccagagcc ccgccaccct gagcgtgagc cccggcgagc gcgccaccct gagctgccgc    540
gccagccaga gcgtgcgcag caacctggcc tggtaccagc agaagcccgg ccaggccccc    600
cgcctgctga tctacgccgc cagcaccccgc gccaccggca tccccgcccg cttcagcggc    660
agcggcagcg gcaccgagtt caccctgacc atcagcagcc tgcagagcga ggacttcgcc    720
gtgtactact gccagcagta caacgagtgg ttccgcacca gcggccaggg caccaaggtg    780
gagatcaagc gcgacaagac ccacacctgc ccccccctgcc ccgcccccga gctgctgggc    840
ggccccagcg tgttcctgtt cccccccaag cccaaggaca ccctgatgat cagccgcacc    900
cccgaggtga cctgcgtggt ggtggacgtg agccacgaga cccccgaggt gaagttcaac    960
tggtacgtgg acggcgtgga ggtgcacaac gccaagacca gccccgcga ggagcagtac    1020 aacagcaccT accgcgtggt gagcgtgctg accgtgctgc accaggactg gctgaacggc    1080
aaggagtaca agtgcaaggt gagcaacaag gccctgcccg cccccatcga aagaccatc    1140 agcaaggcca agggccagcc ccgcgagccc caggtgtaca ccctgccccc cagccgcgac    1200
gagctgacca agaaccaggt gagcctgacc tgcctggtga agggcttcta ccccagcgac    1260
atcgccgtgg agtgggagag caacggccag cccgagaaca actacaagac cacccccccc    1320
gtgctggaca gcgacggcag cttcttcctg tacagcaagc tgaccgtgga caagagccgc    1380
tggcagcagg gcaacgtgtt cagctgcagc gtgatgcacg aggccctgca caaccactac    1440
acccagaaga gcctgagcct gagccccggc aag                                 1473
```

<210> SEQ ID NO 34
<211> LENGTH: 471
<212> TYPE: PRT
<213> ORGANISM: Artificial Sequence
<220> FEATURE:
<223> OTHER INFORMATION: ScFv-Fc fusion protein

<400> SEQUENCE: 34

```
Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr
            20                  25                  30

Pro Met Thr Trp Val Arg Gln Ala Pro Gly Lys Gly Leu Glu Trp Val
        35                  40                  45

Ala Ser Ile Ser Tyr Asp Gly Ser Tyr Lys Tyr Lys Ala Asp Ser Met
    50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
                85                  90                  95

Ala Arg Thr Ala Phe Phe Asn Ala Tyr Asp Phe Trp Gly Gln Gly Thr
            100                 105                 110

Leu Val Thr Val Ser Ser Ala Ser Thr Lys Gly Pro Ser Val Gly Gly
        115                 120                 125

Gly Gly Ser Gly Gly Gly Ser Glu Ile Val Met Thr Gln Ser Pro
    130                 135                 140

Ala Thr Leu Ser Val Ser Pro Gly Glu Arg Ala Thr Leu Ser Cys Arg
145                 150                 155                 160
```

```
Ala Ser Gln Ser Val Arg Ser Asn Leu Ala Trp Tyr Gln Gln Lys Pro
            165                 170                 175

Gly Gln Ala Pro Arg Leu Leu Ile Tyr Ala Ala Ser Thr Arg Ala Thr
        180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asn Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 35
<211> LENGTH: 1121
<212> TYPE: DNA
<213> ORGANISM: Artificial Sequence
<220> FEATURE:
<223> OTHER INFORMATION: a fusion gene fragment encoding the fusion
      protein VhH-Fc

<400> SEQUENCE: 35
atggagaccg acaccctgct gctgtgggtg ctgctgctgt gggtgcccgg cagcaccggc        60
caggtgcagc tgcaggagtc tgggggaggc tcggtgcagg ctggagggtc tctgagactc       120
tcctgtgcag cctctgaata catctacagt agctactgca tggcctggtt ccgccaggct       180
ccagggaagg agcgcgaggg ggtcgcagtt attggagtga tggtagcaca aagctacgca       240
```

```
gactccgtga aaggccgatt caccatctcc aaagacaacg ccaagaacac tctgtatctg    300
caaatgaaca gcctgaaacc tgaggacact gccatgtact actgtgcggc catcggtggt    360
tactgctacc aaccacccta tgagtaccag tactggggcc aggggaccca ggtcaccgtc    420
tcccagaacc gaaaagcagc gacaagaccc acacctgccc ccctgccccc gcccccgagc    480
tgctgggcgg ccccagcgtg ttcctgttcc ccccaagcc caaggacacc ctgatgatca    540
gccgcacccc cgaggtgacc tgcgtggtgg tggacgtgag ccacgagaac ccgaggtga    600 agttcaactg gtacgtggac ggcgtggagg tgcacaacgc caagaccaag cccgcgagg    660 agcagtacaa cagcacctac cgcgtggtga gcgtgctgac cgtgctgcac caggactggc    720
tgaacggcaa ggagtacaag tgcaaggtga gcaacaaggc cctgccccgcc ccatcgaga    780 agaccatcag caaggccaag ggccagcccc gcgagcccca ggtgtacacc ctgccccca    840 gccgcgacga gctgaccaag aaccaggtga gcctgacctg cctggtgaag ggcttctacc    900
ccagcgacat cgccgtggag tgggagagca acggccagcc cgagaacaac tacaagacca    960 cccccccgt gctggacagc gacggcagct tcttcctgta cagcaagctg accgtggaca   1020
agagccgctg gcagcagggc aacgtgttca gctgcagcgt gatgcacgag gccctgcaca   1080
accactacac ccagaagagc ctgagcctga gccccggcaa g                      1121
```

<210> SEQ ID NO 36
<211> LENGTH: 354
<212> TYPE: PRT
<213> ORGANISM: Artificial Sequence
<220> FEATURE:
<223> OTHER INFORMATION: fusion protein VhH-Fc

<400> SEQUENCE: 36

```
Gln Val Gln Leu Gln Glu Ser Gly Gly Gly Ser Val Gln Ala Gly Gly
1               5                   10                  15

Ser Leu Arg Leu Ser Cys Ala Ala Ser Glu Tyr Ile Tyr Ser Ser Tyr
            20                  25                  30

Cys Met Ala Trp Phe Arg Gln Ala Pro Gly Lys Glu Arg Glu Gly Val
        35                  40                  45

Ala Val Ile Gly Ser Asp Gly Ser Thr Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Ile Gly Gly Tyr Cys Tyr Gln Pro Pro Tyr Glu Tyr Gln Tyr Trp
            100                 105                 110

Gly Gln Gly Thr Gln Val Thr Val Ser Ser Glu Pro Lys Ser Ser Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205
```

```
Val Val Ser Val Leu Thr Val Leu His Gln Asp Trp Leu Asn Gly Lys
    210                 215                 220
Glu Tyr Lys Cys Lys Val Ser Asn Lys Ala Leu Pro Ala Pro Ile Glu
225                 230                 235                 240
Lys Thr Ile Ser Lys Ala Lys Gly Gln Pro Arg Glu Pro Gln Val Tyr
                245                 250                 255
Thr Leu Pro Pro Ser Arg Asp Glu Leu Thr Lys Asn Gln Val Ser Leu
            260                 265                 270
Thr Cys Leu Val Lys Gly Phe Tyr Pro Ser Asp Ile Ala Val Glu Trp
        275                 280                 285
Glu Ser Asn Gly Gln Pro Glu Asn Asn Tyr Lys Thr Thr Pro Pro Val
290                 295                 300
Leu Asp Ser Asp Gly Ser Phe Phe Leu Tyr Ser Lys Leu Thr Val Asp
305                 310                 315                 320
Lys Ser Arg Trp Gln Gln Gly Asn Val Phe Ser Cys Ser Val Met His
                325                 330                 335
Glu Ala Leu His Asn His Tyr Thr Gln Lys Ser Leu Ser Leu Ser Pro
            340                 345                 350
Gly Lys

<210> SEQ ID NO 37
<211> LENGTH: 214
<212> TYPE: PRT
<213> ORGANISM: Artificial Sequence
<220> FEATURE:
<223> OTHER INFORMATION: amino acid sequence of Erb-LC

<400> SEQUENCE: 37

Asp Ile Leu Leu Thr Gln Ser Pro Val Ile Leu Ser Val Ser Pro Gly
1               5                   10                  15
Glu Arg Val Ser Phe Ser Cys Arg Ala Ser Gln Ser Ile Gly Thr Asn
                20                  25                  30
Ile His Trp Tyr Gln Gln Arg Thr Asn Gly Ser Pro Arg Leu Leu Ile
            35                  40                  45
Lys Tyr Ala Ser Glu Ser Ile Ser Gly Ile Pro Ser Arg Phe Ser Gly
50                  55                  60
Ser Gly Ser Gly Thr Asp Phe Thr Leu Ser Ile Asn Ser Val Glu Ser
65                  70                  75                  80
Glu Asp Ile Ala Asp Tyr Tyr Cys Gln Gln Asn Asn Asn Trp Pro Thr
                85                  90                  95
Thr Phe Gly Ala Gly Thr Lys Leu Glu Leu Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
```

<210> SEQ ID NO 38
<211> LENGTH: 642
<212> TYPE: DNA
<213> ORGANISM: Artificial Sequence
<220> FEATURE:
<223> OTHER INFORMATION: gene of Erb-LC

<400> SEQUENCE: 38

```
gacatcctgc tgacccagag ccccgtgatc ctgagcgtga gccccggcga gcgcgtgagc      60
ttcagctgcc gcgccagcca gagcatcggc accaacatcc actggtacca gcagcgcacc     120
aacggcagcc ccgcctgct gatcaagtac gccagcgaga gcatcagcgg catccccagc      180
cgcttcagcg gcagcggcag cggcaccgac ttcaccctga gcatcaacag cgtggagagc     240
gaggacatcg ccgactacta ctgccagcag aacaacaact ggcccaccac cttcggcgcc     300
ggcaccaagc tggagctgaa gcgcaccgtg gccgccccca gcgtgttcat cttcccccc      360
agcgacgagc agctgaagag cggcaccgcc agcgtggtgt gcctgctgaa caacttctac     420
ccccgcgagg ccaaggtgca gtggaaggtg gacaacgccc tgcagagcgg caacagccag     480
gagagcgtga ccgagcagga cagcaaggac agcacctaca gcctgagcag cacccctgacc    540
ctgagcaagg ccgactacga aagcacaag gtgtacgcct gcgaggtgac ccaccagggc      600
ctgagcagcc ccgtgaccaa gagcttcaac cgcggcgagt gc                        642
```

<210> SEQ ID NO 39
<211> LENGTH: 449
<212> TYPE: PRT
<213> ORGANISM: Artificial Sequence
<220> FEATURE:
<223> OTHER INFORMATION: amino acid sequences of Erb-Fc9

<400> SEQUENCE: 39

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Trp
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Ala Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys

<210> SEQ ID NO 40
<211> LENGTH: 1347
<212> TYPE: DNA
<213> ORGANISM: Artificial Sequence
<220> FEATURE:
<223> OTHER INFORMATION: gene of Erb-Fc9

<400> SEQUENCE: 40
caggtgcagc tgaagcagag cggccccggc ctggtgcagc ccagccagag cctgagcatc     60
acctgcaccg tgagcggctt cagcctgacc aactacggcg tgcactgggt gcgccagagc    120
cccggcaagg gcctggagtg gctgggcgtg atctggagcg gcggcaacac cgactacaac    180 accccccttca ccagccgcct gagcatcaac aaggacaaca gcaagagcca ggtgttcttc    240
aagatgaaca gcctgcagag caacgacacc gccatctact actgcgcccg cgccctgacc    300
tactacgact acgagttcgc ctactggggc cagggcaccc tggtgaccgt gagcgccgcc    360
agcactaagg ggccctctgt gtttccactc gcccccttcta gcaaaagcac ttccggagga    420
actgccgctc tgggctgtct ggtgaaagat tacttcccg aaccagtcac tgtgtcatgg    480
aactctggag cactgacatc tggagttcac acctttcctg ctgtgctgca gagttctgga    540

```
ctgtactccc tgtcatctgt ggtcaccgtg ccatcttcat ctctggggac ccagacctac    600
atctgtaacg tgaaccacaa accctccaac acaaagtgg acaaacgagt cgaaccaaaa     660
tcttgtgaca aacccacac atgcccaccg tgcccagctc cggaactcct gggcggaccg     720
tcagtcttcc tcttcccccc aaaacccaag acaccctca tgatctcccg acccctgag      780 gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccaagtcg ggatgagctg   1080
accaagaacc aggtcagcct gtggtgcctg gtcaaaggct tctatcccag cgacatcgcc   1140
gtggagtggg agagcaatgg gcagccggag aacaactaca agaccacgcc tcccgtgttg   1200
gactccgacg gctccttctt cctctacagc gcgctcaccg tggacaagag caggtggcag   1260
caggggaacg tcttctcatg ctccgtgatg catgaggctc tgcacaacca ctacacgcag   1320
aagagcctct ccctgtctcc gggtaaa                                       1347

<210> SEQ ID NO 41
<211> LENGTH: 214
<212> TYPE: PRT
<213> ORGANISM: Artificial Sequence
<220> FEATURE:
<223> OTHER INFORMATION: amino acid sequence of T-LC

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 42
<211> LENGTH: 708
<212> TYPE: DNA
<213> ORGANISM: Artificial Sequence
<220> FEATURE:
<223> OTHER INFORMATION: gene of T-LC

<400> SEQUENCE: 42

```
gacatccaga tgacccagag ccccagcagc ctgagcgcca gcgtgggcga ccgcgtgacc    60
atcacctgcc gcgccagcca ggacgtgaac accgccgtgg cctggtacca gcagaagccc   120
ggcaaggccc ccaagctgct gatctacagc gccagcttcc tgtacagcgg cgtgcccagc   180
cgcttcagcg gcagccgcag cggcaccgac ttcaccctga ccatcagcag cctgcagccc   240
gaggacttcg ccacctacta ctgccagcag cactacacca cccccccaca cttcggccag   300
ggcaccaagg tggagatcaa atactactgc cagcagaaca caactggcc accaccttc     360
ggcgccggca ccaagctgga gctgaagcgc accgtggccg cccccagcgt gttcatcttc   420
ccccccagcg acgagcagct gaagagcggc accgccagcg tggtgtgcct gctgaacaac   480
ttctacccc gcgaggccaa ggtgcagtgg aaggtggaca cgccctgca gagcggcaac    540
agccaggaga gcgtgaccga gcaggacagc aaggacagca cctacagcct gagcagcacc   600
ctgaccctga gcaaggccga ctacgagaag cacaaggtgt acgcctgcga ggtgacccac   660
cagggcctga gcagccccgt gaccaagagc ttcaaccgcg gcgagtgc                 708
```

<210> SEQ ID NO 43
<211> LENGTH: 450
<212> TYPE: PRT
<213> ORGANISM: Artificial Sequence
<220> FEATURE:
<223> OTHER INFORMATION: amino acid sequences of T-Fc9

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro

```
                    180                 185                 190
        Ser Ser Ser Leu Gly Thr Gln Thr Tyr Ile Cys Asn Val Asn His Lys
                    195                 200                 205
        Pro Ser Asn Thr Lys Val Asp Lys Arg Val Glu Pro Lys Ser Cys Asp
                    210                 215                 220
        Lys Thr His Thr Cys Pro Pro Cys Pro Ala Pro Glu Leu Leu Gly Gly
        225                 230                 235                 240
        Pro Ser Val Phe Leu Phe Pro Pro Lys Pro Lys Asp Thr Leu Met Ile
                        245                 250                 255
        Ser Arg Thr Pro Glu Val Thr Cys Val Val Val Asp Val Ser His Glu
                    260                 265                 270
        Asp Pro Glu Val Lys Phe Asn Trp Tyr Val Asp Gly Val Glu Val His
                    275                 280                 285
        Asn Ala Lys Thr Lys Pro Arg Glu Glu Gln Tyr Asn Ser Thr Tyr Arg
                    290                 295                 300
        Val Val Ser Val Leu Thr Val Leu His Gln Asp Trp Leu Asn Gly Lys
        305                 310                 315                 320
        Glu Tyr Lys Cys Lys Val Ser Asn Lys Ala Leu Pro Ala Pro Ile Glu
                        325                 330                 335
        Lys Thr Ile Ser Lys Ala Lys Gly Gln Pro Arg Glu Pro Gln Val Tyr
                    340                 345                 350
        Thr Leu Pro Pro Ser Arg Asp Glu Leu Thr Lys Asn Gln Val Ser Leu
                    355                 360                 365
        Trp Cys Leu Val Lys Gly Phe Tyr Pro Ser Asp Ile Ala Val Glu Trp
                370                 375                 380
        Glu Ser Asn Gly Gln Pro Glu Asn Asn Tyr Lys Thr Thr Pro Pro Val
        385                 390                 395                 400
        Leu Asp Ser Asp Gly Ser Phe Phe Leu Tyr Ser Ala Leu Thr Val Asp
                            405                 410                 415
        Lys Ser Arg Trp Gln Gln Gly Asn Val Phe Ser Cys Ser Val Met His
                        420                 425                 430
        Glu Ala Leu His Asn His Tyr Thr Gln Lys Ser Leu Ser Leu Ser Pro
                    435                 440                 445
        Gly Lys
            450

<210> SEQ ID NO 44
<211> LENGTH: 1350
<212> TYPE: DNA
<213> ORGANISM: Artificial Sequence
<220> FEATURE:
<223> OTHER INFORMATION: gene of T-Fc9

<400> SEQUENCE: 44
gaggtgcagc tggtggagag cggcggcggc ctggtgcagc ccggcggcag cctgcgcctg      60
agctgcgccg ccagcggctt caacatcaag gacacctaca tccactgggt gcgccaggcc    120
cccggcaagg gcctggagtg ggtggcccgc atctacccca ccaacggcta caccgcctac    180
gccgacagcg tgaagggccg cttcaccatc agcgccgaca ccagcaagaa caccgcctac    240
ctgcagatga acagcctgcg cgccgaggac accgccgtgt actactgcag ccgctggggc    300
ggcgacggct ctacgccat ggactactgg ggccagggca ccctggtgac cgtgagcagc    360
gccagcacta agggccctc tgtgtttcca ctcgcccctt ctagcaaaag cacttccgga    420
ggaactgccg ctctgggctg tctggtgaaa gattacttcc ccgaaccagt cactgtgtca    480
```

```
tggaactctg agcactgac atctggagtt cacaccttc ctgctgtgct gcagagttct    540
ggactgtact ccctgtcatc tgtggtcacc gtgccatctt catctctggg gacccagacc    600
tacatctgta acgtgaacca caaaccctcc aacacaaaag tggacaaacg agtcgaacca    660
aaatcttgtg acaaaaccca cacatgccca ccgtgcccag ctccggaact cctgggcgga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc    1020
aaagccaaag ggcagccccg agaaccacag gtgtacaccc tgcccccaag tcgggatgag    1080
ctgaccaaga accaggtcag cctgtggtgc ctggtcaaag gcttctatcc cagcgacatc    1140
gccgtggagt gggagagcaa tgggcagccg gagaacaact acaagaccac gcctcccgtg    1200
ttggactccg acggctcctt cttcctctac agcgcgctca ccgtggacaa gagcaggtgg    1260
cagcagggga acgtcttctc atgctccgtg atgcatgagg ctctgcacaa ccactacacg    1320
cagaagagcc tctccctgtc tccgggtaaa    1350
```

<210> SEQ ID NO 45
<211> LENGTH: 215
<212> TYPE: PRT
<213> ORGANISM: Artificial Sequence
<220> FEATURE:
<223> OTHER INFORMATION: amino acid sequence of 28H1-LC

<400> SEQUENCE: 45

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

Ser Phe Asn Arg Gly Glu Cys
    210                 215

<210> SEQ ID NO 46
<211> LENGTH: 645
<212> TYPE: DNA
<213> ORGANISM: Artificial Sequence
<220> FEATURE:
<223> OTHER INFORMATION: gene of 28H1-LC

<400> SEQUENCE: 46

```
gagatcgtgc tgacacagtc tccaggcacc ctgtctctgt ctccaggaga gagagccacc    60
ctgtcttgca gagcctctca gagcgtgtcc aggagctacc tggcttggta tcagcagaaa   120
ccaggacagg cccctagact gctgatcatc ggagcctcta caagagccac aggcatccca   180
gacagattca gcggcagcgg aagcggcaca gacttcaccc tgaccatcag caggctggag   240
ccagaggact cgccgtgta ctattgccag cagggccagg tcatccctcc tacctttgga   300
cagggcacca aggtggagat caagcgtacg gtggctgcac catctgtctt catcttcccg   360
ccatctgatg agcagttgaa atctggtacc gctagcgttg tgtgcctgct gaataacttt   420
tatccacggg aggctaaggt gcagtggaaa gtggacaatg ccctccagag cggaaatagc   480
caagagtccg ttaccgaaca ggactctaaa gactctacat actccctgtc ctccacactg   540
accctctcca aggccgacta tgagaaacac aaggtttacg catgcgaggt cacacaccag   600
ggactctcct ctcccgtgac caagagcttc aaccggggag aatgc                   645
```

<210> SEQ ID NO 47
<211> LENGTH: 446
<212> TYPE: PRT
<213> ORGANISM: Artificial Sequence
<220> FEATURE:
<223> OTHER INFORMATION: amino acid sequences of 28H1-Fc9

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Gln Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu

```
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
    210                 215                 220
Cys Pro Pro Cys Pro Ala Pro Glu Leu Leu Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Trp Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Ala Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 48
<211> LENGTH: 1338
<212> TYPE: DNA
<213> ORGANISM: Artificial Sequence
<220> FEATURE:
<223> OTHER INFORMATION: gene of 28H1-Fc9

<400> SEQUENCE: 48
gaggtgcagc tgctggaatc aggaggagga ctggtgcagc caggaggatc tctgagactg      60
tcttgcgccg ccagcggctt acattcagc tctcacgcca tgtcttgggt ccgacaggct     120
ccaggcaaag gactggaatg ggtgtccgct atttgggcca gcggagagca gtactacgcc     180
gacagcgtga agggacggtt caccatcagc cgggacaaca gcaagaacac cctgtacctg     240
cagatgaaca gcctgagggc ccaggatacc gccgtgtact attgcgccaa gggttggctg     300
ggcaacttcg actattgggg ccagggaacc ctggtgacag tgtccagcgc cagcactaag     360
ggcccctctg tgtttccact cgccccttct agcaaaagca cttccggagg aactgccgct     420
ctgggctgtc tggtgaaaga ttacttcccc gaaccagtca ctgtgtcatg gaactctgga     480
gcactggaca tctggagttca caccttcct gctgtgctgc agagttctgg actgtactcc     540
ctgtcatctg tggtcaccgt gccatcttca tctctgggga cccagaccta catctgtaac     600
```

-continued

```
gtgaaccaca aaccctccaa cacaaaagtg gacaaacgag tcgaaccaaa atcttgtgac      660
aaaacccaca catgcccacc gtgcccagct ccggaactcc tgggcggacc gtcagtcttc      720
ctcttccccc caaaacccaa ggacaccctc atgatctccc ggacccctga ggtcacatgc      780
gtggtggtgg acgtgagcca cgaagaccct gaggtcaagt tcaactggta cgtggacggc      840
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cccagccccc atcgagaaaa ccatctccaa agccaaaggg     1020
cagccccgag aaccacaggt gtacaccctg cccccaagtc gggatgagct gaccaagaac     1080
caggtcagcc tgtggtgcct ggtcaaaggc ttctatccca gcgacatcgc cgtggagtgg     1140
gagagcaatg ggcagccgga gaacaactac aagaccacgc ctcccgtgtt ggactccgac     1200
ggctccttct tcctctacag cgcgctcacc gtggacaaga gcaggtggca gcaggggaac     1260
gtcttctcat gctccgtgat gcatgaggct ctgcacaacc actacacgca gaagagcctc     1320
tccctgtctc cgggtaaa                                                  1338
```

<210> SEQ ID NO 49
<211> LENGTH: 15
<212> TYPE: PRT
<213> ORGANISM: Artificial Sequence
<220> FEATURE:
<223> OTHER INFORMATION: linker 1

<400> SEQUENCE: 49

Gly Gly Gly Gly Ser Gly Gly Gly Gly Ser Gly Gly Gly Gly Ser
1               5                   10                  15

<210> SEQ ID NO 50
<211> LENGTH: 582
<212> TYPE: PRT
<213> ORGANISM: Artificial Sequence
<220> FEATURE:
<223> OTHER INFORMATION: amino acid sequence of (IL10)2-Fc6

<400> SEQUENCE: 50

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

```
Gly Gly Gly Gly Ser Gly Gly Gly Ser Gly Gly Gly Ser Ser
            165             170             175

Pro Gly Gln Gly Thr Gln Ser Glu Asn Ser Cys Thr His Phe Pro Gly
            180             185             190

Asn Leu Pro Asn Met Leu Arg Asp Leu Arg Asp Ala Phe Ser Arg Val
            195             200             205

Lys Thr Phe Phe Gln Met Lys Asp Gln Leu Asp Asn Leu Leu Leu Lys
            210             215             220

Glu Ser Leu Leu Glu Asp Phe Lys Gly Tyr Leu Gly Cys Gln Ala Leu
225             230             235             240

Ser Glu Met Ile Gln Phe Tyr Leu Glu Glu Val Met Pro Gln Ala Glu
            245             250             255

Asn Gln Asp Pro Asp Ile Lys Ala His Val Asn Ser Leu Gly Glu Asn
            260             265             270

Leu Lys Thr Leu Arg Leu Arg Leu Arg Arg Cys His Arg Phe Leu Pro
            275             280             285

Cys Glu Asn Lys Ser Lys Ala Val Glu Gln Val Lys Asn Ala Phe Asn
            290             295             300

Lys Leu Gln Glu Lys Gly Ile Tyr Lys Ala Met Ser Glu Phe Asp Ile
305             310             315             320

Phe Ile Asn Tyr Ile Glu Ala Tyr Met Thr Met Lys Ile Arg Asn Gly
            325             330             335

Gly Gly Gly Ser Gly Gly Gly Gly Ser Gly Gly Gly Gly Ser Glu Pro
            340             345             350

Lys Ser Ser Asp Lys Thr His Thr Cys Pro Pro Cys Pro Ala Pro Glu
            355             360             365

Leu Leu Gly Gly Pro Ser Val Phe Leu Phe Pro Pro Lys Pro Lys Asp
            370             375             380

Thr Leu Met Ile Ser Arg Thr Pro Glu Val Thr Cys Val Val Val Asp
385             390             395             400

Val Ser His Glu Asp Pro Glu Val Lys Phe Asn Trp Tyr Val Asp Gly
            405             410             415

Val Glu Val His Asn Ala Lys Thr Lys Pro Arg Glu Glu Gln Tyr Asn
            420             425             430

Ser Thr Tyr Arg Val Val Ser Val Leu Thr Val Leu His Gln Asp Trp
            435             440             445

Leu Asn Gly Lys Glu Tyr Lys Cys Lys Val Ser Asn Lys Ala Leu Pro
450             455             460

Ala Pro Ile Glu Lys Thr Ile Ser Lys Ala Lys Gly Gln Pro Arg Glu
465             470             475             480

Pro Gln Val Tyr Thr Leu Pro Pro Ser Arg Asp Glu Leu Thr Lys Asn
            485             490             495

Gln Val Ser Leu Ser Cys Gly Val Lys Gly Phe Tyr Pro Ser Asp Ile
            500             505             510

Ala Val Glu Trp Glu Ser Asn Gly Gln Pro Glu Asn Asn Tyr Lys Thr
            515             520             525

Thr Pro Pro Val Leu Asp Ser Asp Gly Ser Phe Lys Leu Ala Ser Lys
            530             535             540

Leu Thr Val Asp Lys Ser Arg Trp Gln Gln Gly Asn Val Phe Ser Cys
545             550             555             560

Ser Val Met His Glu Ala Leu His Asn His Tyr Thr Gln Lys Ser Leu
            565             570             575
```

Ser Leu Ser Pro Gly Lys
            580

<210> SEQ ID NO 51
<211> LENGTH: 1746
<212> TYPE: DNA
<213> ORGANISM: Artificial Sequence
<220> FEATURE:
<223> OTHER INFORMATION: gene of (IL10)2-Fc6

<400> SEQUENCE: 51

| | | | | | |
|---|---|---|---|---|---|
| agccccggcc | agggcacaca | gtccgagaac | agctgcaccc | actttcccgg | caacctgcct | 60 |
| aacatgctga | gggacctgag | ggacgccttc | agcagggtga | agaccttctt | ccagatgaag | 120 |
| gaccagctgg | ataacctgct | gctgaaggag | agcctgctgg | aggacttcaa | gggctacctg | 180 |
| ggctgccagg | ccctgagcga | gatgatccag | ttctacctgg | aggaggtgat | gccccaggcc | 240 |
| gagaaccagg | accccgacat | caaggcccac | gtgaacagcc | tgggcgagaa | cctgaagacc | 300 |
| ctgaggctga | ggctgaggag | gtgccacagg | ttcctgccct | gtgagaacaa | atccaaggcc | 360 |
| gtggagcagg | tgaagaacgc | cttcaacaag | ctgcaggaaa | agggcatcta | caaggccatg | 420 |
| agcgagttcg | acatctttat | caactatatc | gaggcctaca | tgacaatgaa | gatcaggaac | 480 |
| ggcggcggcg | gcagcggggg | cggcggcagc | ggaggaggcg | gcagcagccc | cggccagggc | 540 |
| acacagtccg | agaacagctg | cacccacttt | cccggcaacc | tgcctaacat | gctgagggac | 600 |
| ctgagggacg | ccttcagcag | ggtgaagacc | ttcttccaga | tgaaggacca | gctggataac | 660 |
| ctgctgctga | aggagagcct | gctggaggac | ttcaagggct | acctgggctg | ccaggccctg | 720 |
| agcgagatga | tccagttcta | cctggaggag | gtgatgcccc | aggccgagaa | ccaggacccc | 780 |
| gacatcaagg | cccacgtgaa | cagcctgggc | gagaacctga | agaccctgag | gctgaggctg | 840 |
| aggaggtgcc | acaggttcct | gccctgtgag | aacaaatcca | aggccgtgga | gcaggtgaag | 900 |
| aacgccttca | caagctgca | ggaaaagggc | atctacaagg | ccatgagcga | gttcgacatc | 960 |
| tttatcaact | atatcgaggc | ctacatgaca | atgaagatca | ggaacggcgg | cggcggcagc | 1020 |
| ggggcggcg | gcagcggagg | aggcggcagc | gagcctaagt | ccagcgacaa | gacccacacc | 1080 |
| tgccccccctt | gccccgctcc | ggaactcctg | ggcggaccgt | cagtcttcct | cttccccca | 1140 |
| aaacccaagg | acaccctcat | gatctcccgg | acccctgagg | tcacatgcgt | ggtggtggac | 1200 |
| gtgagccacg | aagaccctga | ggtcaagttc | aactggtacg | tggacggcgt | ggaggtgcat | 1260 |
| aatgccaaga | caaagccgcg | ggaggagcag | tacaacagca | cgtaccgtgt | ggtcagcgtc | 1320 |
| ctcaccgtcc | tgcaccagga | ctggctgaat | ggcaaggagt | acaagtgcaa | ggtctccaac | 1380 |
| aaagccctcc | cagcccccat | cgagaaaacc | atctccaaag | ccaaagggca | gccccgagaa | 1440 |
| ccacaggtgt | ataccctgcc | cccatcccgg | gatgagctga | ccaagaacca | ggtcagcctg | 1500 |
| agttgcgggg | tcaaaggctt | ctatcccagc | gacatcgccg | tggagtggga | gagcaatggg | 1560 |
| cagccggaga | acaactacaa | gaccacgcct | cccgtgttgg | actccgacgg | ctccttcaag | 1620 |
| ctcgccagca | agctcaccgt | ggacaagagc | aggtggcagc | aggggaacgt | cttctcatgc | 1680 |
| tccgtgatgc | atgaggctct | gcacaaccac | tacacgcaga | agagcctctc | cctgtctccg | 1740 |
| ggtaaa | | | | | 1746 |

<210> SEQ ID NO 52
<211> LENGTH: 407
<212> TYPE: PRT
<213> ORGANISM: Artificial Sequence
<220> FEATURE:

<223> OTHER INFORMATION: amino acid sequence of IL10-Fc

<400> SEQUENCE: 52

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Ser Gly Gly Gly Ser Glu
                165                 170                 175

Pro Lys Ser Ser Asp Lys Thr His Thr Cys Pro Pro Cys Pro Ala Pro
            180                 185                 190

Glu Leu Leu Gly Gly Pro Ser Val Phe Leu Phe Pro Pro Lys Pro Lys
        195                 200                 205

Asp Thr Leu Met Ile Ser Arg Thr Pro Glu Val Thr Cys Val Val Val
    210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
                245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Lys Val Ser Asn Lys Ala Leu
        275                 280                 285

Pro Ala Pro Ile Glu Lys Thr Ile Ser Lys Ala Lys Gly Gln Pro Arg
    290                 295                 300

Glu Pro Gln Val Tyr Thr Leu Pro Pro Ser Arg Asp Glu Leu Thr Lys
305                 310                 315                 320

Asn Gln Val Ser Leu Thr Cys Leu Val Lys Gly Phe Tyr Pro Ser Asp
                325                 330                 335

Ile Ala Val Glu Trp Glu Ser Asn Gly Gln Pro Glu Asn Asn Tyr Lys
            340                 345                 350

Thr Thr Pro Pro Val Leu Asp Ser Asp Gly Ser Phe Phe Leu Tyr Ser
        355                 360                 365

Lys Leu Thr Val Asp Lys Ser Arg Trp Gln Gln Gly Asn Val Phe Ser
    370                 375                 380

Cys Ser Val Met His Glu Ala Leu His Asn His Tyr Thr Gln Lys Ser
385                 390                 395                 400
```

Leu Ser Leu Ser Pro Gly Lys
            405

<210> SEQ ID NO 53
<211> LENGTH: 1221
<212> TYPE: DNA
<213> ORGANISM: Artificial Sequence
<220> FEATURE:
<223> OTHER INFORMATION: gene of IL10-Fc

<400> SEQUENCE: 53

| | | | | | |
|---|---|---|---|---|---|
| agccccggcc | agggcacaca | gtccgagaac | agctgcaccc | actttccgg | caacctgcct | 60 |
| aacatgctga | gggacctgag | ggacgccttc | agcagggtga | agaccttctt | ccagatgaag | 120 |
| gaccagctgg | ataacctgct | gctgaaggag | agcctgctgg | aggacttcaa | gggctacctg | 180 |
| ggctgccagg | ccctgagcga | gatgatccag | ttctacctgg | aggaggtgat | gccccaggcc | 240 |
| gagaaccagg | accccgacat | caaggcccac | gtgaacagcc | tgggcgagaa | cctgaagacc | 300 |
| ctgaggctga | ggctgaggag | gtgccacagg | ttcctgccct | gtgagaacaa | atccaaggcc | 360 |
| gtggagcagg | tgaagaacgc | cttcaacaag | ctgcaggaaa | agggcatcta | caaggccatg | 420 |
| agcgagttcg | acatctttat | caactatatc | gaggcctaca | tgacaatgaa | gatcaggaac | 480 |
| ggcggcggcg | gcagcggggg | cggcggcagc | ggaggaggcg | gcagcgagcc | taagtccagc | 540 |
| gacaagaccc | acacctgccc | cccttgcccc | gctccggaac | tcctgggcgg | accgtcagtc | 600 |
| ttcctcttcc | ccccaaaacc | caaggacacc | ctcatgatct | cccggacccc | tgaggtcaca | 660 |
| tgcgtggtgg | tggacgtgag | ccacgaagac | cctgaggtca | agttcaactg | gtacgtggac | 720 |
| ggcgtggagg | tgcataatgc | caagacaaag | ccgcgggagg | agcagtacaa | cagcacgtac | 780 |
| cgtgtggtca | gcgtcctcac | cgtcctgcac | caggactggc | tgaatggcaa | ggagtacaag | 840 |
| tgcaaggtct | ccaacaaagc | cctcccagcc | cccatcgaga | aaaccatctc | caaagccaaa | 900 |
| gggcagcccc | gagaaccaca | ggtgtacacc | ctgcccccat | cccgggatga | gctgaccaag | 960 |
| aaccaggtca | gcctgacctg | cctggtcaaa | ggcttctatc | cagcgacat | cgccgtggag | 1020 |
| tgggagagca | atgggcagcc | ggagaacaac | tacaagacca | cgcctcccgt | gttggactcc | 1080 |
| gacggctcct | tcttcctcta | cagcaagctc | accgtggaca | agagcaggtg | gcagcagggg | 1140 |
| aacgtcttct | catgctccgt | gatgcatgag | gctctgcaca | accactacac | gcagaagagc | 1200 |
| ctctccctgt | ctccgggtaa | a | | | | 1221 |

<210> SEQ ID NO 54
<211> LENGTH: 681
<212> TYPE: DNA
<213> ORGANISM: Artificial Sequence
<220> FEATURE:
<223> OTHER INFORMATION: gene of Fc9

<400> SEQUENCE: 54

| | | | | | |
|---|---|---|---|---|---|
| gacaaaactc | acacatgccc | accgtgccca | gctccggaac | tcctgggcgg | accgtcagtc | 60 |
| ttcctcttcc | ccccaaaacc | caaggacacc | ctcatgatct | cccggacccc | tgaggtcaca | 120 |
| tgcgtggtgg | tggacgtgag | ccacgaagac | cctgaggtca | agttcaactg | gtacgtggac | 180 |
| ggcgtggagg | tgcataatgc | caagacaaag | ccgcgggagg | agcagtacaa | cagcacgtac | 240 |
| cgtgtggtca | gcgtcctcac | cgtcctgcac | caggactggc | tgaatggcaa | ggagtacaag | 300 |
| tgcaaggtct | ccaacaaagc | cctcccagcc | cccatcgaga | aaaccatctc | caaagccaaa | 360 |
| gggcagcccc | gagaaccaca | ggtgtacacc | ctgcccccaa | gtcgggatga | gctgaccaag | 420 |

```
aaccaggtca gcctgtggtg cctggtcaaa ggcttctatc ccagcgacat cgccgtggag    480
tgggagagca atgggcagcc ggagaacaac tacaagacca cgcctcccgt gttggactcc    540
gacggctcct tcttcctcta cagcgcgctc accgtggaca agagcaggtg gcagcagggg    600
aacgtcttct catgctccgt gatgcatgag gctctgcaca accactacac gcagaagagc    660
ctctccctgt ctccgggtaa a                                              681
```

<210> SEQ ID NO 55
<211> LENGTH: 8
<212> TYPE: PRT
<213> ORGANISM: Artificial Sequence
<220> FEATURE:
<223> OTHER INFORMATION: Kb-binding peptide antigen

<400> SEQUENCE: 55

```
Ser Ile Tyr Arg Tyr Tyr Gly Leu
1               5
```

<210> SEQ ID NO 56
<211> LENGTH: 11
<212> TYPE: PRT
<213> ORGANISM: Artificial Sequence
<220> FEATURE:
<223> OTHER INFORMATION: Cetuximab light chain CDR1

<400> SEQUENCE: 56

```
Arg Ala Ser Gln Ser Ile Gly Thr Asn Ile His
1               5                   10
```

<210> SEQ ID NO 57
<211> LENGTH: 7
<212> TYPE: PRT
<213> ORGANISM: Artificial Sequence
<220> FEATURE:
<223> OTHER INFORMATION: Cetuximab light chain CDR2

<400> SEQUENCE: 57

```
Tyr Ala Ser Glu Ser Ile Ser
1               5
```

<210> SEQ ID NO 58
<211> LENGTH: 9
<212> TYPE: PRT
<213> ORGANISM: Artificial Sequence
<220> FEATURE:
<223> OTHER INFORMATION: Cetuximab light chain CDR3

<400> SEQUENCE: 58

```
Gln Gln Asn Asn Asn Trp Pro Thr Thr
1               5
```

<210> SEQ ID NO 59
<211> LENGTH: 107
<212> TYPE: PRT
<213> ORGANISM: Artificial Sequence
<220> FEATURE:
<223> OTHER INFORMATION: Cetuximab light chain variable region

<400> SEQUENCE: 59

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
```

35                  40                  45
Lys Tyr Ala Ser Glu Ser Ile Ser Gly Ile Pro Ser Arg Phe Ser Gly
         50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys
            100                 105

<210> SEQ ID NO 60
<211> LENGTH: 5
<212> TYPE: PRT
<213> ORGANISM: Artificial Sequence
<220> FEATURE:
<223> OTHER INFORMATION: Cetuximab heavy chain CDR1

<400> SEQUENCE: 60

Asn Tyr Gly Val His
1               5

<210> SEQ ID NO 61
<211> LENGTH: 16
<212> TYPE: PRT
<213> ORGANISM: Artificial Sequence
<220> FEATURE:
<223> OTHER INFORMATION: Cetuximab heavy chain CDR2

<400> SEQUENCE: 61

Val Ile Trp Ser Gly Gly Asn Thr Asp Tyr Asn Thr Pro Phe Thr Ser
1               5                   10                  15

<210> SEQ ID NO 62
<211> LENGTH: 11
<212> TYPE: PRT
<213> ORGANISM: Artificial Sequence
<220> FEATURE:
<223> OTHER INFORMATION: Cetuximab heavy chain CDR3

<400> SEQUENCE: 62

Ala Leu Thr Tyr Tyr Asp Tyr Glu Phe Ala Tyr
1               5                   10

<210> SEQ ID NO 63
<211> LENGTH: 119
<212> TYPE: PRT
<213> ORGANISM: Artificial Sequence
<220> FEATURE:
<223> OTHER INFORMATION: Cetuximab heavy chain variable region

<400> SEQUENCE: 63

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
         50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala

```
                    85                  90                  95

Arg Ala Leu Thr Tyr Tyr Asp Tyr Glu Phe Ala Tyr Trp Gly Gln Gly
                100                 105                 110

Thr Leu Val Thr Val Ser Ala
        115

<210> SEQ ID NO 64
<211> LENGTH: 11
<212> TYPE: PRT
<213> ORGANISM: Artificial Sequence
<220> FEATURE:
<223> OTHER INFORMATION: Trastuzumab light chain CDR1

<400> SEQUENCE: 64

Arg Ala Ser Gln Asp Val Asn Thr Ala Val Ala
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Trastuzumab light chain CDR2

<400> SEQUENCE: 65

Ser Ala Ser Phe Leu Tyr Ser
1               5

<210> SEQ ID NO 66
<211> LENGTH: 9
<212> TYPE: PRT
<213> ORGANISM: Artificial Sequence
<220> FEATURE:
<223> OTHER INFORMATION: Trastuzumab light chain CDR3

<400> SEQUENCE: 66

Gln Gln His Tyr Thr Thr Pro Pro Thr
1               5

<210> SEQ ID NO 67
<211> LENGTH: 107
<212> TYPE: PRT
<213> ORGANISM: Artificial Sequence
<220> FEATURE:
<223> OTHER INFORMATION: Trastuzumab light chain variable region

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

```
<210> SEQ ID NO 68
<211> LENGTH: 5
<212> TYPE: PRT
<213> ORGANISM: Artificial Sequence
<220> FEATURE:
<223> OTHER INFORMATION: Trastuzumab heavy chain CDR1

<400> SEQUENCE: 68

Asp Thr Tyr Ile His
1               5

<210> SEQ ID NO 69
<211> LENGTH: 17
<212> TYPE: PRT
<213> ORGANISM: Artificial Sequence
<220> FEATURE:
<223> OTHER INFORMATION: Trastuzumab heavy chain CDR2

<400> SEQUENCE: 69

Arg Ile Tyr Pro Thr Asn Gly Tyr Thr Arg Tyr Ala Asp Ser Val Lys
1               5                   10                  15

Gly

<210> SEQ ID NO 70
<211> LENGTH: 11
<212> TYPE: PRT
<213> ORGANISM: Artificial Sequence
<220> FEATURE:
<223> OTHER INFORMATION: Trastuzumab heavy chain CDR3

<400> SEQUENCE: 70

Trp Gly Gly Asp Gly Phe Tyr Ala Met Asp Tyr
1               5                   10

<210> SEQ ID NO 71
<211> LENGTH: 120
<212> TYPE: PRT
<213> ORGANISM: Artificial Sequence
<220> FEATURE:
<223> OTHER INFORMATION: Trastuzumab heavy chain variable region

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 72
<211> LENGTH: 6
<212> TYPE: PRT
<213> ORGANISM: Artificial Sequence
```

```
<220> FEATURE:
<223> OTHER INFORMATION: 28H1 light chain CDR1

<400> SEQUENCE: 72

Ser Arg Ser Tyr Leu Ala
1               5

<210> SEQ ID NO 73
<211> LENGTH: 7
<212> TYPE: PRT
<213> ORGANISM: Artificial Sequence
<220> FEATURE:
<223> OTHER INFORMATION: 28H1 light chain CDR2

<400> SEQUENCE: 73

Gly Ala Ser Thr Arg Ala Thr
1               5

<210> SEQ ID NO 74
<211> LENGTH: 9
<212> TYPE: PRT
<213> ORGANISM: Artificial Sequence
<220> FEATURE:
<223> OTHER INFORMATION: 28H1 light chain CDR3

<400> SEQUENCE: 74

Gln Gln Gly Gln Val Ile Pro Pro Thr
1               5

<210> SEQ ID NO 75
<211> LENGTH: 108
<212> TYPE: PRT
<213> ORGANISM: Artificial Sequence
<220> FEATURE:
<223> OTHER INFORMATION: 28H1 light chain variable region

<400> SEQUENCE: 75

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 76
<211> LENGTH: 5
<212> TYPE: PRT
<213> ORGANISM: Artificial Sequence
<220> FEATURE:
<223> OTHER INFORMATION: 28H1 heavy chain CDR1

<400> SEQUENCE: 76

Ser His Ala Met Ser
1               5
```

```
<210> SEQ ID NO 77
<211> LENGTH: 16
<212> TYPE: PRT
<213> ORGANISM: Artificial Sequence
<220> FEATURE:
<223> OTHER INFORMATION: 28H1 heavy chain CDR2

<400> SEQUENCE: 77

Ala Ile Trp Ala Ser Gly Glu Gln Tyr Tyr Ala Asp Ser Val Lys Gly
1               5                  10                  15

<210> SEQ ID NO 78
<211> LENGTH: 8
<212> TYPE: PRT
<213> ORGANISM: Artificial Sequence
<220> FEATURE:
<223> OTHER INFORMATION: 28H1 heavy chain CDR3

<400> SEQUENCE: 78

Gly Trp Leu Gly Asn Phe Asp Tyr
1               5

<210> SEQ ID NO 79
<211> LENGTH: 116
<212> TYPE: PRT
<213> ORGANISM: Artificial Sequence
<220> FEATURE:
<223> OTHER INFORMATION: 28H1 heavy chain variable region

<400> SEQUENCE: 79

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Gln Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser
        115

<210> SEQ ID NO 80
<211> LENGTH: 160
<212> TYPE: PRT
<213> ORGANISM: Artificial Sequence
<220> FEATURE:
<223> OTHER INFORMATION: IL10

<400> SEQUENCE: 80

Ser Pro Gly Gln Gly Thr Gln Ser Glu Asn Ser Cys Thr His Phe Pro
1               5                  10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
```

```
                50                    55                   60

Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
                100                 105                 110

Pro Cys Glu Asn Lys Ser Lys Ala Val Glu Gln Val Lys Asn Ala Phe
                115                 120                 125

Asn Lys Leu Gln Glu Lys Gly Ile Tyr Lys Ala Met Ser Glu Phe Asp
                130                 135                 140

Ile Phe Ile Asn Tyr Ile Glu Ala Tyr Met Thr Met Lys Ile Arg Asn
145                 150                 155                 160

<210> SEQ ID NO 81
<211> LENGTH: 480
<212> TYPE: DNA
<213> ORGANISM: Artificial Sequence
<220> FEATURE:
<223> OTHER INFORMATION: gene of IL10

<400> SEQUENCE: 81
agccccggcc agggcacaca gtccgagaac agctgcaccc actttcccgg caacctgcct    60
aacatgctga gggacctgag ggacgccttc agcagggtga agaccttctt ccagatgaag   120
gaccagctgg ataacctgct gctgaaggag agcctgctgg aggacttcaa gggctacctg   180
ggctgccagg ccctgagcga gatgatccag ttctacctgg aggaggtgat gccccaggcc   240
gagaaccagg accccgacat caaggcccac gtgaacagcc tgggcgagaa cctgaagacc   300
ctgaggctga ggctgaggag gtgccacagg ttcctgccct gtgagaacaa atccaaggcc   360
gtggagcagg tgaagaacgc cttcaacaag ctgcaggaaa agggcatcta caaggccatg   420
agcgagttcg acatctttat caactatatc gaggcctaca tgacaatgaa gatcaggaac   480

<210> SEQ ID NO 82
<211> LENGTH: 335
<212> TYPE: PRT
<213> ORGANISM: Artificial Sequence
<220> FEATURE:
<223> OTHER INFORMATION: (IL10)2

<400> SEQUENCE: 82

Ser Pro Gly Gln Gly Thr Gln Ser Glu Asn Ser Cys Thr His Phe Pro
  1               5                  10                  15

Gly Asn Leu Pro Asn Met Leu Arg Asp Leu Arg Asp Ala Phe Ser Arg
                 20                  25                  30

Val Lys Thr Phe Phe Gln Met Lys Asp Gln Leu Asp Asn Leu Leu Leu
                 35                  40                  45

Lys Glu Ser Leu Leu Glu Asp Phe Lys Gly Tyr Leu Gly Cys Gln Ala
 50                  55                  60

Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
                100                 105                 110

Pro Cys Glu Asn Lys Ser Lys Ala Val Glu Gln Val Lys Asn Ala Phe
                115                 120                 125
```

```
Asn Lys Leu Gln Glu Lys Gly Ile Tyr Lys Ala Met Ser Glu Phe Asp
        130                 135                 140
Ile Phe Ile Asn Tyr Ile Glu Ala Tyr Met Thr Met Lys Ile Arg Asn
145                 150                 155                 160
Gly Gly Gly Gly Ser Gly Gly Gly Ser Gly Gly Gly Ser Ser
                165                 170                 175
Pro Gly Gln Gly Thr Gln Ser Glu Asn Ser Cys Thr His Phe Pro Gly
                180                 185                 190
Asn Leu Pro Asn Met Leu Arg Asp Leu Arg Asp Ala Phe Ser Arg Val
        195                 200                 205
Lys Thr Phe Phe Gln Met Lys Asp Gln Leu Asp Asn Leu Leu Leu Lys
        210                 215                 220
Glu Ser Leu Leu Glu Asp Phe Lys Gly Tyr Leu Gly Cys Gln Ala Leu
225                 230                 235                 240
Ser Glu Met Ile Gln Phe Tyr Leu Glu Glu Val Met Pro Gln Ala Glu
                245                 250                 255
Asn Gln Asp Pro Asp Ile Lys Ala His Val Asn Ser Leu Gly Glu Asn
                260                 265                 270
Leu Lys Thr Leu Arg Leu Arg Leu Arg Arg Cys His Arg Phe Leu Pro
        275                 280                 285
Cys Glu Asn Lys Ser Lys Ala Val Glu Val Lys Asn Ala Phe Asn
290                 295                 300
Lys Leu Gln Glu Lys Gly Ile Tyr Lys Ala Met Ser Glu Phe Asp Ile
305                 310                 315                 320
Phe Ile Asn Tyr Ile Glu Ala Tyr Met Thr Met Lys Ile Arg Asn
                325                 330                 335

<210> SEQ ID NO 83
<211> LENGTH: 1005
<212> TYPE: DNA
<213> ORGANISM: Artificial Sequence
<220> FEATURE:
<223> OTHER INFORMATION: gene of (IL10)2

<400> SEQUENCE: 83
agccccggcc agggcacaca gtccgagaac agctgcaccc actttcccgg caacctgcct      60
aacatgctga gggacctgag ggacgccttc agcagggtga agaccttctt ccagatgaag     120
gaccagctgg ataacctgct gctgaaggag agcctgctgg aggacttcaa gggctacctg     180
ggctgccagg ccctgagcga gatgatccag ttctacctgg aggaggtgat gccccaggcc     240
gagaaccagg accccgacat caaggcccac gtgaacagcc tgggcgagaa cctgaagacc     300
ctgaggctga ggctgaggag gtgccacagg ttcctgccct gtgagaacaa atccaaggcc     360
gtggagcagg tgaagaacgc cttcaacaag ctgcaggaaa agggcatcta caaggccatg     420
agcgagttcg acatctttat caactatatc gaggcctaca tgacaatgaa gatcaggaac     480
ggcggcggcg gcagcggggg cggcggcagc ggaggaggcg gcagcagccc cggccagggc     540
acacagtccg agaacagctg cacccacttt cccggcaacc tgcctaacat gctgagggac     600
ctgagggacg ccttcagcag ggtgaagacc ttcttccaga tgaaggacca gctggataac     660
ctgctgctga aggagagcct gctggaggac ttcaagggct acctgggctg ccaggccctg     720
agcgagatga tccagttcta cctggaggag gtgatgcccc aggccgagaa ccaggacccc     780
gacatcaagg cccacgtgaa cagcctgggc gagaacctga gaccctgag gctgaggctg     840
aggaggtgcc acaggttcct gccctgtgag aacaaatcca aggccgtgga gcaggtgaag     900
```

```
aacgccttca acaagctgca ggaaaagggc atctacaagg ccatgagcga gttcgacatc    960
tttatcaact atatcgaggc ctacatgaca atgaagatca ggaac                   1005
```

<210> SEQ ID NO 84
<211> LENGTH: 11
<212> TYPE: PRT
<213> ORGANISM: Artificial Sequence
<220> FEATURE:
<223> OTHER INFORMATION: Pertuzumab light chain CDR1

<400> SEQUENCE: 84

Lys Ala Ser Gln Asp Val Ser Ile Gly Val Ala
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Pertuzumab light chain CDR2

<400> SEQUENCE: 85

Ser Ala Ser Tyr Arg Tyr Thr
1               5

<210> SEQ ID NO 86
<211> LENGTH: 9
<212> TYPE: PRT
<213> ORGANISM: Artificial Sequence
<220> FEATURE:
<223> OTHER INFORMATION: Pertuzumab light chain CDR3

<400> SEQUENCE: 86

Gln Gln Tyr Tyr Ile Tyr Pro Tyr Thr
1               5

<210> SEQ ID NO 87
<211> LENGTH: 107
<212> TYPE: PRT
<213> ORGANISM: Artificial Sequence
<220> FEATURE:
<223> OTHER INFORMATION: Pertuzumab light chain variable region

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 88
<211> LENGTH: 5
<212> TYPE: PRT

```
<213> ORGANISM: Artificial Sequence
<220> FEATURE:
<223> OTHER INFORMATION: Pertuzumab heavy chain CDR1

<400> SEQUENCE: 88

Asp Tyr Thr Met Asp
1               5

<210> SEQ ID NO 89
<211> LENGTH: 17
<212> TYPE: PRT
<213> ORGANISM: Artificial Sequence
<220> FEATURE:
<223> OTHER INFORMATION: Pertuzumab heavy chain CDR2

<400> SEQUENCE: 89

Asp Val Asn Pro Asn Ser Gly Gly Ser Ile Tyr Asn Gln Arg Phe Lys
1               5                   10                  15

Gly

<210> SEQ ID NO 90
<211> LENGTH: 10
<212> TYPE: PRT
<213> ORGANISM: Artificial Sequence
<220> FEATURE:
<223> OTHER INFORMATION: Pertuzumab heavy chain CDR3

<400> SEQUENCE: 90

Asn Leu Gly Pro Ser Phe Tyr Phe Asp Tyr
1               5                   10

<210> SEQ ID NO 91
<211> LENGTH: 119
<212> TYPE: PRT
<213> ORGANISM: Artificial Sequence
<220> FEATURE:
<223> OTHER INFORMATION: Pertuzumab heavy chain variable region

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

METHODS AND COMPOSITIONS FOR CANCER TREATMENT

CROSS-REFERENCE TO RELATED APPLICATIONS

This application is a National Stage Application and claims priority under 35 U.S.C. § 371 to Patent Cooperation Treaty application PCT/CN2017/103197, filed Sep. 25, 2017, and to Patent Cooperation Treaty application PCT/CN2018/107101, filed Sep. 21, 2018, which also claims the benefit PCT/CN2017/103197, filed Sep. 25, 2017. Priority is claimed to both these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "2020-03_262790-464294_Sequence_Listing_ST25.txt," is 136,139 bytes in size and was created on Mar. 20, 2020, and filed electronically herewith.

BACKGROUND

Although immune responses against tumor antigens can be detected (Disis et al. (1997) *J. Clin. Oncol.* 15: 3363-3367), malignant cells causing diseases often fail to elicit an immune response that leads to rejection. Studies have demonstrated that it is possible to enhance the immunogenicity of tumor cells by introducing immunoregulatory molecules such as cytokines and costimulatory molecules into them; however, eradication of residual cancer cells may require the targeting of widely scattered micrometastatic tumor deposits that are not accessible to direct gene transfer. In addition, the expression and stability of the immunoregulatory molecules introduced are often far from satisfactory. Immunoregulators, such as cytokines, produced by cells of the immune system can, directly or indirectly, activate the cells of the adaptive immune response and can play an important role in eliciting protective antitumor immunity. The innate immune system can be triggered by bacterial products or "danger" signals that lead to the release of proinflammatory cytokines, such as interleukins.

Multiple studies have shown that immunoregulators may be useful in exerting antitumor effects in both animal models and cancer patients. However, short half-life and systemic toxicity related with application of the immunoregulators have greatly limited their usage. In CN200880117225.8, a chimeric construct comprising an interferon attached to the c-terminus of an antibody targeting a tumor associated antigen has been described. However, fusion proteins expressed from such a chimeric construct are typically very unstable in vivo, and the expression yield thereof is typically not high enough for industrial-scale production.

Besides immunotherapy, surgery, chemotherapy, hormonal therapy and radiation therapy have also been used to treat cancer (see, for example, Stockdale, 1998, "Principles of Cancer Patient Management", in *Scientific American: Medicine*, vol. 3, Rubenstein and Federman, eds., Chapter 12, Section IV). However, surgery may be impossible or unacceptable due to patient health conditions or advanced disease stages, and frequently, cancer cells cannot be completely removed from the patients after surgery. Radiation therapy is only effective when the neoplastic tissue exhibits a higher sensitivity to radiation than normal tissue, and high dosage of radiation therapy can often elicit serious side effects. Hormonal therapy is rarely given as a single agent and although can be effective, is often used to prevent or delay recurrence of cancer after other treatments have removed the majority of the cancer cells. Further, patients may develop drug resistance pretty quickly to chemotherapy agents.

Thus, novel and effective therapies for cancer treatment are still much desired.

SUMMARY OF THE INVENTION

The present disclosure provides compositions and methods for treating cancer, comprising the use of an immunoconjugate in combination with a cytotoxic agent or a cytotoxic therapy, the inventions of the present disclosure showed significant synergistic effects in cancer treatment.

In one aspect, the present disclosure provides a composition comprising an immunoconjugate and a cytotoxic agent, wherein: said immunoconjugate comprises 1) one or more interleukins, and 2) an Fc domain consisting of a first Fc subunit and a second Fc subunit, said first Fc subunit associates with said second Fc subunit to form a dimer; said one or more interleukins are fused to said Fc domain; and wherein said cytotoxic agent is capable of inducing immunogenic cell death.

In some embodiments, at least one of said one or more interleukins is fused to an amino-terminal amino acid of said Fc domain.

In some embodiments, said immunoconjugate comprises two or more interleukins.

In some embodiments, at least two of said two or more interleukins are fused to an amino-terminal amino acid of said Fc domain.

In some embodiments, at least two of said two or more interleukins are fused to each other through a peptide linker to form an interleukin dimer.

In some embodiments, at least one of said interleukin dimer is fused to an amino-terminal amino acid of said Fc domain.

In some embodiments, said two or more interleukins are two or more copies of the same interleukin. In some embodiments, said two or more interleukins are two or more copies of IL10.

In some embodiments, said immunoconjugate further comprises a targeting moiety fused to said Fc domain, wherein said targeting moiety exhibits binding specificity to a tumor antigen. In some embodiments, said targeting moiety is fused to an amino-terminal amino acid of said Fc domain. In some embodiments, said tumor antigen is selected from the group consisting of: EGFR, HER2/neu, and FAP. In some embodiments, said Fc domain is an IgG Fc domain. In some embodiments, said IgG is a human IgG1.

In some embodiments, said immunoconjugate is an immunoconjugate comprising a first member and a second member different from said first member, wherein said first member comprises said first Fc subunit, and said second member comprises said one or more interleukins fused to said second Fc subunit, and said first Fc subunit associates with said second Fc subunit to form a heterodimer.

In some embodiments, at least one of said one or more interleukins is fused to the amino-terminal amino acid of said second Fc subunit.

In some embodiments, in said second member, at least two of said one or more interleukins are fused to each other to form an interleukin dimer, and said interleukin dimer is further fused to the amino-terminal amino acid of said second Fc subunit.

In some embodiments, wherein said first member further comprises said targeting moiety fused to said first Fc subunit.

In some embodiments, wherein said immunoconjugate does not comprise any targeting moiety.

In some embodiments, said first Fc subunit is different from said second Fc subunit, and said Fc domain comprises a modification promoting heterodimerization between said first Fc subunit and said second Fc subunit.

In some embodiments, wherein said first Fc subunit comprises a first modification, and said second Fc subunit comprises a second modification, and the first modification and the second modification comprise an amino acid substitution at a group of positions selected from any of the following groups: 1) the first modification: Y349 and T366; and the second modification: D356, T366, L368, Y407 and F405; 2) the first modification: Y349, T366 and F405; and the second modification: D356, T366, L368 and Y407; 3) the first modification: Y349, T366 and K409; and the second modification: D356, T366, L368, Y407 and F405; 4) the first modification: Y349, T366, F405, K360 and Q347; and the second modification: D356, T366, L368, Y407 and Q347; 5) the first modification: Y349, T366, F405 and Q347; and the second modification: D356, T366, L368, Y407, K360 and Q347; 6) the first modification: Y349, T366, K409, K360 and Q347; and the second modification: D356, T366, L368, Y407, F405 and Q347; 7) the first modification: Y349, T366, K409 and Q347; and the second modification: D356, T366, L368, Y407, F405, K360 and Q347; 8) the first modification: T366, K409 and K392; and the second modification: T366, L368, Y407, D399 and F405; 9) the first modification: T366 and K409; and the second modification: T366, L368, Y407 and F405; 10) the first modification: T366, K409 and Y349; and the second modification: T366, L368, Y407, F405 and E357; 11) the first modification: T366, K409, Y349 and S354; and the second modification: T366, L368, Y407, F405 and E357; 12) the first modification: T366 and F405; and the second modification: T366, L368, Y407 and K409; 13) the first modification: T366, F405 and D399; and the second modification: T366, L368, Y407, K409 and K392; 14) the first modification: T366, F405 and Y349; and the second modification: T366, L368, Y407, K409 and E357; 15) the first modification: T366, F405, Y349 and S354; and the second modification: T366, L368, Y407, K409 and E357; wherein the position of the amino acid is determined according to the EU index of the KABAT number.

In some embodiments, wherein said cytotoxic agent capable of inducing immunogenic cell death is selected from the group consisting of: an alkylating agent, an antimetabolite, an anthracycline, a plant alkaloid, a platinum-based compound, and a radiation agent.

In some embodiments, wherein said cytotoxic agent capable of inducing immunogenic cell death comprises an alkylating agent selected from cyclophosphamide.

In some embodiments, wherein said cytotoxic agent capable of inducing immunogenic cell death comprises an antimetabolite selected from the group consisting of: capecitabine, gemcitabine, pemetrexed and 5-Fu.

In some embodiments, wherein said cytotoxic agent capable of inducing immunogenic cell death comprises an anthracycline selected from the group consisting of: bleomycin, doxorubicin and mitomycin-C.

In some embodiments, wherein said cytotoxic agent capable of inducing immunogenic cell death comprises a plant alkaloid selected from the group consisting of: taxane, docetaxel, paclitaxel, vinblastine, vincristine and vinorelbine.

In some embodiments, wherein said cytotoxic agent capable of inducing immunogenic cell death comprises a radiation agent that emits X-ray radiation and/or gamma-ray radiation.

In some embodiments, wherein said cytotoxic agent capable of inducing immunogenic cell death comprises a platinum-based compound selected from the group consisting of: carboplatin, cisplatin and oxaliplatin.

In other aspects, the present disclosure provides the use of an immunoconjugate in combination with a cytotoxic therapy in the preparation of a medicament for treating cancer in a subject in need thereof, wherein said immunoconjugate is as defined in the present disclosure, and said cytotoxic therapy is capable of inducing immunogenic cell death.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

DETAILED DESCRIPTION

Figure 1A:
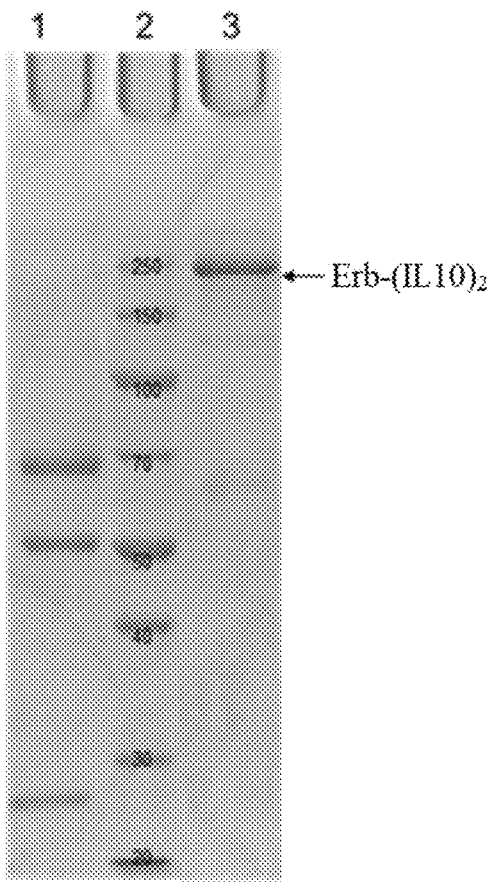
FIGS. 1A-1F illustrate the purification result of the immunoconjugate of the present disclosure, as shown by SDS-PAGE and SEC-HPLC analysis.

Before the embodiments of the disclosure are described, it is to be understood that such embodiments are provided by way of example only, and that various alternatives to the embodiments of the disclosure described herein may be employed in practicing the disclosure. Numerous variations, changes, and substitutions will now occur to those skilled in the art without departing from the disclosure.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the disclosure.

The singular form "a," "an" and "the," as used herein, generally include plural references unless the context clearly dictates otherwise.

The term "immunoconjugate", as used herein, generally refers to a proteinaceous molecule formed by the conjugation of one or more antibodies or a fragment thereof to one or more second molecules. The second molecule may be the same or different, and may include for example, effector proteins.

The term "proteinaceous," as used herein, generally refers to a material or molecule that is of, relating to, resembling, or being a polypeptide or a protein. For example, a immunoconjugate of the present disclosure may be a heterodimer protein, or a heterodimer comprising two or more polypeptides.

The term "heterodimer," as used herein, generally refers to a molecule (e.g. a proteinaceous molecule) composed of two different members. The two members of a heterodimer may differ in structure, function, activity and/or composition. For example, the two different members may comprise polypeptides differing in the order, number, or kind of amino acid residues forming these polypeptides. Each of the two different members of a heterodimer may independently comprise one, two or more units, polypeptide chains, or moieties.

The term "targeting moiety," as used herein, generally refers to a molecule, complex or aggregate, that binds specifically, selectively or preferentially to a target molecule, cell, particle, tissue or aggregate. For example, a targeting moiety may be an antibody, antigen-binding antibody fragment, bispecific antibody or other antibody-based molecule or compound. Other examples of targeting moieties may include, but are not limited to, aptamers, avimers, receptor-binding ligands, nucleic acids, biotin-avidin binding pairs, binding peptides or proteins, etc. The terms "targeting moiety" and "binding moiety" are used interchangeably herein.

The term "tumor antigen," as used herein, generally refers to an antigenic substance produced in or by tumor cells, which may have an ability to trigger an immune response in a host. For example, a tumor antigen may be a protein, a polypeptide, a peptide, or a fragment thereof, which constitutes part of a tumor cell and is capable of inducing tumor-specific cytotoxic T lymphocytes. A tumor antigen peptide may be a peptide that is generated as a result of degradation of the tumor antigen in a tumor cell and can induce or activate tumor-specific cytotoxic T lymphocytes upon being expressed on cell surface by binding to an HLA molecule. In some embodiments, the term "tumor antigen" may also refer to biomolecules (e.g., proteins, carbohydrates, glycoproteins, etc.) that are exclusively or preferentially or differentially expressed on a cancer cell and/or are found in association with a cancer cell and thereby provide targets preferential or specific to the cancer. For example, the preferential expression can be preferential expression as compared to any other cell in the organism, or preferential expression within a particular area of the organism (e.g. within a particular organ or tissue).

The term "heterodimerization," as used herein, generally refers to the process of forming a heterodimer between two different members (e.g., two non-identical polypeptides), such as through complexation, association, or aggregation, with or without formation of covalent bonds between the two different members.

The term "covalent bond," as used herein, generally refers to a chemical bond formed between atoms by the sharing of electrons. For example, a covalent bond may be polar or non-polar. In some embodiments, a covalent bond is a disulfide bond.

The term "non-covalent pairwise affinity," as used herein, generally refers to that dimerization sequences or heterodimerization sequences capable of binding each other via non-covalent interaction, e.g., via ion pairs, hydrogen bonds, dipole-dipole interactions, charge transfer interactions, π-π interactions, cation-π-electron interactions, van der Waals interactions and disperse interactions, hydrophobic (lipophilic) interactions, complex formation (e.g., complex formation of transition metal cations), or a combination of these interactions.

The term "linker," as used herein, generally refers to a synthetic amino acid sequence that connects or links two polypeptide sequences, e.g., that link two polypeptide domains. A linker may connect two amino acid sequences via peptide bonds. In some embodiments, a linker of the present disclosure connects a biologically active moiety to a second moiety in a linear sequence.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation, or any other manipulation, such as conjugation with a labeling component. The terms may apply to amino acid polymers in which one or more amino acid residue is an artificial chemical analogue of a corresponding naturally occurring amino acid, as well as to naturally occurring amino acid polymers. The terms may also include variants on the traditional peptide linkage joining the amino acids making up the polypeptide. For example, the "peptides," "polypeptides," and "proteins" may be chains of amino acids whose alpha carbons are linked through peptide bonds. The terminal amino acid at one end of the chain (amino terminal) therefore may have a free amino group, while the terminal amino acid at the other end of the chain (carboxy terminal) may have a free carboxyl group. As used herein, the term "amino terminus" (abbreviated N-terminus) generally refers to the free α-amino group on an amino acid at the amino terminal of a peptide or to the α-amino group (amino group when participating in a peptide bond) of an amino acid at any other location within the peptide. Similarly, the term "carboxy terminus" generally refers to the free carboxyl group on the carboxy terminus of a peptide or the carboxyl group of an amino acid at any other location within the peptide. Peptides may also include essentially any poly-amino acid including, but not limited to peptide mimetics such as amino acids joined by a ether as opposed to an amide bond.

The term "amino acid," as used herein, generally refers to either natural and/or unnatural or synthetic amino acids, including but not limited to, the D or L optical isomers or both, amino acid analogs and peptidomimetics. Standard single or three letter codes are used to designate amino acids.

The term "variant," when used in the context of a proteinaceous molecule (e.g., a polypeptide or a protein), generally refers to a proteinaceous molecule with sequence homology to the native biologically active protein that retains at least a portion of the therapeutic and/or biological activity of the biologically active protein. For example, a variant protein may share at least 60%, 65%, 70%, 75%, 80%, 85%, 90%, 95%, 96%, 97%, 98% or 99% amino acid sequence identity compared with the reference biologically active protein. In some embodiments, the "variant" may include proteins modified deliberately, as for example, by site directed mutagenesis, synthesis of the encoding gene, insertions, or accidentally through mutations.

The terms "conjugated," "linked," "fused," and "fusion" are used interchangeably herein, and generally refer to the joining together of two or more chemical elements, sequences or components, e.g., by means including chemical conjugation or recombinant means. For example, a promoter or enhancer is operably linked to a coding sequence if it effects the transcription of the sequence. Generally, "operably linked" means that the DNA sequences being linked are contiguous, and in reading phase or in-frame. An "in-frame fusion" refers to the joining of two or more open reading frames (ORFs) to form a continuous longer ORF, in a manner that maintains the correct reading frame of the original ORFs. Thus, the resulting "fusion polypeptide" is a single protein containing two or more fragments that correspond to polypeptides encoded by the original ORFs (which segments are not normally so joined in nature). The "fusion site" refers to the sequence where the two or more fragments are joined together. In some cases, the fusion site can be a sequence that is identical to sequences in the two or more fragments being joined. In some cases, the fusion site can further comprise a gap segment that is not identical to either of the sequences of the two or more fragments being joined.

In the context of polypeptides, a "linear sequence" or a "sequence" is an order of amino acids in a polypeptide in an amino to carboxyl terminus direction in which residues next to each other in the sequence are contiguous in the primary structure of the polypeptide. A "partial sequence" is a linear sequence forming part of a polypeptide that is known to comprise additional residues in one or both directions.

The terms "polynucleotides," "nucleic acids," "nucleotides" and "oligonucleotides" are used interchangeably herein, and they generally refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The terms "gene" and "gene fragment" are used interchangeably herein and generally refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof. A "fusion gene" is a gene composed of at least two heterologous polynucleotides that are linked together.

The term "antibody," as used herein, generally refers to a protein comprising one or more polypeptides substantially encoded by immunoglobulin genes or fragments of immunoglobulin genes. The immunoglobulin genes may include the kappa, lambda, alpha, gamma, delta, epsilon and mu constant region genes, as well as myriad immunoglobulin variable region genes. As used herein, light chains may be classified as either kappa or lambda. Heavy chains may be classified as gamma, mu, alpha, delta, or epsilon, which in turn define the immunoglobulin classes, IgG, IgM, IgA, IgD and IgE, respectively. An antibody as used in the present disclosure may have a structural unit comprising a tetramer. Each tetramer may be composed of two identical pairs of polypeptide chains, each pair having one "light" (about 25 KD) and one "heavy" chain (about 50-70 KD). The N-terminus of each chain may define a variable region of about 100 to 110 or more amino acids primarily responsible for antigen recognition. The terms "light chain variable region" (VL) and "heavy chain variable region" (VH), as used herein, generally refer to these regions of the light and heavy chains respectively. Antibodies may exist as intact immunoglobulins or as a number of well characterized fragments produced by digestion with various peptidases or expressed de novo. Thus, for example, pepsin may digest an antibody below the disulfide linkages in the hinge region to produce F(ab)'2 (a dimer of Fab which itself is a light chain joined to VH—CH1 by a disulfide bond). The F(ab)'2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. Thus, the term antibody, as used herein, may also include antibody fragments either produced by the modification of whole antibodies or synthesized de novo using recombinant DNA methodologies, including, but are not limited to, Fab'2, IgG, IgM, IgA, IgE, scFv, dAb, nanobodies, unibodies, and diabodies. In some embodiments, the antibodies include, but are not limited to Fab'2, IgG, IgM, IgA, IgE, and single chain antibodies, for example, single chain Fv (scFv) antibodies in which a variable heavy and a variable light chain are joined together (directly or through a peptide linker) to form a continuous polypeptide.

The term "antigen-binding site" or "binding portion," as used herein, generally refers to a part of an antibody that participates in antigen binding. An antigen binding site may be formed by amino acid residues of the N-terminal variable ("V") regions of a heavy ("H") chain and/or a light ("L") chain. Three highly divergent stretches within the V regions of the heavy and light chains are referred to as "hypervariable regions" which are interposed between more conserved flanking stretches known as "framework regions" or "FRs". Thus, the term "FR," as used herein, generally refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three-dimensional space to form an antigen binding "surface". This surface may mediate recognition and binding of the target antigen. The three hypervariable regions of each of the heavy and light chains are referred to as "complementarity determining regions" or "CDRs" and are characterized, for example by Kabat et al. *Sequences of proteins of immunological interest*, 4$^{th}$ ed. U.S. Dept. Health and Human Services, Public Health Services, Bethesda, Md. (1987).

The term "homology," "homologous" or "sequence identity," as used herein, generally refers to sequence similarity or interchangeability between two or more polynucleotide sequences or between two or more polypeptide sequences. When using a program (e.g. Emboss Needle or BestFit) to determine sequence identity, similarity or homology between two different amino acid sequences, the default settings may be used, or an appropriate scoring matrix, such as blosum45 or blosum80, may be selected to optimize identity, similarity or homology scores. In some embodiments, polynucleotides that are homologous are those which hybridize under stringent conditions and have at least 60%, at least 65%, at least 70%, at least 80%, at least 90%, at least 95%, at least 97%, at least 98%, at least 99%, and even 100% sequence identity compared to those sequences. Polypeptides that are homologous have sequence identities of at least 80%, or at least 90%, or at least 95%, or at least 97%, or at least 98%, or have at least 99% sequence identity when sequences of comparable length are optimally aligned.

The term "effective amount" or "therapeutically effective amount" refers to an amount of a composition that is sufficient to effect the intended application, including but not limited to disease treatment. The therapeutically effective amount may vary depending upon the intended application (e.g., in vitro or in vivo), or the subject and disease condition being treated, e.g., the weight and age of the subject, the severity of the disease condition, the manner of administration and the like, which can readily be determined by one of ordinary skill in the art. The term may also apply to a dose that will induce a particular response in target cells, e.g. target gene induction, proliferation, and/or apoptosis. The specific dose will vary depending on the particular compounds chosen, the dosing regimen to be followed, whether it is administered in combination with other compounds, timing of administration, the tissue to which it is administered, and the physical delivery system in which it is carried.

The terms "treatment" or "treating," or "palliating" or "ameliorating" is used interchangeably herein, and refer to an approach for obtaining beneficial or desired results including but not limited to a therapeutic benefit and/or a prophylactic benefit. As used herein, therapeutic benefit generally refers to eradication or reduced severity of the underlying disorder being treated. Also, a therapeutic benefit is achieved with the eradication, reduced severity or reduced incidence of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

The term "therapeutic effect," as used herein, generally encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," "use in combination with," and their grammatical equivalents, as used herein, generally encompass administration of two or more agents or therapies to a subject so that both agents and/or their metabolites, or both therapies are present and/or function in the subject. Co-administration includes simultaneous administration in separate compositions or forms, administration at different time pointes in separate compositions or forms, or administration in a composition in which both agents are present.

The term "agent" as used herein, generally refers to a biological, pharmaceutical, or chemical compound or other moieties. Non-limiting examples include a simple or complex organic or inorganic molecule, a peptide, a protein, an oligonucleotide, an antibody, an antibody derivative, antibody fragment, a vitamin derivative, a carbohydrate, a toxin, a chemotherapeutic compound, or an agent capable of generating/emitting radiation.

The term "interleukin," as used herein, generally refers to a secreted protein or a signaling molecule capable of promoting the development and differentiation of T and/or B lymphocytes and/or hematopoietic cells. An interleukin may be synthesized by helper CD4 T lymphocytes, as well as through monocytes, macrophages, and endothelial cells. As used herein, an interleukin (IL) may include IL-1, IL-2, IL-3, IL-4, IL-5, IL-6, IL-7, IL-8, IL-9, IL-IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and/or IL-36. As used herein, the term "interleukin" may include full length interleukins, or a fragment (e.g., a truncated form) or variant thereof substantially maintaining the biological activities of a corresponding wild-type interleukin (e.g., having a biological activity that is at least 80%, at least 90%, at least 95%, at least 98%, at least 99%, or even at least 100% of the biological activity of a corresponding wild-type interleukin). An interleukin, as used herein, may be from any mammalian species. In some embodiments, the interleukin is from a species selected from the group consisting of human, horse, cattle, murine, pig, rabbit, cat, dog, rat, goat, sheep, and non-human primate. In some embodiments, the interleukin can be in a mutated form, for example, with increased or decreased affinity to its receptors.

The term "subject," as used herein, generally refers to a human or non-human animal, including, but not limited to, a cat, dog, horse, pig, cow, sheep, goat, rabbit, mouse, rat, or monkey.

The term "EGFR family member," as used herein, generally refers to a member of the epidermal growth factor receptor family. For example, it may be a ErbB-1 (also named as epidermal growth factor receptor (EGFR)), ErbB-2 (also named as HER2 in humans and as neu in rodents), ErbB-3 (also named as HER3), and/or to ErbB-4 (also named as HER4). Examples of anti-EGFR family antibodies include, but are not limited to one or more of the following antibodies: C6.5, C6mL3-9, C6 MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4.C7, etc., also see, e.g., U.S. Patent publications US 2006/0099205 A1 and US 2004/0071696 A1, which are incorporated herein by reference.

The term "anti-HER2/neu antibody" as used herein, generally refers to an antibody that specifically or preferentially binds a HER2/neu receptor. For example, an anti-HER2/neu antibody or anti-HER2 antibody could be Trastuzumab, Pertuzumab, or antigen binding fragments thereof.

The term "anti-EGFR antibody," as used herein, generally refers to an antibody that specifically or preferentially binds an EGFR. In some cases, and anti-EGFR antibody may bind to a mutated form of EGFR (e.g., EGFR variant III (also known as EGFRvIII), which is the most common extracellular domain mutation of EGFR, this mutation leads to a deletion of exons 2-7 of the EGFR gene, which is characterized by a truncated extracellular domain with ligand-independent constitutive activity). For example, an anti-EGFR antibody may be Cetuximab, Mab806, or antigen binding fragments thereof.

The term "anti-FAP antibody," as used herein, generally refers to an antibody that specifically or preferentially binds FAP. The term "FAP" as used herein, generally refers to Fibroblast Activation Protein (FAP). FAP exists in tumor matrix fibroblasts and plays a role in the cell surface. It is a membrane serine peptidase which is a member of the type II serine protease family and has dipeptidyl peptidase and collagenase activity. For example, an anti-FAP antibody could be antibody 28H1 or an antigen binding fragment thereof. In some embodiments, an anti-FAP antibody is the antibody 28H1.

The term "member" as used herein, generally refers to a polypeptide, subunit, or moiety which is one component of the immunoconjugate.

The term "Fc domain", as used herein, generally refers to an Fc part or Fc fragment of an antibody heavy chain. For example, it may refer to the carboxyl terminal portion of an immunoglobulin heavy chain constant region, or an analog or portion thereof capable of binding an Fc receptor. As is known, each immunoglobulin heavy chain constant region comprises four or five domains. The domains are named sequentially as follows: CH1-hinge-CH2-CH3(—CH4). CH4 is present in IgM, which has no hinge region. The immunoglobulin heavy chain constant region useful in the present disclosure may comprise an immunoglobulin hinge region, and may also include a CH3 domain. For example, the immunoglobulin heavy chain constant region may comprise an immunoglobulin hinge region, a CH2 domain and a CH3 domain. In some embodiments, the Fc domain according to the present disclosure consists of the hinge-CH2-CH3 domain.

The term "Fc subunit", as used herein, generally refers to a component of an Fc domain. For example, an Fc domain may be formed by two or more members, and each member may be considered as one Fc subunit.

The term "complexed with" as used herein, generally refers to the association (e.g., binding) of one member/subunit with another member/subunit of a molecule (e.g., an antibody). For example, a light chain may be complexed with a heavy chain to form a targeting moiety.

The term "binding specificity" as used herein, generally refers to the ability to specifically bind (e.g., immune-react with) a given target (while not binding or substantially not binding a non-target). A targeting moiety of the present disclosure may be monospecific and contain one or more binding sites which specifically bind a target or may be multispecific (e.g., bispecific or trispecific) and contain two or more binding sites which specifically bind the same or different targets.

The term "associates with" or "associated with" as used herein, generally refers to that one entity is in physical association or contact with another. For example, a first member of the immunoconjugate may "associate with" a second member covalently or non-covalently. In some embodiments, a first member of the immunoconjugate associates with a second member via an interface, and the interface is formed by amino acid residues (i.e., interface residues) from the first member and the second member, respectively.

The term "modification" as used herein, generally refers to any manipulation of the peptide backbone (e.g. amino acid sequence) or any post-translational modifications (e.g. glycosylation) of a polypeptide. For example, a modification is in comparison to the sequence of a corresponding wild-type polypeptide. A modification may be a substitution, an addition, and/or a deletion of one or more amino acids (e.g., 1, 2, 3, 4, 5, 6, 7, 8, 9, 10, or more).

The term "fusion protein" as used herein, generally refers to a polypeptide that comprises, or alternatively consists of, an amino acid sequence of a polypeptide fused directly or indirectly (e.g., via a linker) to an amino acid sequence of a heterologous polypeptide (i.e., a polypeptide unrelated to the former polypeptide or the domain thereof).

The term "C-terminus" as used herein, generally refers to the carboxy terminus of a polypeptide.

The term "N-terminus" as used herein, generally refers to the amino terminus of a polypeptide.

The term "immunoglobulin" as used herein, generally refers to a protein consisting of one or more polypeptides substantially encoded by immunoglobulin genes. The recognized immunoglobulin genes include the κ, λ, α, γ (IgG1, IgG2, IgG3, IgG4), δ, ε and μ constant region genes, as well as the myriad immunoglobulin variable region genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, Fab' and (Fab')2.

The term "fused in frame" as used herein, generally refers to the joining of two or more open reading frames (ORFs)

to form a continuous longer ORF, in a manner that maintains the correct reading frame of the original ORFs.

The term "amino acid substitution" as used herein, generally refers to that one amino acid at a specific position of a polypeptide is replaced by another amino acid.

The term "EU index of the KABAT number" as used herein, generally refers to the index of the EU number corresponding to the amino acid sequence according to Kabat et al. (1971) *Ann. NY Acad, Sci.* 190:382-391 and Kabat, E. A., et al. (1991) *Sequences of Proteins of Immunological Interest*, Fifth Edition, U.S. Department of Health and Human Services, NIH Publication No. 91-3242.

The terms "isolated polynucleotide" and "isolated nucleic acid" are used interchangeably here, and generally refers to a polymeric form of nucleotides of any length, either deoxyribonucleotides or ribonucleotides, or analogs thereof, isolated from its native environment, or that is artificially synthesized.

The term "pharmaceutically acceptable excipient" as used herein, generally refers to any and all solvents, dispersion media, coatings, isotonic and absorption delaying agents, etc., that are compatible with pharmaceutical administration.

The term "cytotoxic agent" as used herein, generally refers to a substance or approach that inhibits or prevents the function of cells and finally causes destruction of cells and/or cell death, especially tumor cell death. A cytotoxic agent may include radioactive isotopes, chemotherapeutic agents, and toxins such as enzymatically active toxins of bacterial, fungal, plant or animal origin, or fragments thereof.

The terms "immunogenic cell death" and "immunogenic apoptosis" are used interchangeably herein, and generally refers to a form of cell death that induces an effective anti-tumor immune response through an activation of e.g., dendritic cells (DCs) and consequent activation of specific T cell responses. Immunogenic cell death may be characterized by secretion of damage-associated molecular patterns (DAMPs). The DAMPs may include Calreticulin (CRT), heat-shock proteins (HSPs), secreted amphoterin (HMGB1), ATP, etc. CRTs is normally in the lumen of endoplasmic reticulum (ER), and may be translocated after the induction of immunogenic apoptosis to the surface of dying cell where it functions as an "eat me" signal for professional phagocytes. HSPs comprise HSP70 and HSP90, which under stress condition may also be translocated to the plasma membrane. HMGB1 is considered to be late apoptotic marker and its release to the extracellular space seems to be required for the optimal release and presentation of tumor antigens to dendritic cells. ATP may function as a "find-me" signal for monocytes when secreted and induces their attraction to the site of apoptosis.

The term "alkylating agent" as used herein, generally refers to the oldest and most commonly used class of chemotherapy drugs, which works by directly damaging DNA and preventing cancer cells from reproducing. They are normally cell-cycle phase non-specific, and could kill cancer cells in any phase of the cell cycle. Examples of alkylating agents may include cyclophosphamide.

The term "antimetabolite" as used herein, generally refers to a chemotherapy agent that interferes with DNA and RNA growth. They are normally cell-cycle specific, and kill cancer cells in a specific phase of cell division. Examples of antimetabolites may include capecitabine, gemcitabine, pemetrexed and 5-Fu.

The term "anthracycline" as used herein, generally refers to a class of agents originally derived from *Streptomyces*, which may be used in cancer chemotherapy. Anthracyclines may interfere with enzymes necessary for DNA replication. They may be cell-cycle non-specific, and may be used to treat a variety of cancers. Anthracyclines may include red aromatic polyketides that occur in a variety of forms due to the structural differences in the aglycone and the different sugar residues attached. Examples of anthracycline may include daunorubicin, doxorubicin, epirubicin, idarubicin, valrubicin, bleomycin, and mitomycin-C.

The term "plant alkaloid" as used herein, generally refers to agents that may inhibit or prevent mitosis or inhibit enzymes from making proteins necessary for cell reproduction. Most plant alkaloids are cell-cycle specific, but can cause damage in all phases. Examples of plant alkaloids may comprise taxanes, docetaxel, paclitaxel, vinblastine, vincristine and vinorelbine.

The term "radiation agent" as used herein, generally refers to an agent capable of generating and/or emitting a form of radiation (e.g., ionizing radiation). Examples of radiation agents may include radioisotopes and agents comprising a radioisotope. A radioisotope may be a radioactive form of an element, consisting of atoms with unstable nuclei, which may undergo radioactive decay to stable forms, emitting characteristic alpha, beta, or gamma radiation.

The terms "radiation therapy" and "radiotherapy" are used interchangeably here, and generally refer to a form of treatment that employs ionizing radiation (e.g., emitted by X-ray generators or other energy sources such as radioisotopes, for example, gamma, beta or alpha emitters) to control or kill cancer cells.

The term "fractionated radiation therapy" as used herein, generally refers to a radiation therapy having doses divided in multiple fractions (or doses), wherein one fraction (or dose) may comprise the same dosage or a different dosage than another fraction (or dose).

The term "platinum-based compound" as used herein, generally refers to an agent (e.g., a chemotherapy drug) comprising platinum or a derivative thereof. Examples of platinum-based compound may comprise carboplatin, cisplatin and oxaliplatin.

Composition Comprising a Immunoconjugate and a Cytotoxic Agent

In one aspect, the present disclosure provides a composition comprising an immunoconjugate and a cytotoxic agent. The immunoconjugate may comprise 1) one or more interleukins, and 2) an Fc domain consisting of a first Fc subunit and a second Fc subunit, and the first Fc subunit associates with the second Fc subunit to form a dimer. The one or more interleukins may be fused to the Fc domain. The cytotoxic agent may be capable of inducing immunogenic cell death.

For the immunoconjugate according to the present disclosure, at least one of the one or more interleukins (e.g., IL10) may be fused to an amino-terminal amino acid of the Fc domain (e.g., in frame). The immunoconjugate may comprise two or more interleukins. In some embodiments, at least two of the two or more interleukins are fused to an amino-terminal amino acid of the Fc domain. In some embodiments, one or more of the interleukins is fused to the Fc domain through a peptide linker (e.g., in frame). In some embodiments, at least two of the two or more interleukins are fused to each other through a peptide linker (e.g., in frame) to form an interleukin dimer. At least one the interleukin dimer may be fused to an amino-terminal amino acid of the Fc domain. In some embodiments, the two or more interleukins are two or more copies of the same interleukin. For example, the two or more interleukins are two or more copies of IL10. Thus, in some embodiments, two IL10 are fused in frame to each other (e.g. via a peptide linker) to form an IL10 dimer, then, carboxy-terminal of the IL10 dimer may be fused (e.g., in frame, for example, via a peptide linker) to an amino-terminal amino acid of the Fc domain.

The linker may be a peptide comprising 1, 2, 3, 4, 5, 6, 7, 8, 9, 10, 11, 12, 13, 14, 15, 16, 17, 18, 19, 20, 21, 22, 23, 24, 25 or more amino acids. For example, the linker may comprise 1-10 amino acids (e.g., 1, 2, 3, 4, 5, 6, 7, 8, 9, 10 or more amino acids), 1-15 amino acids (e.g., 1-11, 12, 13, 14, 15 amino acids), 1-20 amino acids, 1-30 amino acids or more. In some embodiments, the linker comprises an amino acid sequence as set forth in SEQ ID NO: 49.

The immunoconjugate may further comprise a targeting moiety fused to the Fc domain, wherein the targeting moiety may exhibit binding specificity to a tumor antigen. The tumor antigen may be any immunogenic entity or a part thereof that is specifically expressed or present in a tumor environment or on the surface of a tumor cell. In some embodiments, the tumor antigen is selected from the group consisting of: an EGFR family member (such as EGFR, or HER2/neu), and FAP.

The targeting moiety may be fused to an amino-terminal amino acid of the Fc domain. In some embodiments, the targeting moiety is fused to the Fc domain through a peptide linker or an immunoglobulin hinge region.

The targeting moiety may comprise an antigen binding domain of an antibody, for example, the antigen binding domain of an antibody may be a Fab moiety, a domain antibody or a ScFv moiety. In some embodiments, the antigen binding domain of an antibody is a Fab moiety. The antibody may be selected from the group consisting of anti-EGFR antibody, anti-HER2 antibody and anti-FAP antibody.

In some embodiments, the antibody is an anti-EGFR antibody. For example, the anti-EGFR antibody may be cetuximab. In some embodiments, the targeting moiety comprises the heavy chain CDR1-3 of cetuximab, the light chain CDR1-3 of cetuximab, the heavy chain variable region of cetuximab, the light chain variable region of cetuximab, and/or the light chain of cetuximab. For example, the targeting moiety may be a Fab moiety comprising both the heavy chain variable region and the light chain variable region of cetuximab.

For example, the targeting moiety may comprise heavy chain CDRs having an amino acid sequence that is at least 60%, 70%, 75%, 80%, 85%, 90%, 95%, 96%, 97%, 98%, 99% or 100% identical to that comprised in the corresponding heavy chain CDR1-3 of cetuximab. Alternatively or additionally, the targeting moiety may comprise light chain CDRs having an amino acid sequence that is at least 60%, 70%, 75%, 80%, 85%, 90%, 95%, 96%, 97%, 98%, 99% or 100% identical to that comprised in the corresponding light chain CDR1-3 of cetuximab. For example, the targeting moiety may comprise a heavy chain variable region having an amino acid sequence that is at least 60%, 70%, 75%, 80%, 85%, 90%, 95%, 96%, 97%, 98%, 99% or 100% identical to that comprised in the corresponding heavy chain variable region of cetuximab. For example, the targeting moiety may comprise a light chain variable region having an amino acid sequence that is at least 60%, 70%, 75%, 80%, 85%, 90%, 95%, 96%, 97%, 98%, 99% or 100% identical to that comprised in the corresponding light chain variable region of cetuximab. For example, the targeting moiety may comprise a light chain having an amino acid sequence that is at least 60%, 70%, 75%, 80%, 85%, 90%, 95%, 96%, 97%, 98%, 99% or 100% identical to that comprised in the corresponding light chain of cetuximab.

The heavy chain CDR 1-3 of cetuximab are as set forth in SEQ ID NO: 60 (CDR1), SEQ ID NO: 61 (CDR2), and SEQ ID NO: 62 (CDR3), respectively. The light chain CDR 1-3 of cetuximab are as set forth in SEQ ID NO: 56 (CDR1), SEQ ID NO: 57 (CDR2), and SEQ ID NO: 58 (CDR3), respectively. The heavy chain variable region of cetuximab is as set forth in SEQ ID NO: 63. The light chain variable region of cetuximab is as set forth in SEQ ID NO: 59.

In some embodiments, the antibody is an anti-HER2 antibody. For example, the anti-HER2 antibody may be Trastuzumab or Pertuzumab. In some embodiments, the targeting moiety comprises the heavy chain CDR1-3 of Trastuzumab or Pertuzumab, the light chain CDR1-3 of Trastuzumab or Pertuzumab, the heavy chain variable region of Trastuzumab or Pertuzumab, the light chain variable region of Trastuzumab or Pertuzumab, and/or the light chain of Trastuzumab or Pertuzumab. For example, the targeting moiety may be a Fab moiety comprising both the heavy chain variable region and the light chain variable region of Trastuzumab or Pertuzumab.

For example, the targeting moiety may comprise heavy chain CDRs having an amino acid sequence that is at least 60%, 70%, 75%, 80%, 85%, 90%, 95%, 96%, 97%, 98%, 99% or 100% identical to that comprised in the corresponding heavy chain CDR1-3 of Trastuzumab or Pertuzumab. Alternatively or additionally, the targeting moiety may comprise light chain CDRs having an amino acid sequence that is at least 60%, 70%, 75%, 80%, 85%, 90%, 95%, 96%, 97%, 98%, 99% or 100% identical to that comprised in the corresponding light chain CDR1-3 of Trastuzumab or Pertuzumab. For example, the targeting moiety may comprise a heavy chain variable region having an amino acid sequence that is at least 60%, 70%, 75%, 80%, 85%, 90%, 95%, 96%, 97%, 98%, 99% or 100% identical to that comprised in the corresponding heavy chain variable region of Trastuzumab or Pertuzumab. For example, the targeting moiety may comprise a light chain variable region having an amino acid sequence that is at least 60%, 70%, 75%, 80%, 85%, 90%, 95%, 96%, 97%, 98%, 99% or 100% identical to that comprised in the corresponding light chain variable region of Trastuzumab or Pertuzumab. For example, the targeting moiety may comprise a light chain having an amino acid sequence that is at least 60%, 70%, 75%, 80%, 85%, 90%, 95%, 96%, 97%, 98%, 99% or 100% identical to that comprised in the corresponding light chain of Trastuzumab or Pertuzumab.

The heavy chain CDR 1-3 of Trastuzumab are as set forth in SEQ ID NO: 68 (CDR1), SEQ ID NO: 69 (CDR2), and SEQ ID NO: 70 (CDR3), respectively. The light chain CDR 1-3 of Trastuzumab are as set forth in SEQ ID NO: 64 (CDR1), SEQ ID NO: 65 (CDR2), and SEQ ID NO: 66 (CDR3), respectively. The heavy chain variable region of Trastuzumab is as set forth in SEQ ID NO: 71. The light chain variable region of Trastuzumab is as set forth in SEQ ID NO: 67.

The heavy chain CDR 1-3 of Pertuzumab are as set forth in SEQ ID NO: 88 (CDR1), SEQ ID NO: 89 (CDR2), and SEQ ID NO: 90 (CDR3), respectively. The light chain CDR 1-3 of Pertuzumab are as set forth in SEQ ID NO: 84 (CDR1), SEQ ID NO: 85 (CDR2), and SEQ ID NO: 86 (CDR3), respectively. The heavy chain variable region of Pertuzumab is as set forth in SEQ ID NO: 91. The light chain variable region of Pertuzumab is as set forth in SEQ ID NO: 87.

In some embodiments, the antibody is an anti-FAP antibody. For example, the anti-FAP antibody may be 28H1. In some embodiments, the targeting moiety comprises the heavy chain CDR1-3 of 28H1, the light chain CDR1-3 of 28H1, the heavy chain variable region of 28H1, the light chain variable region of 28H1, and/or the light chain of 28H1. For example, the targeting moiety may be a Fab moiety comprising both the heavy chain variable region and the light chain variable region of 28H1.

For example, the targeting moiety may comprise heavy chain CDRs having an amino acid sequence that is at least 60%, 70%, 75%, 80%, 85%, 90%, 95%, 96%, 97%, 98%, 99% or 100% identical to that comprised in the corresponding heavy chain CDR1-3 of 28H1. Alternatively or additionally, the targeting moiety may comprise light chain CDRs having an amino acid sequence that is at least 60%, 70%, 75%, 80%, 85%, 90%, 95%, 96%, 97%, 98%, 99% or 100% identical to that comprised in the corresponding light chain CDR1-3 of 28H1. For example, the targeting moiety may comprise a heavy chain variable region having an amino acid sequence that is at least 60%, 70%, 75%, 80%, 85%, 90%, 95%, 96%, 97%, 98%, 99% or 100% identical to that comprised in the corresponding heavy chain variable region of 28H1. For example, the targeting moiety may comprise a light chain variable region having an amino acid sequence that is at least 60%, 70%, 75%, 80%, 85%, 90%, 95%, 96%, 97%, 98%, 99% or 100% identical to that comprised in the corresponding light chain variable region of 28H1. For example, the targeting moiety may comprise a light chain having an amino acid sequence that is at least 60%, 70%, 75%, 80%, 85%, 90%, 95%, 96%, 97%, 98%, 99% or 100% identical to that comprised in the corresponding light chain of 28H1.

The heavy chain CDR 1-3 of 28H1 are as set forth in SEQ ID NO: 76 (CDR1), SEQ ID NO: 77 (CDR2), and SEQ ID NO: 78 (CDR3), respectively. The light chain CDR 1-3 of 28H1 are as set forth in SEQ ID NO: 72 (CDR1), SEQ ID NO: 73 (CDR2), and SEQ ID NO: 74 (CDR3), respectively. The heavy chain variable region of 28H1 is as set forth in SEQ ID NO: 79. The light chain variable region of 28H1 is as set forth in SEQ ID NO: 75.

For the immunoconjugate according to the present disclosure, the Fc domain may be an IgG Fc domain. The IgG may be selected from the group consisting of IgG1, IgG2, IgG3 and IgG4. In some embodiments, the IgG is a human IgG1, and the Fc domain is a human IgG1 Fc domain (wildtype or modified).

Figure 8:
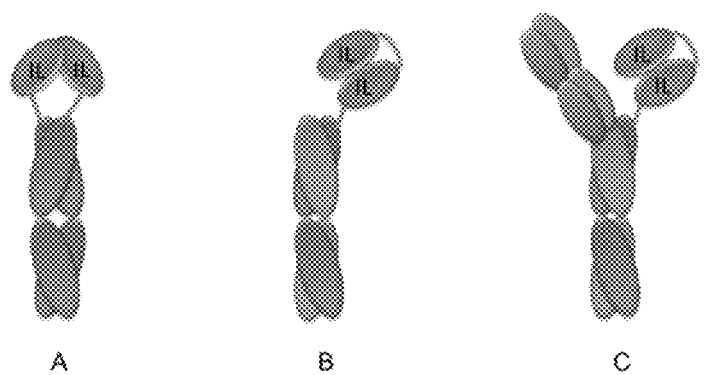
FIGS. 8A-8C illustrates examples of the immunoconjugate according to the present disclosure.

In some embodiments, the immunoconjugate is a proteinaceous homodimer consisting of two identical members. Each of the two identical members may comprise one or more interleukins (e.g., IL10) fused (e.g., in frame, such as via a peptide linker) to a subunit of the Fc domain. For example, the carboxy-terminal of the one or more interleukins may fuse to an amino-terminal amino acid of the Fc subunit. In some embodiments, the carboxy-terminal of one interleukin (e.g., IL10) is fused in frame to an amino-terminal amino acid of one of said two Fc subunits, to form one member of the homodimer, and two identical such members associate with each other via interactions between the two Fc subunits to form the homodimer (e.g., as illustrated in FIG. 8A). In some embodiments, two interleukins (e.g., two IL10) are fused in frame to each other (e.g., via a peptide linker) to form an interleukin dimer, and then, the carboxy-terminal of the interleukin dimer is fused in frame to an amino-terminal amino acid of one of said two Fc subunits, to form one member of the homodimer, and two identical such members associate with each other via interactions between the two Fc subunits to form the homodimer.

In some embodiments, the immunoconjugate is a proteinaceous heterodimer comprising a first member and a second member different from the first member, wherein the first member comprises the first Fc subunit, and the second member comprises the one or more interleukins fused to the second Fc subunit, and the first Fc subunit associates with the second Fc subunit to form the heterodimer.

In some embodiments, in the second member, at least one of the one or more interleukins is fused to the amino-terminal amino acid of the second Fc subunit.

In some embodiments, in the second member, at least two of the one or more interleukins are fused to each other to form an interleukin dimer, and the interleukin dimer is further fused to the amino-terminal amino acid of the second Fc subunit. For example, two IL10 may be fused in frame to each other (e.g., via a peptide linker, to form an IL10 dimer) and then fused in frame to the second Fc subunit, to form the second member of the proteinaceous heterodimer. For example, the carboxy-terminal of the IL10 dimer may be fused to an amino-terminal amino acid of the second Fc subunit (e.g., as illustrated in FIGS. 8B and 8C).

For example, the second member of the immunoconjugate may be a fusion protein, wherein the second Fc subunit may be fused in frame to the interleukin. In some embodiments, the carboxy-terminal of the interleukin(s) is directly or indirectly fused to an amino-terminal of the second Fc subunit to form the fusion protein. In some embodiments, the second Fc subunit is fused in frame to the interleukin(s) via a peptide linker.

A peptide linker according to the present disclosure may be a synthetic amino acid sequence that connects or links two polypeptide sequences, e.g., via peptide bonds. In some embodiments, a linker is a peptide comprising 1, 2, 3, 4, 5, 6, 7, 8, 9, 10, 11, 12, 13, 14, 15, 16, 17, 18, 19, 20, 21, 22, 23, 24, 25 or more amino acids. For example, the linker may comprise 1-10 amino acids (e.g., 1, 2, 3, 4, 5, 6, 7, 8, 9, 10 or more amino acids), 1-15 amino acids (e.g., 1-11, 12, 13, 14, 15 amino acids), 1-20 amino acids, 1-30 amino acids or more. In some embodiments, the linker comprises an amino acid sequence as set forth in SEQ ID NO: 41. In some embodiments, the linker is resistant to proteolysis or substantially resistant to proteolysis.

In some embodiments, the first member further comprises the targeting moiety fused to the first Fc subunit. For example, the targeting moiety may be fused to the amino-terminal amino acid of the first Fc subunit. For example, the first member may comprise a Fab moiety of an antibody, the carboxy-terminal of which (e.g., the carboxy-terminal of the heavy chain part, such as the CH1 domain or a hinge region) is fused to amino-terminal amino acid of the first Fc subunit (e.g., as illustrated in FIG. 8C).

In some embodiments, the proteinaceous heterodimer does not comprise any targeting moiety. For example, the first member may only comprise the first Fc subunit (e.g., as illustrated in FIG. 8B).

In some embodiments, the first Fc subunit is the same as the second Fc subunit (e.g., a subunit of a wildtype human IgG1 Fc domain).

In some embodiments, the first Fc subunit is different from the second Fc subunit, and the Fc domain comprises a modification promoting heterodimerization between the first Fc subunit and the second Fc subunit. For example, the first Fc subunit may comprise a first modification, and the second Fc subunit may comprise a second modification. For example, the first modification may be in a CH3 domain of the first Fc subunit, and the second modification may be in a CH3 domain of the second Fc subunit. For example, the first modification and/or the second modification is as compared to the sequence of its corresponding wildtype Fc domain, respectively For example, the first modification may comprise an amino acid substitution at position T366, and an amino acid substitution at one or more positions selected from the group consisting of: Y349, F405, K409, D399, K360, Q347, K392 and S354, wherein the position of the amino acid is determined according to the EU index of the KABAT number.

In some embodiments, the first modification comprises an amino acid substitution at position T366, and an amino acid substitution at one or more positions selected from the group consisting of: Y349, F405, K409, D399, K360, Q347, K392 and S354, wherein the position of the amino acid is determined according to the EU index of the KABAT number.

For example, the amino acid substitution comprised by the first modification may be selected from the group consisting of: Y349C, Y349D, D399S, F405K, K360E, K409A, K409E, Q347E, Q347R, S354D, K392D and T366W.

In some embodiments, the first modification comprises 2-5 amino acid substitutions.

In some embodiments, the first modification comprises an amino acid substitution at a group of positions selected from any of the following groups: 1) Y349 and T366; 2) Y349, T366 and F405; 3) Y349, T366 and K409; 4) Y349, T366, F405, K360 and Q347; 5) Y349, T366, F405 and Q347; 6) Y349, T366, K409, K360 and Q347; 7) Y349, T366, K409 and Q347; 8) T366, K409 and K392; 9) T366 and K409; 10) T366, K409, Y349 and S354; 11) T366 and F405; 12) T366, F405 and D399; and 13) T366, F405, Y349 and S354; wherein the position of the amino acid is determined according to the EU index of the KABAT number.

In some embodiments, the first modification comprises a group of amino acid substitutions selected from any of the following groups: 1) Y349C and T366W; 2) Y349C, T366W and F405K; 3) Y349C, T366W and K409E; 4) Y349C, T366W and K409A; 5) Y349C, T366W, F405K, K360E and Q347E; 6) Y349C, T366W, F405K and Q347R; 7) Y349C, T366W, K409A, K360E and Q347E; 8) Y349C, T366W, K409A and Q347R; 9) T366W, K409A and K392D; 10) T366W and K409A; 11) T366W, K409A and Y349D; 12) T366W, K409A, Y349D and S354D; 13) T366W and F405K; 14) T366W, F405K and D399S; 15) T366W, F405K and Y349D; and 16) T366W, F405K, Y349D and S354D; wherein the position of the amino acid is determined according to the EU index of the KABAT number.

In some embodiments, the second modification comprises amino acid substitutions at positions T366, L368 and Y407, as well as an amino acid substitution at one or more positions selected from the group consisting of D356, D399, E357, F405, K360, K392, K409 and Q347, wherein the position of the amino acid is determined according to the EU index of the KABAT number.

In some embodiments, the amino acid substitution comprised by the second modification is selected from the group consisting of D356C, D399S, E357A, F405K, K360E, K392D, K409A, L368A, L368G, Q347E, Q347R, T366S, Y407A and Y407V.

In some embodiments, the second modification comprises an amino acid substitution at 4-6 positions.

In some embodiments, the second modification comprises an amino acid substitution at a group of positions selected from any of the following groups: 1) D356, T366, L368, Y407 and F405; 2) D356, T366, L368 and Y407; 3) D356, T366, L368, Y407 and Q347; 4) D356, T366, L368, Y407, K360 and Q347; 5) D356, T366, L368, Y407, F405 and Q347; 6) D356, T366, L368, Y407, F405, K360 and Q347; 7) T366, L368, Y407, D399 and F405; 8) T366, L368, Y407 and F405; 9) T366, L368, Y407, F405 and E357; 10) T366, L368, Y407 and K409; 11) T366, L368, Y407, K409 and K392; and 12) T366, L368, Y407, K409 and E357; wherein the position of the amino acid is determined according to the EU index of the KABAT number.

In some embodiments, the second modification comprises a group of amino acid substitutions selected from any of the following groups: 1) D356C, T366S, L368A, Y407V and F405K; 2) D356C, T366S, L368A and Y407V; 3) D356C, T366S, L368A, Y407V and Q347R; 4) D356C, T366S, L368A, Y407V, K360E and Q347E; 5) D356C, T366S, L368A, Y407V, F405K and Q347R; 6) D356C, T366S, L368A, Y407V, F405K, K360E and Q347E; 7) T366S, L368A, Y407V, D399S and F405K; 8) T366S, L368G, Y407A and F405K; 9) T366S, L368A, Y407V, F405K and E357A; 10) T366S, L368A, Y407V and K409A; 11) T366S, L368A, Y407V, K409A and K392D; 12) T366S, L368G, Y407A and K409A; 13) T366S, L368A, Y407V, K409A and E357A; wherein the position of the amino acid is determined according to the EU index of the KABAT number.

In some embodiments, the first Fc subunit comprises the first modification, the second Fc subunit comprises the second modification, and the first modification and the second modification comprise an amino acid substitution at a group of positions selected from any of the following groups: 1) the first modification: Y349 and T366; and the second modification: D356, T366, L368, Y407 and F405; 2) the first modification: Y349, T366 and F405; and the second modification: D356, T366, L368 and Y407; 3) the first modification: Y349, T366 and K409; and the second modification: D356, T366, L368, Y407 and F405; 4) the first modification: Y349, T366, F405, K360 and Q347; and the second modification: D356, T366, L368, Y407 and Q347; 5) the first modification: Y349, T366, F405 and Q347; and the second modification: D356, T366, L368, Y407, K360 and Q347; 6) the first modification: Y349, T366, K409, K360 and Q347; and the second modification: D356, T366, L368, Y407, F405 and Q347; 7) the first modification: Y349, T366, K409 and Q347; and the second modification: D356, T366, L368, Y407, F405, K360 and Q347; 8) the first modification: T366, K409 and K392; and the second modification: T366, L368, Y407, D399 and F405; 9) the first modification: T366 and K409; and the second modification: T366, L368, Y407 and F405; 10) the first modification: T366, K409 and Y349; and the second modification: T366, L368, Y407, F405 and E357; 11) the first modification: T366, K409, Y349 and S354; and the second modification: T366, L368, Y407, F405 and E357; 12) the first modification: T366 and F405; and the second modification: T366, L368, Y407 and K409; 13) the first modification: T366, F405 and D399; and the second modification: T366, L368, Y407, K409 and K392; 14) the first modification: T366, F405 and Y349; and the second modification: T366, L368, Y407, K409 and E357; 15) the first modification: T366, F405, Y349 and S354; and the second modification: T366, L368, Y407, K409 and E357; wherein the position of the amino acid is determined according to the EU index of the KABAT number.

In some embodiments, the first Fc subunit comprises the first modification, the second Fc subunit comprises the second modification, wherein the first modification and the second modification comprise a group of amino acid substitutions selected from any of the following groups: 1) the first modification: Y349C and T366W; and the second modification: D356C, T366S, L368A, Y407V and F405K; 2) the first modification: Y349C, T366W and F405K; and the second modification: D356C, T366S, L368A and Y407V; 3) the first modification: Y349C, T366W and K409E; and the second modification: D356C, T366S, L368A, Y407V and F405K; 4) the first modification: Y349C, T366W and K409A; and the second modification: D356C, T366S, L368A, Y407V and F405K; 5) the first modification: Y349C, T366W, F405K, K360E and Q347E; and the second modification: D356C, T366S, L368A, Y407V and Q347R; 6) the first modification: Y349C, T366W, F405K and Q347R; and the second modification: D356C, T366S, L368A, Y407V, K360E and Q347E; 7) the first modification: Y349C, T366W, K409A, K360E and Q347E; and the second modification: D356C, T366S, L368A, Y407V, F405K and Q347R; 8) the first modification: Y349C, T366W, K409A and Q347R; and the second modification: D356C, T366S, L368A, Y407V, F405K, K360E and Q347E; 9) the first modification: T366W, K409A and K392D; and the second modification: T366S, L368A, Y407V, D399S and F405K; 10) the first modification: T366W and K409A; and the second modification: T366S, L368G, Y407A and F405K; 11) the first modification: T366W, K409A and Y349D; and the second modification: T366S, L368A, Y407V, F405K and E357A; 12) the first modification: T366W, K409A, Y349D and S354D; and the second modification: T366S, L368A, Y407V, F405K and E357A; 13) the first modification: T366W and F405K; and the second modification: T366S, L368A, Y407V and K409A; 14) the first modification: T366W, F405K and D399S; and the second modification: T366S, L368A, Y407V, K409A and K392D; the first modification: T366W and F405K; and the second modification: T366S, L368G, Y407A and K409A; 16) the first modification: T366W, F405K and Y349D; and the second modification: T366S, L368A, Y407V, K409A and E357A; 17) the first modification: T366W, F405K, Y349D and S354D; and the second modification: T366S, L368A, Y407V, K409A and E357A; wherein the position of the amino acid is determined according to the EU index of the KABAT number.

In some embodiments, the first Fc subunit comprises the first modification, the second Fc subunit comprises the second modification, the first modification comprises the amino acid substitutions T366W and K409A, and the second modification comprises the amino acid substitutions T366S, L368G, Y407A and F405K, wherein the position of the amino acid is determined according to the EU index of the KABAT number.

For example, the amino acid sequence of the first Fc subunit may be selected from SEQ ID NO: 39, 43 or 47. The amino acid sequence of the interleukin may be as set forth in SEQ ID NO: 50 or 52. The amino acid sequence of the second Fc subunit may be selected from SEQ ID NO: 50.

In some embodiments, the immunoconjugate of the present disclosure is the proteinaceous heterodimer, and the amino acid sequence of the second member may be selected from SEQ ID NO: 50.

The cytotoxic agent capable of inducing immunogenic cell death may be selected from the group consisting of: an alkylating agent, an antimetabolite, an anthracycline, a plant alkaloid, a platinum-based compound and a radiation agent or radiation therapy.

In some embodiments, the cytotoxic agent or cytotoxic therapy capable of inducing immunogenic cell death comprises an alkylating agent selected from cyclophosphamide.

In some embodiments, the cytotoxic agent or cytotoxic therapy capable of inducing immunogenic cell death comprises a platinum-based compound selected from the group consisting of: carboplatin, cisplatin and oxaliplatin.

In some embodiments, the cytotoxic agent capable of inducing immunogenic cell death comprises an antimetabolite selected from the group consisting of: capecitabine, gemcitabine, pemetrexed and 5-Fu.

In some embodiments, the cytotoxic agent capable of inducing immunogenic cell death comprises an anthracycline selected from the group consisting of: bleomycin, doxorubicin, epirubicin, daunorubicin, idarubicin, valrubicin and mitomycin-C. In some embodiments, the cytotoxic agent or cytotoxic therapy capable of inducing immunogenic cell death comprises doxorubicin.

In some embodiments, the cytotoxic agent capable of inducing immunogenic cell death comprises a plant alkaloid selected from the group consisting of: taxane, docetaxel, paclitaxel, vinblastine, vincristine and vinorelbine.

The radiation agent may be an agent (e.g., is or comprises a radioisotope) capable of emitting X-ray radiation and/or gamma-ray radiation.

In some embodiments, the radiation agent is capable of emitting at least one dose of X-ray radiation. Each dose of the X-ray radiation may be with a dosage of about 50 Gy or lower (e.g., about 45 Gy or lower, about 40 Gy or lower, about 35 Gy or lower, about 30 Gy or lower, about 25 Gy or lower, about 20 Gy or lower, about 15 Gy or lower, about 14 Gy or lower, about 13 Gy or lower, about 12 Gy or lower, about 11 Gy or lower, about 10 Gy or lower, about 9 Gy or lower, about 8 Gy or lower, about 7 Gy or lower, about 6 Gy or lower, about 5 Gy or lower, or about 4 Gy or lower). In some embodiments, each dose of the X-ray radiation is with a dosage of about 6-15 Gy, such as 6-14 Gy, 6-13 Gy, 6-12 Gy, 6-11 Gy, 6-10 Gy, 6-9 Gy, 6-8 Gy, 6-7 Gy, 7-15 Gy, 7-14 Gy, 7-13 Gy, 7-12 Gy, 7-11 Gy, 7-10 Gy, 7-9 Gy, or 7-8 Gy.

In some embodiments, the radiation agent is capable of emitting at least one dose of gamma-ray radiation. Each dose of the gamma-ray radiation may be with a dosage of about 50 Gy or lower (e.g., about 45 Gy or lower, about 40 Gy or lower, about 35 Gy or lower, about 30 Gy or lower, about 25 Gy or lower, about 20 Gy or lower, about 15 Gy or lower, about 14 Gy or lower, about 13 Gy or lower, about 12 Gy or lower, about 11 Gy or lower, about 10 Gy or lower, about 9 Gy or lower, about 8 Gy or lower, about 7 Gy or lower, about 6 Gy or lower, about 5 Gy or lower, or about 4 Gy or lower). In some embodiments, each dose of the gamma-ray radiation is with a dosage of about 6-15 Gy, such as 6-14 Gy, 6-13 Gy, 6-12 Gy, 6-11 Gy, 6-10 Gy, 6-9 Gy, 6-8 Gy, 6-7 Gy, 7-15 Gy, 7-14 Gy, 7-13 Gy, 7-12 Gy, 7-11 Gy, 7-10 Gy, 7-9 Gy, or 7-8 Gy.

In some embodiments, the radiation agent is capable of emitting about 2-15 doses (or fractions) (e.g., at least 2 doses, at least 3 doses, at least 4 doses, at least 5 doses, at least 6 doses, at least 7 doses, at least 8 doses, at least 9 doses, at least 10 doses, at least 11 doses, at least 12 doses or more, for example, 2-14 doses, 2-13 doses, 2-12 doses, 2-11 doses, 2-10 doses, 2-9 doses, 2-8 doses, 2-7 doses, 2-6 doses, 2-5 doses, 2-4 doses, 3-8 doses, 3-7 doses, or 4-10 doses) of X-ray radiation or gamma-ray radiation.

Different components of the composition may be independently packaged (e.g., not mixed from each other before administration) or pre-mixed and packaged in the same packaging unit.

The composition of the present disclosure may be a pharmaceutical composition and may further comprise a pharmaceutically acceptable excipient. Examples of pharmaceutically acceptable excipients include, but are not limited to inert solid diluents and fillers, diluents, sterile aqueous solution and various organic solvents, permeation enhancers, solubilizers and adjuvants.

In some embodiments, the pharmaceutical composition is formulated for oral administration, intravenous administration, intramuscular administration, in-situ administration at the site of a tumor, inhalation, rectal administration, vaginal administration, transdermal administration, or administration via subcutaneous repository.

The compositions of the present disclosure may comprise a therapeutically effective amount of the active agent (e.g., the immunoconjugate and the cytotoxic agent). A therapeutically effective amount is an amount of the subject composition capable of preventing and/or curing (at least partially) a condition or disorder (e.g., cancer) and/or any complications thereof in a subject suffering from or having a risk of developing said condition or disorder. The specific amount/concentration of the active agent comprised may vary according to the method of administration and the need of a patient, and can be determined based on e.g., volume, viscosity, and/or body weight of a patient etc.

Method and Use for Cancer Treatment

In another aspect, the present disclosure provides a immunoconjugate for the use of treating cancer in combination with a cytotoxic therapy. The immunoconjugate may comprise 1) one or more interleukins, and 2) an Fc domain consisting of a first Fc subunit and a second Fc subunit, and the first Fc subunit associates with the second Fc subunit to form a dimer. The one or more interleukins may be fused to the Fc domain. The cytotoxic agent may be capable of inducing immunogenic cell death.

In another aspect, the present disclosure provides a use of a immunoconjugate in combination with a cytotoxic therapy in the preparation of a medicament for treating cancer in a subject in need thereof. The immunoconjugate may comprise 1) one or more interleukins, and 2) an Fc domain consisting of a first Fc subunit and a second Fc subunit, and the first Fc subunit associates with the second Fc subunit to form a dimer. The one or more interleukins may be fused to the Fc domain. The cytotoxic agent may be capable of inducing immunogenic cell death.

In a further aspect, the present disclosure provides a method for treating cancer in a subject in need thereof. The method comprises administering to the subject an effective amount of (a) an immunoconjugate in combination with an effective dose of (b) a cytotoxic therapy. The immunoconjugate may comprise 1) one or more interleukins, and 2) an Fc domain consisting of a first Fc subunit and a second Fc subunit, and the first Fc subunit associates with the second Fc subunit to form a dimer. The one or more interleukins may be fused to the Fc domain. The cytotoxic agent may be capable of inducing immunogenic cell death.

The immunoconjugate is as defined in other parts of the present disclosure. For example, the immunoconjugate may be that comprised in the composition of the present disclosure.

The cytotoxic therapy capable of inducing immunogenic cell death may be selected from the group consisting of: an alkylating agent, an antimetabolite, an anthracycline, a plant alkaloid, a platinum-based compound and a radiation agent or radiation therapy.

In some embodiments, the cytotoxic therapy capable of inducing immunogenic cell death comprises an alkylating agent selected from the group consisting of: cyclophosphamide.

In some embodiments, the cytotoxic therapy capable of inducing immunogenic cell death comprises an antimetabolite selected from the group consisting of: capecitabine, gemcitabine, pemetrexed and 5-Fu.

In some embodiments, the cytotoxic therapy capable of inducing immunogenic cell death comprises an anthracycline selected from the group consisting of: bleomycin, doxorubicin, epirubicin, daunorubicin, idarubicin, valrubicin and mitomycin-C. In some embodiments, the cytotoxic agent or cytotoxic therapy capable of inducing immunogenic cell death comprises doxorubicin.

In some embodiments, the cytotoxic therapy capable of inducing immunogenic cell death comprises a plant alkaloid selected from the group consisting of: taxane, docetaxel, paclitaxel, vinblastine, vincristine and vinorelbine.

In some embodiments, the cytotoxic therapy capable of inducing immunogenic cell death comprises a platinum-based compound selected from the group consisting of: carboplatin, cisplatin and oxaliplatin.

In some embodiments, the cytotoxic therapy capable of inducing immunogenic cell death comprises at least one dose of radiation therapy. The radiation therapy may comprise X-ray radiation and/or gamma-ray radiation. The radiation therapy may be fractionated radiation therapy, e.g., radiation therapy administered in multiple doses or as multiple fractions.

Each dose or fraction of the X-ray radiation may be with a dosage of about 50 Gy or lower (e.g., about 45 Gy or lower, about 40 Gy or lower, about 35 Gy or lower, about 30 Gy or lower, about 25 Gy or lower, about 20 Gy or lower, about 15 Gy or lower, about 14 Gy or lower, about 13 Gy or lower, about 12 Gy or lower, about 11 Gy or lower, about 10 Gy or lower, about 9 Gy or lower, about 8 Gy or lower, about 7 Gy or lower, about 6 Gy or lower, about 5 Gy or lower, or about 4 Gy or lower). In some embodiments, each dose or fraction of the X-ray radiation is with a dosage of about 6-15 Gy, such as 6-14 Gy, 6-13 Gy, 6-12 Gy, 6-11 Gy, 6-10 Gy, 6-9 Gy, 6-8 Gy, 6-7 Gy, 7-15 Gy, 7-14 Gy, 7-13 Gy, 7-12 Gy, 7-11 Gy, 7-10 Gy, 7-9 Gy, or 7-8 Gy.

In some embodiments, a single dose of radiation therapy is used and the radiation is an X-ray radiation or gamma-ray radiation with a dosage of about 5-15 Gy (e.g., 6-15 Gy, 7-Gy, 7-10 Gy or 6-12 Gy). In some embodiments, 4-10 doses or fractions of radiation therapy are used and the radiation is an X-ray radiation (e.g., fractionated X-ray radiation) or gamma-ray radiation (e.g., fractionated gamma-ray radiation), with each dose comprising a dosage of about 5-15 Gy (e.g., 6-15 Gy, 7-15 Gy, 7-10 Gy or 6-12 Gy).

In some embodiments, more than one dose (e.g., at least two doses, at least 3 doses, at least 4 doses, at least 5 doses, at least 6 doses, at least 7 doses, at least 8 doses, at least 9 doses, at least 10 doses, at least 11 doses, at least 12 doses or more) of the cytotoxic therapy may be administered to the subject. For example, 2-15 doses, 2-14 doses, 2-13 doses, 2-12 doses, 2-11 doses, 2-10 doses, 2-9 doses, 2-8 doses, 3-10 doses, 4-10 doses, or 4-12 doses of the cytotoxic therapy may be administered to the subject.

The immunoconjugate may be administered to the subject subsequent to the administration of the cytotoxic therapy. In some embodiments, more than one dose of the cytotoxic therapy is administered to the subject, and the immunoconjugate is administered to the subject subsequent to the administration of the last (or final) dose of the cytotoxic therapy.

For example, 2-15 doses (e.g., 2-14 doses, 2-13 doses, 2-12 doses, 2-11 doses, 2-10 doses, 2-9 doses, 2-8 doses, 3-10 doses, 4-10 doses, or 4-12 doses) of the cytotoxic therapy may be administered to the subject, and the immunoconjugate may be administered to the subject subsequent to the administration of the last (or final) dose of the cytotoxic therapy.

The immunoconjugate may be administered to the subject no more than 10 days (e.g., no more than 9 days, no more than 8 days, no more than 7 days, no more than 6 days, no more than 5 days, no more than 4 days, no more than 3 days, no more than 2 days, no more than 1 day or immediately) after the administration of the cytotoxic therapy (for example, after administration of the last dose of the cytotoxic agent). In some embodiments, the immunoconjugate is administered to the subject 0-7 days (e.g., 0-6 days, 0-5 days, 0-4 days, 0-3 days, 0-2 days, or 0-1 day) after the administration of the cytotoxic therapy.

The immunoconjugate may be administered to the subject for two or more times (e.g., at least 2 times, at least 3 times, at least 4 times or more).

The cancer may comprise a solid tumor. For example, the cancer may be selected from the group consisting of a B cell lymphoma, a lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma.

In some embodiments, the cancer is within the body of a subject, e.g., a cancer or cancer cell within a human or in a non-human animal (e.g., a mammal). In some embodiments, the mammal is a human. In some embodiments, the mammal is a mouse, a rat, a cat, a dog, a rabbit, a pig, a sheep, a horse, a bovine, a goat, a gerbil, a hamster, a guinea pig, a monkey or any other mammal. Many such mammals may be subjects that are known to the art as preclinical models for certain diseases or disorders, including solid tumors and/or other cancers (e.g., Talmadge et al., 2007 *Am. J. Pathol.* 170:793; Kerbel, 2003 *Canc. Biol. Therap.* 2(4 Suppl 1): S134; Man et al., 2007 *Canc. Met. Rev.* 26:737; Cespedes et al., 2006 *Clin. TransL Oncol.* 8:318).

The present disclosure also includes the following embodiments:

1. A composition comprising an immunoconjugate and a cytotoxic agent, wherein: said immunoconjugate comprises 1) one or more interleukins, and 2) an Fc domain consisting of a first Fc subunit and a second Fc subunit, said first Fc subunit associates with said second Fc subunit to form a dimer; said one or more interleukins are fused to said Fc domain; and wherein said cytotoxic agent is capable of inducing immunogenic cell death.

2. The composition according to embodiment 1, wherein at least one of said one or more interleukins is fused to an amino-terminal amino acid of said Fc domain.

3. The composition according to any one of embodiments 1-2, wherein said immunoconjugate comprises two or more interleukins.

4. The composition according to embodiment 3, wherein at least two of said two or more interleukins are fused to an amino-terminal amino acid of said Fc domain.

5. The composition according to any one of embodiments 1-4, wherein one or more of said interleukins is fused to said Fc domain through a peptide linker.

6. The composition according to any one of embodiments 3-5, wherein at least two of said two or more interleukins are fused to each other through a peptide linker to form an interleukin dimer.

7. The composition according to embodiment 6, wherein at least one said interleukin dimer is fused to an amino-terminal amino acid of said Fc domain.

8. The composition according to any one of embodiments 3-7, wherein said two or more interleukins are two or more copies of the same interleukin.

9. The composition according to embodiment 8, wherein said two or more interleukins are two or more copies of IL10.

10. The composition according to any one of embodiments 1-9, wherein said immunoconjugate further comprises a targeting moiety fused to said Fc domain, wherein said targeting moiety exhibits binding specificity to a tumor antigen.

11. The composition according to embodiment 10, wherein said targeting moiety is fused to an amino-terminal amino acid of said Fc domain.

12. The composition according to any one of embodiments 10-11 wherein said targeting moiety is fused to said Fc domain through a peptide linker or an immunoglobulin hinge region.

13. The composition according to any one of embodiments 10-12, wherein said targeting moiety comprises an antigen binding domain of an antibody.

14. The composition according to embodiment 13, wherein said antigen binding domain of an antibody is a Fab moiety.

15. The composition according to any one of embodiments 10-14, wherein said tumor antigen is selected from the group consisting of: EGFR, HER2/neu, and FAP.

16. The composition according to any one of embodiments 10-15, wherein said targeting moiety comprises an antigen-binding domain of an antibody and said antibody is selected from the group consisting of: anti-EGFR antibody, anti-HER2 antibody and anti-FAP antibody.

17. The composition according to embodiment 16, wherein said antibody is an anti-EGFR antibody.

18. The composition according to embodiment 17, wherein said anti-EGFR antibody is cetuximab.

19. The composition according to embodiment 18, wherein said targeting moiety comprises the heavy chain CDR1-3 of cetuximab.

20. The composition according to any one of embodiments 18-19, wherein said targeting moiety comprises the light chain CDR1-3 of cetuximab.

21. The composition according to any one of embodiments 18-20, wherein said targeting moiety comprises the heavy chain variable region of cetuximab.

22. The composition according to any one of embodiments 18-21, wherein said targeting moiety comprises the light chain variable region of cetuximab.

23. The composition according to embodiment 16, wherein said antibody is an anti-HER2 antibody.

24. The composition according to embodiment 23, wherein said anti-HER2 antibody is Trastuzumab.

25. The composition according to embodiment 24, wherein said targeting moiety comprises the heavy chain CDR1-3 of Trastuzumab.

26. The composition according to any one of embodiments 24-25, wherein said targeting moiety comprises the light chain CDR1-3 of Trastuzumab.

27. The composition according to any one of embodiments 24-26, wherein said targeting moiety comprises the heavy chain variable region of Trastuzumab.

28. The composition according to any one of embodiments 24-27, wherein said targeting moiety comprises the light chain variable region of Trastuzumab.

29. The composition according to embodiment 16, wherein said antibody is an anti-FAP antibody.

30. The composition according to embodiment 29, wherein said anti-FAP antibody is 28H1.

31. The composition according to embodiment 30, wherein said targeting moiety comprises the heavy chain CDR1-3 of 28H1.

32. The composition according to any one of embodiments 30-31, wherein said targeting moiety comprises the light chain CDR1-3 of 28H1.

33. The composition according to any one of embodiments 30-32, wherein said targeting moiety comprises the heavy chain variable region of 28H1.

34. The composition according to any one of embodiments 30-33, wherein said targeting moiety comprises the light chain variable region of 28H1.

35. The composition according to any one of embodiments 1-34, wherein said Fc domain is an IgG Fc domain.

36. The composition according to embodiment 35, wherein said IgG is selected from the group consisting of IgG1, IgG2, IgG3 and IgG4.

37. The composition according to embodiment 36, wherein said IgG is a human IgG1.

38. The composition according to any one of embodiments 1-37, wherein said immunoconjugate is a immunoconjugate comprising a first member and a second member different from said first member, wherein said first member comprises said first Fc subunit, and said second member comprises said one or more interleukins fused to said second Fc subunit, and said first Fc subunit associates with said second Fc subunit to form said heterodimer.

39. The composition according to embodiment 38, wherein in said second member, at least one of said one or more interleukins is fused to the amino-terminal amino acid of said second Fc subunit.

40. The composition according to embodiment 39, wherein in said second member, at least two of said one or more interleukins are fused to each other to form an interleukin dimer, and said interleukin dimer is further fused to the amino-terminal amino acid of said second Fc subunit.

41. The composition according to any one of embodiments 38-40, wherein said first member further comprises said targeting moiety fused to said first Fc subunit.

42. The composition according to embodiment 41, wherein in said first member, said targeting moiety is fused to the amino-terminal amino acid of said first Fc subunit.

43. The composition according to any one of embodiments 38-40, wherein said immunoconjugate does not comprise any targeting moiety.

44. The composition according to any one of embodiments 1-43, wherein said first Fc subunit is different from said second Fc subunit, and said Fc domain comprises a modification promoting heterodimerization between said first Fc subunit and said second Fc subunit.

45. The composition according to embodiment 44, wherein said first Fc subunit comprises a first modification, and said second Fc subunit comprises a second modification.

46. The composition according to embodiment 45, wherein said first modification comprises an amino acid substitution at position T366, and an amino acid substitution at one or more positions selected from the group consisting of: Y349, F405, K409, D399, K360, Q347, K392 and S354, wherein the position of the amino acid is determined according to the EU index of the KABAT number.

47. The composition according to embodiment 46, wherein the amino acid substitution comprised by the first modification is selected from the group consisting of: Y349C, Y349D, D399S, F405K, K360E, K409A, K409E, Q347E, Q347R, S354D, K392D and T366W.

48. The composition according to any one of embodiments 45-47, wherein said first modification comprises 2-5 amino acid substitutions.

49. The composition according to any one of embodiments 45-48, wherein said first modification comprises an amino acid substitution at a group of positions selected from any of the following groups: 1) Y349 and T366; 2) Y349, T366 and F405; 3) Y349, T366 and K409; 4) Y349, T366, F405, K360 and Q347; 5) Y349, T366, F405 and Q347; 6) Y349, T366, K409, K360 and Q347; 7) Y349, T366, K409 and Q347; 8) T366, K409 and K392; 9) T366 and K409; T366, K409, Y349 and S354; 11) T366 and F405; 12) T366, F405 and D399; and 13) T366, F405, Y349 and S354; wherein the position of the amino acid is determined according to the EU index of the KABAT number.

50. The composition according to any one of embodiments 45-49, wherein said first modification comprises a group of amino acid substitutions selected from any of the following groups: 1) Y349C and T366W; 2) Y349C, T366W and F405K; 3) Y349C, T366W and K409E; 4) Y349C, T366W and K409A; 5) Y349C, T366W, F405K, K360E and Q347E; 6) Y349C, T366W, F405K and Q347R; 7) Y349C, T366W, K409A, K360E and Q347E; 8) Y349C, T366W, K409A and Q347R; 9) T366W, K409A and K392D; 10) T366W and K409A; 11) T366W, K409A and Y349D; 12) T366W, K409A, Y349D and S354D; 13) T366W and F405K; 14) T366W, F405K and D399S; 15) T366W, F405K and Y349D; and 16) T366W, F405K, Y349D and S354D; wherein the position of the amino acid is determined according to the EU index of the KABAT number.

51. The composition according to any one of embodiments 45-50, wherein said second modification comprises amino acid substitutions at positions T366, L368 and Y407, as well as an amino acid substitution at one or more positions selected from the group consisting of D356, D399, E357, F405, K360, K392, K409 and Q347, wherein the position of the amino acid is determined according to the EU index of the KABAT number.

52. The composition according to embodiment 51, wherein the amino acid substitution comprised by the second modification is selected from the group consisting of D356C, D399S, E357A, F405K, K360E, K392D, K409A, L368A, L368G, Q347E, Q347R, T366S, Y407A and Y407V.

53. The composition according to any one of embodiments 45-52, wherein the second modification comprises an amino acid substitution at 4-6 positions.

54. The composition according to any one of embodiments 45-53, wherein the second modification comprises an amino acid substitution at a group of positions selected from any of the following groups: 1) D356, T366, L368, Y407 and F405; 2) D356, T366, L368 and Y407; 3) D356, L368, Y407 and Q347; 4) D356, T366, L368, Y407, K360 and Q347; D356, T366, L368, Y407, F405 and Q347; 6) D356, T366, L368, Y407, F405, K360 and Q347; 7) T366, L368, Y407, D399 and F405; 8) T366, L368, Y407 and F405; 9) T366, L368, Y407, F405 and E357; 10) T366, L368, Y407 and K409; 11) T366, L368, Y407, K409 and K392; and 12) T366, L368, Y407, K409 and E357; wherein the position of the amino acid is determined according to the EU index of the KABAT number.

55. The composition according to any one of embodiments 45-54, wherein the second modification comprises a group of amino acid substitutions selected from any of the following groups: 1) D356C, T366S, L368A, Y407V and F405K; 2) D356C, T366S, L368A and Y407V; 3) D356C, T366S, L368A, Y407V and Q347R; 4) D356C, T366S, L368A, Y407V, K360E and Q347E; 5) D356C, T366S, L368A, Y407V, F405K and Q347R; 6) D356C, T366S, L368A, Y407V, F405K, K360E and Q347E; 7) T366S, L368A, Y407V, D399S and F405K; 8) T366S, L368G, Y407A and F405K; 9) T366S, L368A, Y407V, F405K and E357A; T366S, L368A, Y407V and K409A; 11) T366S, L368A, Y407V, K409A and K392D; 12) T366S, L368G, Y407A and K409A; 13) T366S, L368A, Y407V, K409A and E357A; wherein the position of the amino acid is determined according to the EU index of the KABAT number.

56. The composition according to any one of embodiments 45-55, wherein the first Fc subunit comprises the first modification, the second Fc subunit comprises the second modification, and the first modification and the second modification comprise an amino acid substitution at a group of positions selected from any of the following groups: 1) the first modification: Y349 and T366; and the second modification: D356, T366, L368, Y407 and F405; 2) the first modification: Y349, T366 and F405; and the second modification: D356, T366, L368 and Y407; 3) the first modification: Y349, T366 and K409; and the second modification: D356, T366, L368, Y407 and F405; 4) the first modification: Y349, T366, F405, K360 and Q347; and the second modification: D356, T366, L368, Y407 and Q347; 5) the first modification: Y349, T366, F405 and Q347; and the second modification: D356, T366, L368, Y407, K360 and Q347; 6) the first modification: Y349, T366, K409, K360 and Q347; and the second modification: D356, T366, L368, Y407, F405 and Q347; 7) the first modification: Y349, T366, K409 and Q347; and the second modification: D356, T366, L368, Y407, F405, K360 and Q347; 8) the first modification: T366, K409 and K392; and the second modification: T366, L368, Y407, D399 and F405; 9) the first modification: T366 and K409; and the second modification: T366, L368, Y407 and F405; 10) the first modification: T366, K409 and Y349; and the second modification: T366, L368, Y407, F405 and E357; 11) the first modification: T366, K409, Y349 and S354; and the second modification: T366, L368, Y407, F405 and E357; 12) the first modification: T366 and F405; and the second modification: T366, L368, Y407 and K409; 13) the first modification: T366, F405 and D399; and the second modification: T366, L368, Y407, K409 and K392; 14) the first modification: T366, F405 and Y349; and the second modification: T366, L368, Y407, K409 and E357; 15) the first modification: T366, F405, Y349 and S354; and the second modification: T366, L368, Y407, K409 and E357; wherein the position of the amino acid is determined according to the EU index of the KABAT number.

57. The composition according to any one of embodiments 45-56, wherein the first Fc subunit comprises the first modification, the second Fc subunit comprises the second modification, wherein the first modification and the second modification comprise a group of amino acid substitutions selected from any of the following groups: 1) the first modification: Y349C and T366W; and the second modification: D356C, T366S, L368A, Y407V and F405K; 2) the first modification: Y349C, T366W and F405K; and the second modification: D356C, T366S, L368A and Y407V; 3) the first modification: Y349C, T366W and K409E; and the second modification: D356C, T366S, L368A, Y407V and F405K; 4) the first modification: Y349C, T366W and K409A; and the second modification: D356C, T366S, L368A, Y407V and F405K; 5) the first modification: Y349C, T366W, F405K, K360E and Q347E; and the second modification: D356C, T366S, L368A, Y407V and Q347R; 6) the first modification: Y349C, T366W, F405K and Q347R; and the second modification: D356C, T366S, L368A, Y407V, K360E and Q347E; 7) the first modification: Y349C, T366W, K409A, K360E and Q347E; and the second modification: D356C, T366S, L368A, Y407V, F405K and Q347R; 8) the first modification: Y349C, T366W, K409A and Q347R; and the second modification: D356C, T366S, L368A, Y407V, F405K, K360E and Q347E; 9) the first modification: T366W, K409A and K392D; and the second modification: T366S, L368A, Y407V, D399S and F405K; 10) the first modification: T366W and K409A; and the second modification: T366S, L368G, Y407A and F405K; 11) the first modification: T366W, K409A and Y349D; and the second modification: T366S, L368A, Y407V, F405K and E357A; 12) the first modification: T366W, K409A, Y349D and S354D; and the second modification: T366S, L368A, Y407V, F405K and E357A; 13) the first modification: T366W and F405K; and the second modification: T366S, L368A, Y407V and K409A; 14) the first modification: T366W, F405K and D399S; and the second modification: T366S, L368A, Y407V, K409A and K392D; 15) the first modification: T366W and F405K; and the second modification: T366S, L368G, Y407A and K409A; 16) the first modification: T366W, F405K and Y349D; and the second modification: T366S, L368A, Y407V, K409A and E357A; 17) the first modification: T366W, F405K, Y349D and S354D; and the second modification: T366S, L368A, Y407V, K409A and E357A; wherein the position of the amino acid is determined according to the EU index of the KABAT number.

58. The composition according to embodiment 57, wherein the first Fc subunit comprises the first modification, the second Fc subunit comprises the second modification, the first modification comprises the amino acid substitutions T366W and K409A, and the second modification comprises the amino acid substitutions T366S, L368G, Y407A and F405K, wherein the position of the amino acid is determined according to the EU index of the KABAT number.

59. The composition according to any one of embodiments 1-58, wherein said cytotoxic agent capable of inducing immunogenic cell death is selected from the group consisting of: an alkylating agent, an antimetabolite, an anthracycline, a plant alkaloid, a platinum-based compound, and a radiation agent.

60. The composition according to embodiment 59, wherein said cytotoxic agent capable of inducing immunogenic cell death comprises an alkylating agent selected from cyclophosphamide.

61. The composition according to embodiment 59, wherein said cytotoxic agent capable of inducing immunogenic cell death comprises an antimetabolite selected from the group consisting of: capecitabine, gemcitabine, pemetrexed and 5-Fu.

62. The composition according to embodiment 59, wherein said cytotoxic agent capable of inducing immunogenic cell death comprises an anthracycline selected from the group consisting of: bleomycin, doxorubicin and mitomycin-C.

63. The composition according to embodiment 59, wherein said cytotoxic agent capable of inducing immunogenic cell death comprises a plant alkaloid selected from the group consisting of: taxane, docetaxel, paclitaxel, vinblastine, vincristine and vinorelbine.

64. The composition according to embodiment 59, wherein said cytotoxic agent capable of inducing immunogenic cell death comprises a radiation agent that emits X-ray radiation and/or gamma-ray radiation.

65. The composition according to embodiment 64, wherein said radiation agent emits X-ray radiation, and each dose of the X-ray radiation is with a dosage of about 50 Gy or lower.

66. The composition according to embodiment 65, wherein said radiation agent emits gamma-ray radiation, and each dose of the gamma-ray radiation is with a dosage of about Gy or lower.

67. The composition according to embodiment 59, wherein said cytotoxic agent capable of inducing immunogenic cell death comprises a platinum-based compound selected from the group consisting of: carboplatin, cisplatin and oxaliplatin.

68. An immunoconjugate for the use of treating cancer in combination with a cytotoxic therapy, wherein said immunoconjugate is as defined in any one of embodiments 1-58, and said cytotoxic therapy is capable of inducing immunogenic cell death.

69. The immunoconjugate according to embodiment 68, wherein said cytotoxic therapy capable of inducing immunogenic cell death is selected from the group consisting of: an alkylating agent, an antimetabolite, an anthracycline, a plant alkaloid, a platinum-based compound and a radiation therapy.

70. The immunoconjugate according to embodiment 69, wherein said cytotoxic therapy capable of inducing immunogenic cell death comprises at least one dose of radiation therapy.

71. The immunoconjugate according to embodiment 70, wherein said radiation comprises X-ray radiation and/or gamma-ray radiation.

72. The immunoconjugate according to embodiment 71, wherein said radiation comprises X-ray radiation, and each dose of the X-ray radiation is with a dosage of about 50 Gy or lower.

73. The immunoconjugate according to embodiment 71, wherein said radiation comprises gamma-ray radiation, and each dose of the gamma-ray radiation is with a dosage of about 50 Gy or lower.

74. The immunoconjugate according to any one of embodiments 70-73, wherein said radiation therapy is fractionated radiation therapy.

75. The immunoconjugate according to embodiment 74, wherein said fractionated radiation therapy comprises 2-15 fractions.

76. The immunoconjugate according to embodiment 69, wherein said cytotoxic agent capable of inducing immunogenic cell death comprises an alkylating agent selected from cyclophosphamide.

77. The immunoconjugate according to embodiment 69, wherein said cytotoxic agent capable of inducing immunogenic cell death comprises an antimetabolite selected from the group consisting of: capecitabine, gemcitabine, pemetrexed and 5-Fu.

78. The immunoconjugate according to embodiment 69, wherein said cytotoxic agent capable of inducing immunogenic cell death comprises an anthracycline selected from the group consisting of: bleomycin, doxorubicin and mitomycin-C.

79. The immunoconjugate according to embodiment 69, wherein said cytotoxic agent capable of inducing immunogenic cell death comprises a plant alkaloid selected from the group consisting of: taxane, docetaxel, paclitaxel, vinblastine, vincristine and vinorelbine.

80. The immunoconjugate according to embodiment 69, wherein said cytotoxic agent capable of inducing immunogenic cell death comprises a platinum-based compound selected from the group consisting of: carboplatin, cisplatin and oxaliplatin.

81. Use of an immunoconjugate in combination with a cytotoxic therapy in the preparation of a medicament for treating cancer in a subject in need thereof, wherein said immunoconjugate is as defined in any one of embodiments 1-58, and said cytotoxic therapy is capable of inducing immunogenic cell death.

82. The use of embodiment 81, wherein said cytotoxic therapy capable of inducing immunogenic cell death is selected from the group consisting of: an alkylating agent, an antimetabolite, an anthracycline, a plant alkaloid, a platinum-based compound and a radiation therapy.

83. The use according to embodiment 82, wherein said cytotoxic therapy capable of inducing immunogenic cell death comprises at least one dose of radiation therapy.

84. The use according to embodiment 83, wherein said radiation therapy comprises X-ray radiation and/or gamma-ray radiation.

85. The use according to embodiment 84, wherein said radiation comprises X-ray radiation, and each dose of the X-ray radiation is with a dosage of about 50 Gy or lower.

86. The use according to embodiment 84, wherein said radiation comprises gamma-ray radiation, and each dose of the gamma-ray radiation is with a dosage of about 50 Gy or lower.

87. The use according to any one of embodiments 83-86, wherein said radiation therapy is fractionated radiation therapy.

88. The use according to embodiment 87, wherein said fractionated radiation therapy comprises 2-15 fractions.

89. The use according to embodiment 82, wherein said cytotoxic agent capable of inducing immunogenic cell death comprises an alkylating agent selected from cyclophosphamide.

90. The use according to embodiment 82, wherein said cytotoxic agent capable of inducing immunogenic cell death comprises an antimetabolite selected from the group consisting of: capecitabine, gemcitabine, pemetrexed and 5-Fu.

91. The use according to embodiment 82, wherein said cytotoxic agent capable of inducing immunogenic cell death comprises an anthracycline selected from the group consisting of: bleomycin, doxorubicin and mitomycin-C.

92. The use according to embodiment 82, wherein said cytotoxic agent capable of inducing immunogenic cell death comprises a plant alkaloid selected from the group consisting of: taxane, docetaxel, paclitaxel, vinblastine, vincristine and vinorelbine.

93. The use according to embodiment 82, wherein said cytotoxic agent capable of inducing immunogenic cell death comprises a platinum-based compound selected from the group consisting of: carboplatin, cisplatin and oxaliplatin.

94. A method for treating cancer in a subject in need thereof, comprising administering to said subject an effective amount of (a) an immunoconjugate in combination with an effective dose of (b) a cytotoxic therapy, wherein said immunoconjugate is as defined in any one of embodiments 1-58, and said cytotoxic therapy is capable of inducing immunogenic cell death.

95. The method according to embodiment 94, wherein said immunoconjugate is administered to said subject subsequent to administration of said cytotoxic therapy.

96. The method according to embodiment 95, wherein said immunoconjugate is administered to said subject no more than 10 days after administration of said cytotoxic therapy.

97. The method according to any one of embodiments 95-96, wherein said immunoconjugate is administered to said subject no more than 3 days after administration of said cytotoxic therapy.

98. The method according to any one of embodiments 94-97, wherein said immunoconjugate is administered to said subject for two or more times.

99. The method according to any one of embodiments 94-98, wherein said cytotoxic therapy capable of inducing immunogenic cell death is selected from the group consisting of: an alkylating agent, an antimetabolite, an anthracycline, a plant alkaloid, a platinum-based compound and a radiation therapy.

100. The method according to embodiment 99, wherein said cytotoxic therapy capable of inducing immunogenic cell death comprises at least one dose of radiation therapy.

101. The method according to embodiment 100, wherein said radiation therapy comprises X-ray radiation and/or gamma-ray radiation.

102. The method according to embodiment 101, wherein said radiation comprises X-ray radiation, and each dose of the X-ray radiation is with a dosage of about 50 Gy or lower.

103. The method according to embodiment 101, wherein said radiation comprises gamma-ray radiation, and each dose of the gamma-ray radiation is with a dosage of about 50 Gy or lower.

104. The method according to any one of embodiments 100-103, wherein said radiation therapy is fractionated radiation therapy.

105. The method according to embodiment 104, wherein said fractionated radiation therapy comprises 2-15 fractions.

106. The method according to embodiment 99, wherein said cytotoxic agent capable of inducing immunogenic cell death comprises an alkylating agent selected from cyclophosphamide.

107. The method according to embodiment 99, wherein said cytotoxic agent capable of inducing immunogenic cell death comprises an antimetabolite selected from the group consisting of: capecitabine, gemcitabine, pemetrexed and 5-Fu.

108. The method according to embodiment 99, wherein said cytotoxic agent capable of inducing immunogenic cell death comprises an anthracycline selected from the group consisting of: bleomycin, doxorubicin and mitomycin-C.

109. The method according to embodiment 99, wherein said cytotoxic agent capable of inducing immunogenic cell death comprises a plant alkaloid selected from the group consisting of: taxane, docetaxel, paclitaxel, vinblastine, vincristine and vinorelbine.

110. The method according to embodiment 99, wherein said cytotoxic agent capable of inducing immunogenic cell death comprises a platinum-based compound selected from the group consisting of: carboplatin, cisplatin and oxaliplatin.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1 Modification and Preparation of Nucleic Acids 1.1 Fc Modifications

Amino acid modifications (e.g., amino acid substitutions) were made to the interface residues of human IgG1 Fc domain to obtain the following groups of modifications (as shown in table 1 below), chain A is also referred to as Fc9 or the first Fc subunit, and chain B is also referred to as Fc6 or the second Fc subunit in the present disclosure:

TABLE 1

Groups of amino acid modifications

| Group | Fc Chain | Modifications | SEQ ID NO |
|---|---|---|---|
| 1 | A | Y349C + T366W | 1 |
|  | B | D356C + T366S + L368A + Y407V + F405K | 2 |
| 2 | A | Y349C + T366W + F405K | 3 |
|  | B | D356C + T366S + L368A + Y407V | 4 |
| 3 | A | Y349C + T366W + K409E | 5 |
|  | B | D356C + T366S + L368A + Y407V + F405K | 2 |
| 4 | A | Y349C + T366W + K409A | 6 |
|  | B | D356C + T366S + L368A + Y407V + F405K | 2 |

TABLE 1-continued

Groups of amino acid modifications

| Group | Fc Chain | Modifications | SEQ ID NO |
|---|---|---|---|
| 5 | A | Y349C + T366W + F405K + K360E + Q347E | 7 |
|   | B | D356C + T366S + L368A + Y407V + Q347R | 8 |
| 6 | A | Y349C + T366W + F405K + Q347R | 9 |
|   | B | D356C + T366S + L368A + Y407V + K360E + Q347E | 10 |
| 7 | A | Y349C + T366W + K409A + K360E + Q347E | 11 |
|   | B | D356C + T366S + L368A + Y407V + F405K + Q347R | 12 |
| 8 | A | Y349C + T366W + K409A + Q347R | 13 |
|   | B | D356C + T366S + L368A + Y407V + F405K + K360E + Q347E | 14 |
| 9 | A | T366W + K409A + K392D | 15 |
|   | B | T366S + L368A + Y407V + D399S + F405K | 16 |
| 10 | A | T366W + K409A | 17 |
|    | B | T366S + L368G + Y407A + F405K | 18 |
| 11 | A | T366W + K409A + Y349D | 19 |
|    | B | T366S + L368A + Y407V + F405K + E357A | 20 |
| 12 | A | T366W + K409A + Y349D + S354D | 21 |
|    | B | T366S + L368A + Y407V + F405K + E357A | 20 |
| 13 | A | T366W + F405K | 22 |
|    | B | T366S + L368A + Y407V + K409A | 23 |
| 14 | A | T366W + F405K + D399S | 24 |
|    | B | T366S + L368A + Y407V + K409A + K392D | 25 |
| 15 | A | T366W + F405K | 22 |
|    | B | T366S + L368G + Y407A + K409A | 26 |
| 16 | A | T366W + F405K + Y349D | 27 |
|    | B | T366S + L368A + Y407V + K409A + E357A | 28 |
| 17 | A | T366W + F405K + Y349D + S354D | 29 |
|    | B | T366S + L368A + Y407V + K409A + E357A | 28 |

Subsequently, formation of heterodimer proteins comprising the groups of modifications listed in table 1 above were examined using a ScFv-Fc/Fc system, as explained in detail below.

First of all, human immunoglobulin gamma1 (IgG1) constant region amino acid sequence was obtained from the database Uniprot (P01857), to get wildtype human IgG1-Fc region amino acid sequence (SEQ ID NO: 30). The polynucleotide fragment encoding wild type human IgG1-Fc was obtained by RT-PCR from human PBMC total RNA (SEQ ID NO: 31, named as the Fc gene fragment). A polynucleotide fragment encoding a mouse kappaIII signal peptide (SEQ ID NO: 32) was added to the 5' end of the Fc gene by overlapping PCR, and then subcloned into the vector pcDNA4 (Invitrogen, Cat V86220), to obtain a recombinant expression vector for expressing human IgG1-Fc in mammalian cells.

A nucleic acid molecule encoding a ScFv-Fc fusion protein (SEQ ID NO:33) was synthesized, wherein the ScFv refers to an anti-HER2 single chain antibody, the amino acid sequence of the ScFv-Fc fusion protein is as set forth in SEQ ID NO: 34. The ScFv-Fc gene fragment was then subcloned into the vector pcDNA4 (Invitrogen, Cat V86220), to obtain a recombinant expression vector for expressing the ScFv-Fc fusion protein in mammalian cells.

In some cases, a polypeptide encoding a variable region of a camel single domain antibody (VhH) was fused to the N terminal of the Fc gene fragment to obtain a fusion gene fragment (as set forth in SEQ ID NO: 35) encoding the fusion protein VhH-Fc (as set forth in SEQ ID NO: 36). It was then subcloned into the vector pcDNA4 (Invitrogen, Cat V86220), to obtain a recombinant expression vector for expressing the fusion protein VhH-Fc in mammalian cells.

Then, the amino acid modifications as listed in table 1 above were respectively introduced into the ScFv-Fc (groups 1-17), the VhH-Fc (groups 9-12, 14, 15 and 17), and the Fc gene fragment (groups 1-8) by overlapping PCR, wherein chain A refers to the Fc subunit in ScFv-Fc and chain B refers to the independent Fc subunit or the Fc subunit in VhH-Fc. The gene fragments with amino acid modifications were respectively subcloned into the vector pcDNA4 (Invitrogen, Cat V86220), to obtain recombinant expression vectors for expressing the modified ScFv-Fc fusion proteins, the modified Fc proteins, and the modified VhH-Fc fusion proteins in mammalian cells.

Then, suspend-cultured HEK293 cells (ATCC CRL-1573) were transfected with the constructed expression vectors with PEI. For each group, the expression vector expressing the A chain (ScFv-Fc fusion protein) and that expressing the B chain (Fc protein or VhH-Fc fusion protein) were co-transfected at a ratio of 1:1. After culturing for 5-6 days, supernatant of the transient expression products was collected, and the expression products comprising corresponding protein heterodimers were preliminarily purified using ProteinA affinity chromatography. Each of the preliminarily purified expression products comprises the homodimer protein ScFv-Fc/ScFv-Fc, the homodimer protein Fc/Fc (or the homodimer protein VhH-Fc/VhH-Fc) and the heterodimer protein ScFv-Fc/Fc (or the heterodimer protein ScFv-Fc/VhH-Fc), present in various percentages, respectively. Since the molecular weight of these proteins (i.e., the homodimers and the heterodimers) are different, their corresponding percentage could be determined according to corresponding band intensities reflected on non-reduced SDS-PAGE gels. The intensities were quantified and the results are summarized in Tables 2-5 below.

TABLE 2

Percentage of homodimer proteins and heterodimer proteins in expression products

| Group | ScFv-Fc homodimer (%) | ScFv-Fc/Fc heterodimer (%) | Fc homodimer (%) |
|---|---|---|---|
| 1 | 24 | 58 | 18 |
| 2 | 10 | 70 | 20 |

TABLE 2-continued

Percentage of homodimer proteins and heterodimer proteins in expression products

| Group | ScFv-Fc homodimer (%) | ScFv-Fc/Fc heterodimer (%) | Fc homodimer (%) |
|---|---|---|---|
| 3 | 25 | 57 | 18 |
| 4 | 10 | 77 | 13 |

TABLE 3

Percentage of homodimer proteins and heterodimer proteins in expression products

| Group | ScFv-Fc homodimer (%) | ScFv-Fc/ Fc heterodimer (%) | Fc homodimer (%) |
|---|---|---|---|
| 2 | 17 | 60 | 23 |
| 5 | 14 | 72 | 14 |
| 6 | 14 | 62 | 24 |
| 4 | 21 | 69 | 10 |
| 7 | 24 | 64 | 12 |
| 8 | 21 | 71 | 8 |

TABLE 4

Percentage of homodimer proteins and heterodimer proteins in expression products

| Group | ScFv-Fc homodimer (%) | ScFv-Fc/VhH-Fc heterodimer (%) | VhH-Fc homodimer (%) |
|---|---|---|---|
| 4 | 13 | 68 | 19 |
| 9 | 7 | 80 | 13 |
| 10 | 15 | 85 | 0 |
| 11 | 14 | 83 | 3 |
| 12 | 10 | 84 | 6 |

TABLE 5

Percentage of homodimer proteins and heterodimer proteins in expression products

| Group | ScFv-Fc homodimer (%) | ScFv-Fc/VhH-Fc heterodimer (%) | VhH-Fc homodimer (%) |
|---|---|---|---|
| 2 | 9 | 64 | 27 |
| 14 | 6 | 81 | 13 |
| 15 | 5 | 88 | 7 |
| 17 | 9 | 84 | 7 |

As can be seen from tables 2-5 above, all groups of modifications promoted heterodimer formation very effectively. For illustrative purposes, the modifications in group (modifications in chain A: T366W+K409A; modifications in chain B: T366S+L368G+Y407A+F405K) were used in the following examples to generate the immunoconjugate or the protein mixtures of the present disclosure.

1.2 Preparation of Anti-EGFR (Cetuximab)

Full length amino acid sequences of the heavy chain and light chain of Cetuximab (also known as Erbitux or Erb, which is an antibody against epidermal growth factor receptor EGFR) were obtained, and corresponding DNA sequences encoding these amino acid sequences were obtained using online tool DNAworks (helixweb.nih.gov/dnaworks/). Then, nucleic acid molecules encoding the light chain of Cetuximab (Erb-LC) were synthesized. The amino acid sequence of Erb-LC is as set forth in SEQ ID NO: 37, and the corresponding polynucleotide sequence encoding it is as set forth in SEQ ID NO: 38. Then, point mutations (T366W and K409A) were introduced into the polynucleotide sequences encoding the Fc region of Cetuximab heavy chain gene, and nucleic acid molecules encoding the modified Cetuximab heavy chain were synthesized (referred to herein as erb-Fc9), the corresponding polypeptide encoding it was named as Erb-Fc9. The amino acid sequences of Erb-Fc9 is as set forth in SEQ ID NO: 39, and the polynucleotide sequence encoding it is as set forth in SEQ ID NO: 40.

1.3 Preparation of Anti-HER2 (Trastuzumab)

Full length amino acid sequences of the heavy chain and light chain of Trastuzumab were obtained according to US patent U.S. Pat. No. 7,879,325B2 (incorporated herein by reference). Then, corresponding DNA sequences encoding these amino acid sequences were obtained using online tool DNAworks (helixweb.nih.gov/dnaworks/). Nucleic acid molecules encoding the light chain of Trastuzumab (T-LC) were then synthesized. The amino acid sequence of T-LC is as set forth in SEQ ID NO: 41, and the corresponding polynucleotide sequence encoding it is as set forth in SEQ ID NO: 42. Then, point mutations (T366W and K409A) were introduced into the polynucleotide sequences encoding the Fc region of Trastuzumab heavy chain gene, and nucleic acid molecules encoding the modified Trastuzumab heavy chain were synthesized (referred to herein as t-Fc9), the corresponding polypeptide encoding it was named as T-Fc9. The amino acid sequences of T-Fc9 is as set forth in SEQ ID NO: 43, and the polynucleotide sequence encoding it is as set forth in SEQ ID NO: 44.

1.4 Preparation of Anti-FAP (28111)

Full length amino acid sequences of the heavy chain and light chain of 28H1 were obtained according to US20120128591A1 (incorporated herein by reference). Then, corresponding DNA sequences encoding these amino acid sequences were obtained using online tool DNAworks (helixweb.nih.gov/dnaworks/). Nucleic acid molecules encoding the light chain of 28H1 (28H1-LC) were then synthesized. The amino acid sequence of 28H1-LC is as set forth in SEQ ID NO: 45, and the corresponding polynucleotide sequence encoding it is as set forth in SEQ ID NO: 46. Then, point mutations (T366W and K409A) were introduced into the polynucleotide sequences encoding the Fc region of 28H1 heavy chain gene, and nucleic acid molecules encoding the modified 28H1 heavy chain were synthesized (referred to herein as 28H1-Fc9), the corresponding polypeptide encoding it was named as 28H1-Fc9. The amino acid sequences of 28H1-Fc9 is as set forth in SEQ ID NO: 47, and the polynucleotide sequence encoding it is as set forth in SEQ ID NO: 48.

1.5 Preparation of (IL10)$_2$-Fc6

First of all, sequence information of human interleukin 10 (IL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot.

Afterwards, point mutations (T366S, L368G, Y407A and F405K) were introduced into the IgG1-Fc fragment, and the polypeptide obtained thereby is referred to as Fc6. Then, a linker sequence "(GGGGS)$_3$" (SEQ ID NO: 49) was added to the N-terminus of the Fc6, to obtain linker-Fc6. The corresponding DNA sequence encoding it was then designed using online tool DNAworks (helixweb.nih.gov/dnaworks/). Then, a linker sequence "(GGGGS)$_3$" (SEQ ID NO: 49) was added between two copies of IL10, to obtain (IL10)$_2$. Polynucleotide sequences encoding (IL10)$_2$ were then added to the 5' end of the polynucleotide sequences encoding the linker-Fc6, thereby obtaining and synthesizing a polynucleotide sequence encoding the fusion protein (IL10)$_2$-Fc6. The amino acid sequence of (IL10)$_2$-Fc6 is as set forth in SEQ ID NO: 50, and the polynucleotide sequence encoding it is as set forth in SEQ ID NO: 51.

1.6 Preparation of IL10-Fc

First of all, sequence information of human interleukin 10 (IL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Then, a linker sequence "(GGGGS)$_3$" (SEQ ID NO: 49) was added to the N-terminus of IgG1-Fc, to obtain linker-Fc. The corresponding DNA sequence encoding it was then designed using online tool DNAworks (helixweb.nih.gov/dnaworks/). Polynucleotide sequences encoding IL10 were added to the 5' end of the polynucleotide sequences encoding the linker-Fc, thereby obtaining and synthesizing a polynucleotide sequence encoding the fusion protein IL10-Fc. The amino acid sequence of IL10-Fc is as set forth in SEQ ID NO: 52, and the polynucleotide sequence encoding it is as set forth in SEQ ID NO: 53.

1.7 Preparation of Fc9

Amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366W and K409A) were introduced into the IgG1Fc fragment, and the polypeptide obtained thereby is referred to as Fc9. The amino acid sequence of Fc9 is as set forth in SEQ ID NO: 17, and the polynucleotide sequence encoding it is as set forth in SEQ ID NO: 54.

Example 2 Construction of Recombinant Plasmids

The nucleic acid molecules (encoding Erb-Fc9, T-Fc9, 28H1-Fc9, Fc9, T-LC (Trastuzumab light chain), Erb-LC (Cetuximab light chain), 28H1-LC, (IL10)$_2$-Fc6, and IL10-Fc) obtained according to Example 1 were digested with HindIII and EcoRI (Takara), and then sub-cloned into the vector pcDNA4/myc-HisA (Invitrogen, V863-20), respectively. The plasmids obtained were verified by sequencing, and the correct recombinant plasmids were named as: pcDNA4-Erb-Fc9, pcDNA4-T-Fc9, pcDNA4-28H1-Fc9, pcDNA4-Fc9, pcDNA4-T-LC, pcDNA4-Erb-LC, pcDNA4-28H1-LC, pcDNA4-(IL10)$_2$-Fc6, and pcDNA4-IL10-Fc, respectively.

Example 3 Expression and Purification of the Immunoconjugates

Two days before transfection, 12×600 mL suspension domesticated HEK293 (ATCC CRL-1573™) cells were prepared for transient transfection, the cells were seeded at a density of 0.8×10$^6$ cells/ml. Two days later, three aliquots of cell suspension were centrifuged, and then resuspended in 600 mL Freestyle293 culture medium.

The recombinant expression vectors obtained from Example 2 were divided into the following groups:
Group1: pcDNA4-Erb-Fc9(200 μg)+pcDNA4-Erb-LC (200 μg)+p cDNA4-(IL10)$_2$-Fc6 (200 μg)
Group2: pcDNA4-T-Fc9 (200 μg)+pcDNA4-T-LC (200 μg)+pcDNA4-(IL10)$_2$-Fc6 (200 μg)
Group3: pcDNA4-28H1-Fc9(200 μg)+pcDNA4-28H1-LC(200 μg)+pcDNA4-(IL10)$_2$-Fc6 (200 μg)
Group4: pcDNA4-Fc9(200 μg)+pcDNA4-(IL10)$_2$-Fc6 (200 μg)
Group5: pcDNA4-IL10-Fc(200 μg)

All proteins were made in transiently transfected 293F cells. Briefly, FreeStyle 293F cells (Invitrogen) were grown in 293F medium (Invitrogen), transfected with non-linearized plasmid DNA and 293 Fectin reagent (Invitrogen) and grown in shaker flask batches in volumes mL/flask at 37° C., 5% CO$_2$ for 6 days. All proteins were purified by one-step protein A chromatography. The quality of each protein was determined by SDS-PAGE and SEC-HPLC. Similarly, the expression and purification results of the other immunoconjugates of the present application were verified and confirmed with SDS-PAGE.

The immunoconjugates thus obtained are named as (from Group 1 to Group 5, respectively): Erb-(IL10)$_2$, Tmab-(IL10)$_2$, 28H1-(IL10)$_2$, Fc9-(IL10) 2, and (IL10-Fc)$_2$.

Figure 1B:
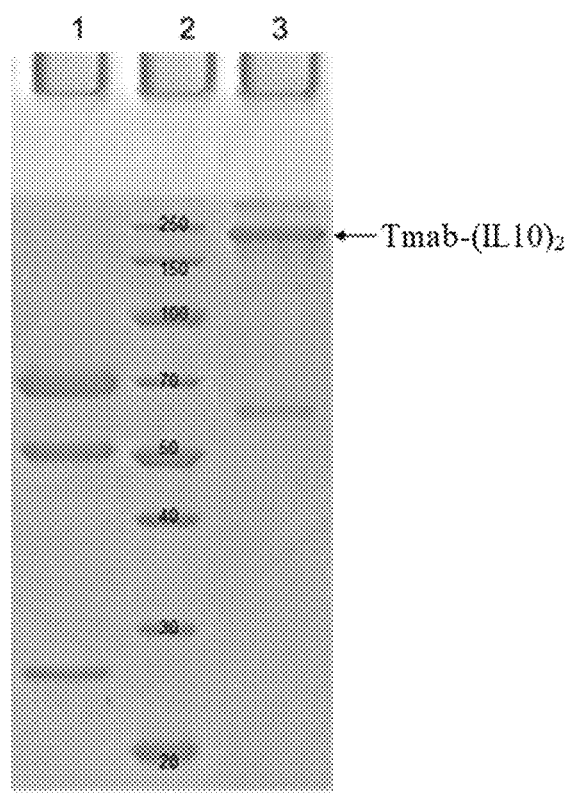

FIGS. 1A-1F show that the immunoconjugates of Erb-(IL10)$_2$, Tmab-(IL10)$_2$, (IL10-Fc)$_2$, and Fc9-(IL10)$_2$ was successfully expressed and purified. In FIG. 1A, lane 1 was loaded with Erb-(IL10)$_2$ (reducing); lane 2 was loaded with marker; lane 3 was loaded with Erb-(IL10)$_2$ (non-reducing). In FIG. 1B, lane 1 was loaded with Tmab-(IL10)$_2$ (reducing); lane 2 was loaded with marker; lane 3 was loaded with Tmab-(IL10)$_2$ (non-reducing).

Figure 1C:
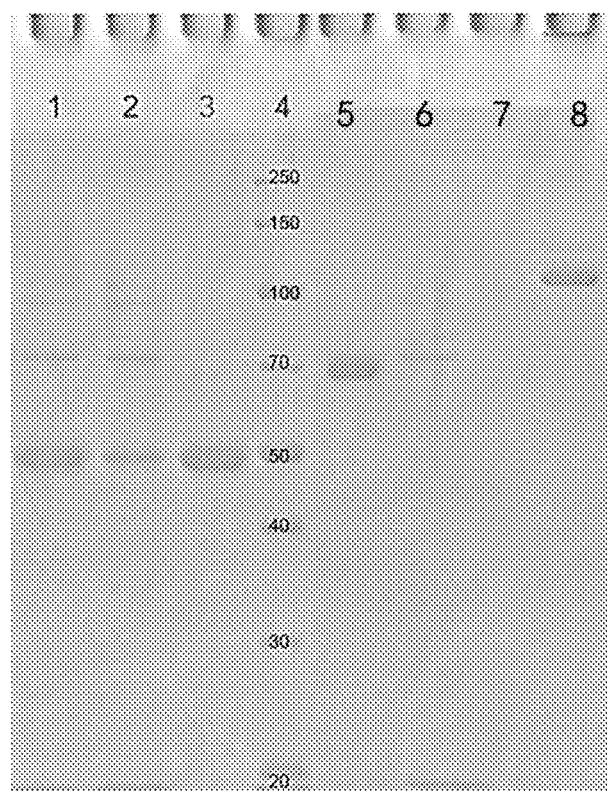

In FIG. 1C, lane 1 was loaded with (IL10-Fc)$_2$ (original sample); lane 2 was loaded with (IL10-Fc)$_2$ (flow-through); lane 3 was loaded with (IL10-Fc)$_2$ (eluted); lane 4 was loaded with marker; lane 5 was loaded with standard positive control BSA; lane 6 was loaded with blank buffer; lane 7 was blank; and lane 8 was loaded with (IL10-Fc)$_2$ (eluted; non-reducing).

Figure 1D:
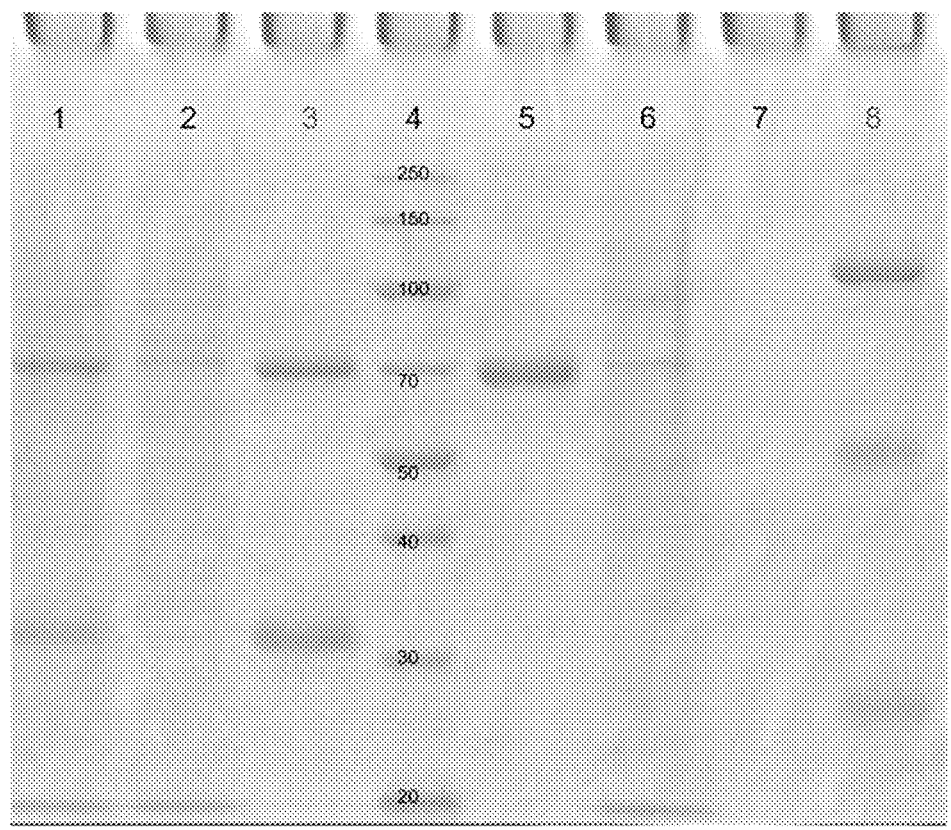

In FIG. 1D, lane 1 was loaded with Fc9-(IL10)$_2$ (original sample); lane 2 was loaded with Fc9-(IL10)$_2$ (flow-through); lane 3 was loaded with Fc9-(IL10)$_2$ (eluted); lane 4 was loaded with marker; lane 5 was loaded with standard positive control BSA; lane 6 was loaded with blank buffer; lane 7 was blank; lane 8 was loaded with Fc9-(IL10)$_2$ (eluted; non-reducing).

Figure 1E:
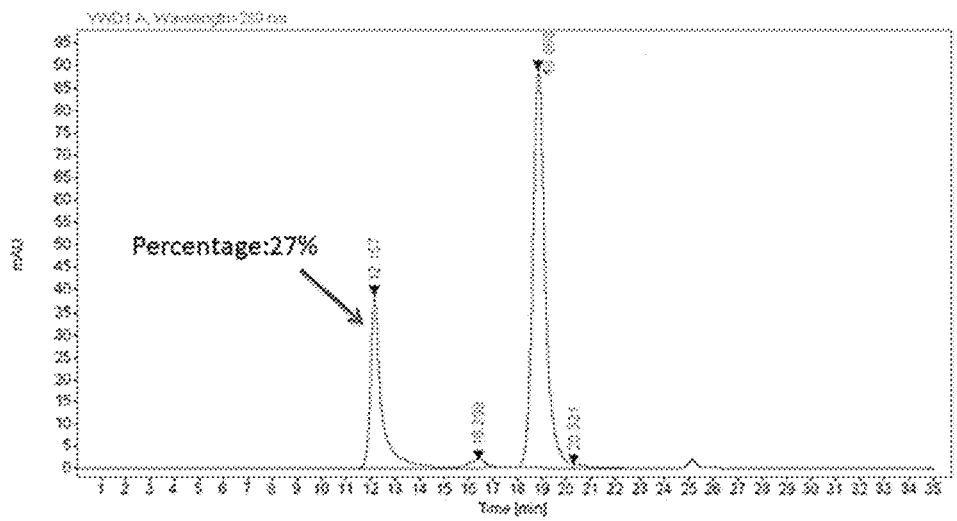

FIG. 1E shows the SEC-HPLC result, it can be seen that the percentage of undesired oligomers in the expression products of (IL10-Fc)$_2$ was about 27%.

Figure 1F:
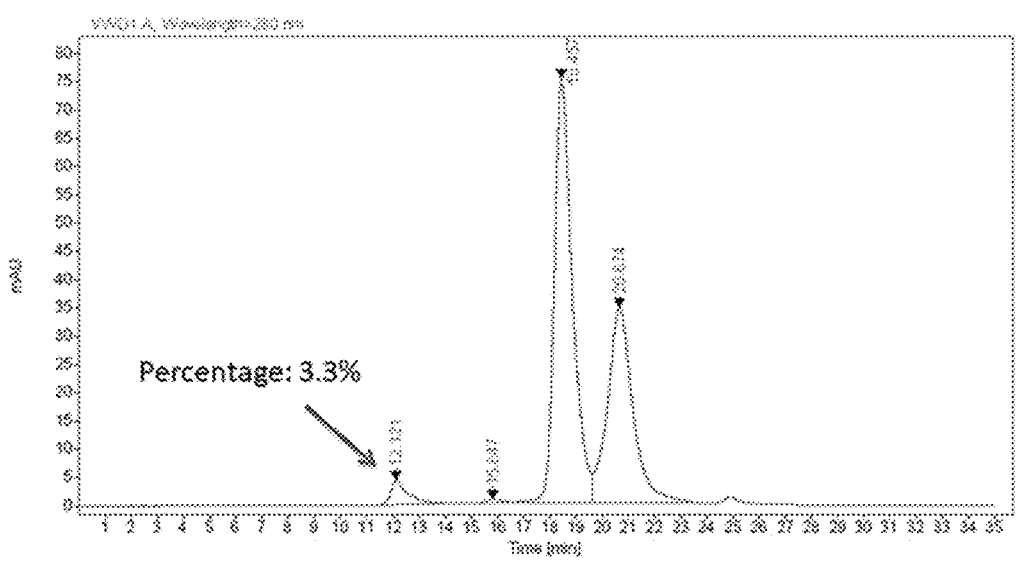

FIG. 1F shows the SEC-HPLC result, it can be seen that the percentage of undesired oligomers in the expression products of Fc9-(IL10)$_2$ was about 3.3%.

From these results, it can be seen that the immunoconjugates of the present disclosure have been successfully produced. Interestingly, the expression products of Fc9-(IL10)$_2$ contain much less undesired oligomers comparing to that of (IL10-Fc)$_2$.

Example 4 Examine Radiation Therapy Dosage and Tumor Control

4.1 Animals and Cell Culture

Female C57BL/6 mice were obtained from the Experimental Animal Centre of Chinese Academy of Science (Shanghai, China) at 6 to 8-week-old and maintained under specific pathogen-free conditions. All animals were used in accordance with the local ethics committee. This study was approved by the recommendations in the *Guide for the Care and Use of Medical Laboratory Animals* (Ministry of Health, People's Republic of China, 1998). The B16-EGFR-SIY melanoma cell line expressing human EGFR and a $K^b$-binding peptide antigen SIYRYYGL (SIY, SEQ ID NO: 55) was generated in house and grown in DMEM medium supplemented with 10% (v/v) fetal bovine serum (FBS), 100 units/ml penicillin, and 100 µg/ml streptomycin (Gibco Invitrogen).

4.2 Tumor Growth

B16-EGFR-SIY melanoma cells ($5 \times 10^5$) were inoculated subcutaneously (s.c.) into the flanks of mice and allowed to grow for about 10 days. Tumor volumes were recorded two perpendicular diameters (length and width) and calculated as $V=ab^2/2$, where a and b are the longest and the shortest diameter, respectively. According to tumor size mice were randomly assigned into groups. C57/BL6 mice, each weighing approximately 18-20 g, were anesthetized by intraperitoneally (i.p.) injecting about 150 µl/20 g 1% (w/v) pentobarbital sodium. Each anesthetized mouse positioned lateral on the flat horizontal surface of the block was protected with a lead shield with a 10-mm×10-mm hole. Local irradiation was then carried out with a single dose (Electron beam irradiation, 3 Gy/min; Medical Linear Accelerators, SIEMENS Primus, Germany) through the hole at the Department of Radiotherapy, The First Affiliated Hospital of Soochow University, and tumor volumes were measured twice weekly. Accordingly, the B16-EGFR-SIY control tumor model was obtained.

4.3 Radiation Therapy Dosage and Tumor Control

The B16-EGFR-SIY control tumor was treated with local single-dose Radiation Therapy (RT) of 5 Gy, 10 Gy, 20 Gy, 30 Gy. And the B16-EGFR-SIY control tumor model without any further local single-dose control was set as a control.

Figure 2:
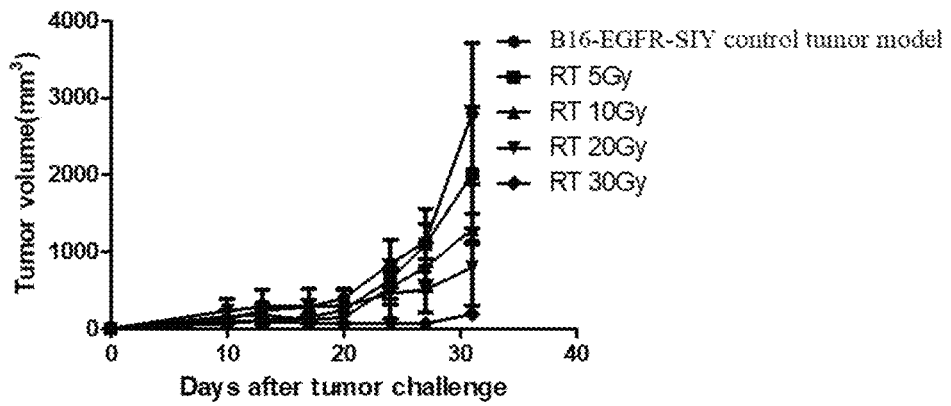
FIG. 2 illustrates the relationship between the dosage of radiotherapy and the tumor volume.

After 21 days of treatment of RT, the B16-EGFR-SIY control tumor model had grown from $123.4 \pm 43.7$ mm$^3$ to $2797.1 \pm 917.8$ mm$^3$ volume but this was slowed down by local single-dose RT between 5 Gy and 30 Gy (FIG. 2). FIG. 2 reflects the relationship between the single-dose of RT and the volume of the tumor. With the increase of single-dose of RT, the inhibition effect of RT on tumor was enhanced, 30 Gy almost mediated complete tumor elimination while had little effect. These results suggested that different radiation regimens causing unequal direct effects in terms of growth inhibition of the irradiated tumor.

Example 5 Synergistic Effect of RT and the Immunoconjugate of the Present Disclosure Administration of Erb-(IL10)$_2$ obtained in the Example 3 or isotype control (human IgG1) commenced on days 3 after the RT and was administered i.p. every 3-4 days for a total of 3 times at a dose of 1 mg/kg (unless otherwise stated).

Figure 3A:
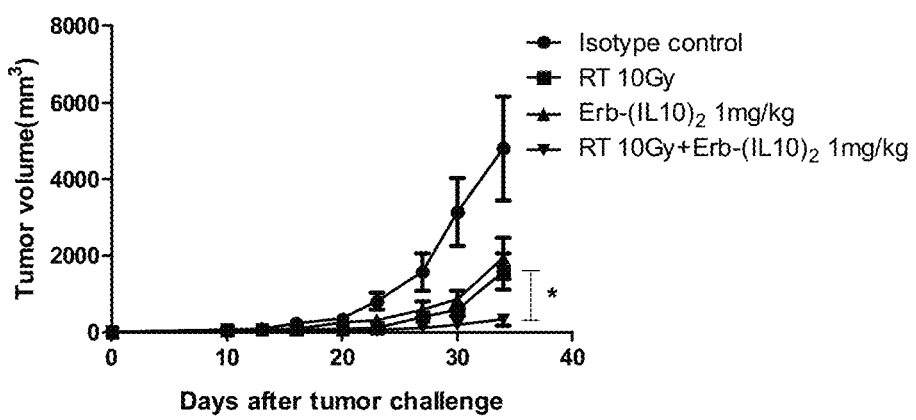
FIGS. 3A-3D illustrate the synergistic effect of RT in combination with the immunoconjugate of the present disclosure.
Figure 3B:
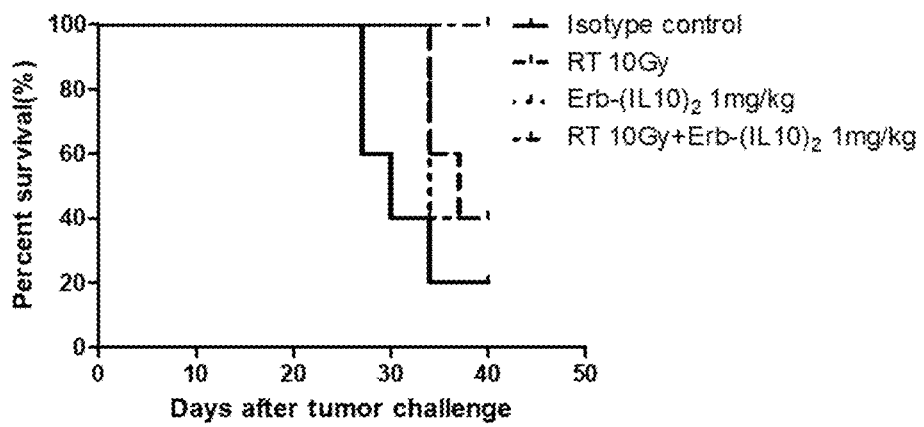
Figure 3C:
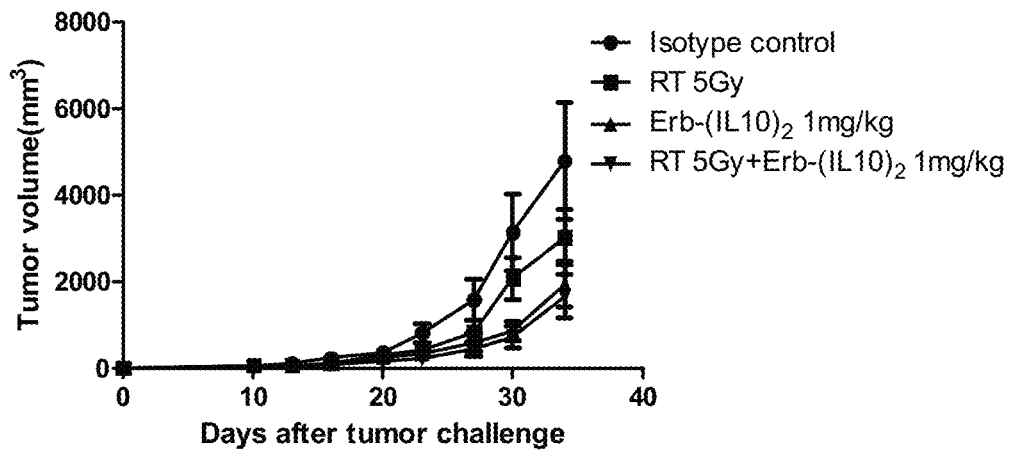

C57BL/6 mice were inoculated s.c. with B16-EGFR-SIY cells on day 0, irradiated locally on days 10 and subsequently injected i.p. with 200 µl of Erb-(IL10)$_2$ (1 mg/kg) or Fc9-(IL10)$_2$ (1 mg/kg) or an isotype control on days 13, every 3-4 days for a total of 3 times. The efficacy of Erb-(IL10)$_2$, RT; Fc9-(IL10)$_2$, RT and the combination of Erb-(IL10)$_2$ and RT; the combination of Fc9-(IL10)$_2$ and RT was determined and the results are shown in FIG. 3A-3C. Data were analyzed using GraphPad Prism version 5.0 software (San Diego, CA). The results are expressed as means±SEM. Two group comparisons were performed using unpaired Student's t-test. All reported p values are two-sided and the statistical significance level was set as *p<0.05, p<0.01, and *p<0.001. And a P value of less than 0.05 was considered statistically significant.

FIGS. 3A and 3C reflect the relationship between the tumor volume and the days after tumor challenge with single dose RT of 10 Gy, 5 Gy, respectively. And in the FIG. 3B, the horizontal coordinate is the days after tumor challenge and the vertical coordinate is the percent of survival of the mice. RT 5 Gy had a slight impact on tumor growth compared with isotype control group, whereas RT 10 Gy, Erb-(IL10)$_2$ slowed tumor progression (FIGS. 3A and 3C). Treatment with a combination of RT 10 Gy+Erb-(IL10)$_2$ effectively controlled tumor growth (P=0.0349, RT 10 Gy vs. RT 10 Gy+Erb-(IL10)$_2$ reveals the tumor volume of $1597.6 \pm 474.7$ mm$^3$ vs. $329.4 \pm 156.5$ mm$^3$ on days 34) (FIG. 3A). For tumors treated with the combination of RT 10 Gy and Erb-(IL10)$_2$, 5/5 did not reach 2000 mm$^3$ volume, as compared with 1/5 of the isotype control group (FIG. 3A). Reduction of the single-dose radiations to 5 Gy showed that RT+Erb-(IL10)$_2$ did not have an obvious synergistic effect (P=0.7088, Erb-(IL10)$_2$ $1940.2 \pm 539.7$ mm$^3$ vs. RT 5 Gy+Erb-(IL10)$_2$ $1654.3 \pm 504.4$ mm$^3$ on days 34) (FIG. 3C). Moreover, survival rate was significantly enhanced with the combination of RT 10 Gy and Erb-(IL10)$_2$, as shown in FIG. 3B.

These data indicate that Erb-(IL10)$_2$ significantly improves the effect of RT 10 Gy and the combination of RT 10 Gy and Erb-(IL10)$_2$ prolongs survival time of mice bearing B16-EGFR-SIY tumors.

Administration of Fc9-(IL10)$_2$ obtained in the Example 3 or isotype control (human IgG1) commenced on days 3 after the RT and was administered i.p. every 3-4 days for a total of 3 times at a dose of 1 mg/kg (unless otherwise stated).

Figure 3D:
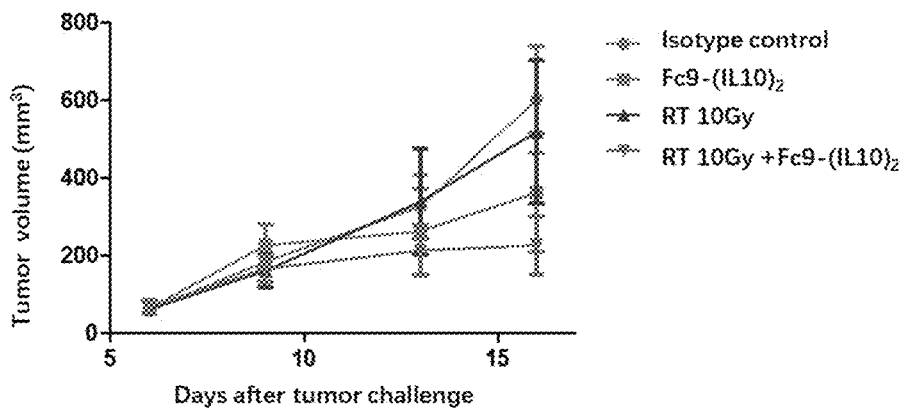

C57BL/6 mice were inoculated s.c. with B16-EGFR-SIY cells on day 0, irradiated locally on days 10 and subsequently injected i.p. with 0.32 mg/kg Fc9-(IL10)$_2$ or an 0.5 mg/kg isotype control on days 13, every 3-4 days for a total of 3 times. The efficacy of Fc9-(IL10)$_2$, RT; Fc9-(IL10)$_2$, RT and the combination of Fc9-(IL10)$_2$ and RT; the combination of Fc9-(IL10)$_2$ and RT was determined and the results are shown in FIG. 3D. Data were analyzed using GraphPad Prism version 5.0 software (San Diego, CA). The results are expressed as means±SEM.

FIG. 3D reflects the relationship between the tumor volume and the days after tumor challenge with single dose RT of 10 Gy. Treatment with a combination of RT 10 Gy+Fc9-(IL10)$_2$ effectively controlled tumor growth (FIG. 3D). The data indicate that Fc9-(IL10)$_2$ exerts the effective synergistic effect with RT 10 Gy.

Example 6 Determine the Administration Regime of RT and the Immunoconjugate of the Present Disclosure To determine the influence of administration regime on the synergistic effects of RT treatment in combination with the immunoconjugates of the present disclosure, Erb-(IL10)$_2$ treatment was provided on different days after RT treatment. Erb-(IL10)$_2$ was injected i.p. in mice three days before administering RT 10 Gy (days 10), simultaneously with RT 10 Gy (days 13) or three days after RT 10 Gy (days 16), respectively.

Figure 4:
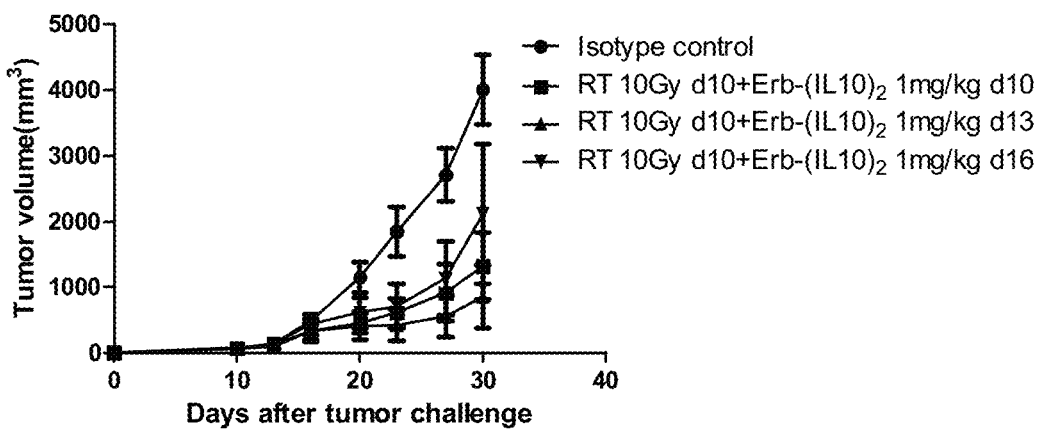
FIG. 4 illustrates the synergistic effect of RT in combination with the immunoconjugate of the present disclosure.

The results are shown in the FIG. 4, wherein the horizontal coordinate is the days after tumor challenge and the vertical coordinate is the volume of the tumor. As can be seen from FIG. 4, all combinations had a significant effect on the rate of tumor growth from day 10 through 30.

Although the effects on tumor growth were comparable for all the treatment groups (P=0.5218, RT 10 Gy d10+Erb-(IL10)$_2$ d13 vs. RT 10 Gy d10+Erb-(IL10)$_2$ d10=853.0±476.2 mm$^3$ vs. 1318.8±506.7 mm$^3$ on days 30; P=0.3115, RT 10 Gy d10+Erb-(IL10)$_2$ d13 vs. RT 10 Gy d10+Erb-(IL10)$_2$ d16=853.0±476.2 mm$^3$ vs. 2109.4±1061.2 mm$^3$ on days 30), surprisingly, comparing to the administration of Erb-(IL10)$_2$ and RT simultaneously or delaying the administration of Erb-(IL10)$_2$ until day 16, administering Erb-(IL10)$_2$ around 3 days after RT exerts the most effective synergistic effect.

Example 7 the Synergistic Effect is CD8$^+$ T Cell Dependent

Then the mechanisms underlying the synergistic effects of RT and Erb-(IL10)$_2$ combination was investigated. Firstly, the function of effector T cells and NK cells in mediating antitumor efficacy following the combined treatment was explored.

Figure 5A:
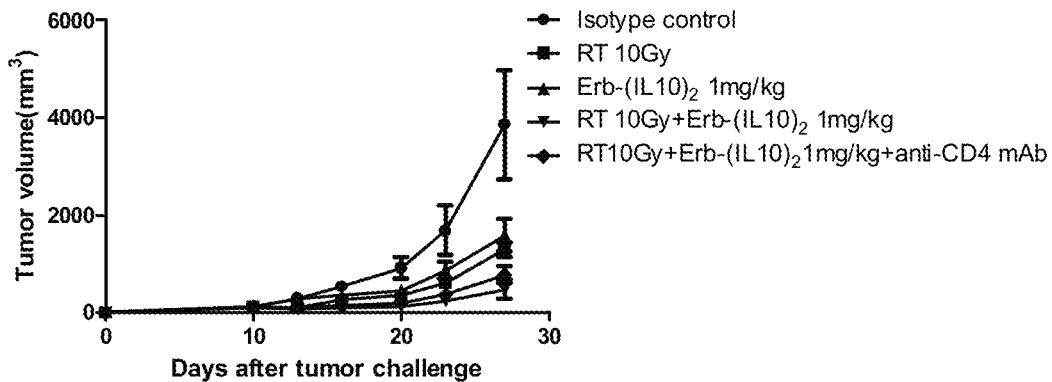
FIGS. 5A-5C illustrate the synergistic effect of RT in combination with the immunoconjugate of the present disclosure.
Figure 5B:
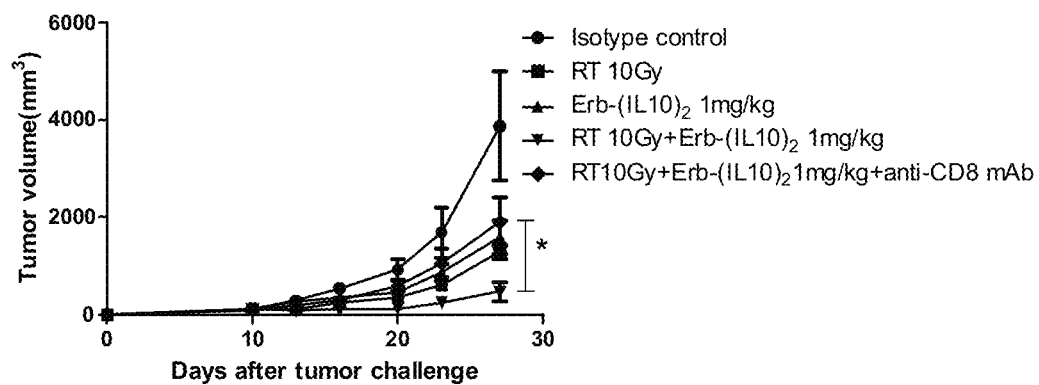
Figure 5C:
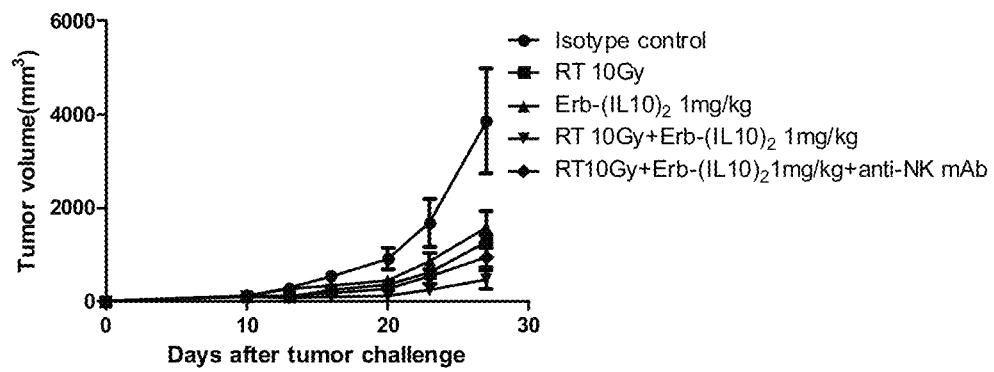

Mice treated with RT and Erb-(IL10) 2 further received i.p. injections of anti-CD4 mAb (clone TIB207, 200 µg/mouse), anti-CD8 mAb (clone TIB210, 200 µg/mouse), or anti-NK mAb (clone PK136, 200 µg/mouse) once/week, respectively, starting on day 10, and the treatment was administered twice in total. As shown in FIGS. 5A and 5C, depletion of CD4$^+$ T cells or NK cells did not significantly affect the effects of the combination therapy on tumor growth (P=RT 10 Gy+Erb-(IL10)$_2$ 1 mg/kg+anti-CD4 mAb vs. RT 10 Gy+Erb-(IL10)$_2$ 1 mg/kg=771.4±172.5 mm$^3$ vs. 474.8±190.7 mm$^3$ on days 27; P=0.1651, RT 10 Gy+Erb-(IL10)$_2$ 1 mg/kg+anti-NK mAb vs. RT 10 Gy+Erb-(IL10)$_2$ 1 mg/kg=940.1±219.7 mm$^3$ vs. 474.8±190.7 mm$^3$ on days 27). However, depletion of CD8$^+$ T cells drastically reduced the treatment efficacy, resulting in rapid tumor outgrowth (P=0.0376, RT 10 Gy+Erb-(IL10)$_2$ 1 mg/kg+anti-CD8 mAb vs. RT 10 Gy+Erb-(IL10)$_2$ 1 mg/kg=1896.1±499.6 mm$^3$ vs. 474.8±190.7 mm$^3$ on days 27), as shown in FIG. 5B. Accordingly, these results demonstrate that CD8$^+$ T cells are essential for the antitumor effect of the combination therapy.

Example 8 the Combination Therapy Mediated an Abscopal Effect on Distant Tumors and Improved Tumor-Specific CD8$^+$ T Cells Function in Tumor Masses 8.1 Abscopal Effect C57BL/6 mice were injected s.c. on day 0 with 5×10$^5$ B16-EGFR-SIY cells on the right flank (primary tumor) and with equivalent number of cells on the left flank (secondary tumor). The primary tumors were treated locally with RT 10 Gy on day 10, and then were injected i.p. with 1 mg/kg Erb-(IL10)$_2$ on days 13, every 3-4 days for three times, as indicated. Primary and secondary tumor volumes were measured and monitored.

To assess any abscopal effect (i.e., indirect effect) of RT and RT+Erb-(IL10)$_2$ combination, B16-EGFR-SIY cells were injected s.c. into C57BL/6 mice at both flanks: the primary tumor on the right flank was irradiated to determine the direct therapeutic effect, whereas the secondary tumor on the left flank was not irradiated and served to measure the potential indirect, systemic effects. These treatments resulted in a significant growth delay of the primary tumors, similar to that shown in FIG. 3A.

Figure 6A:
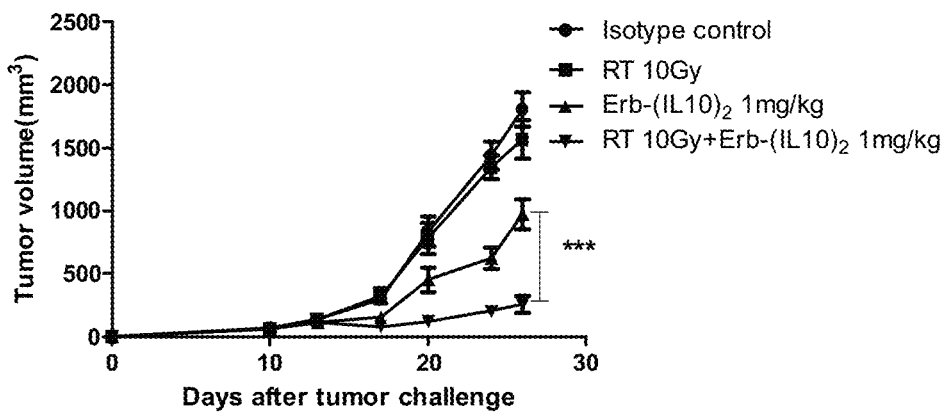
FIGS. 6A-6F illustrate the synergistic effect of RT in combination with the immunoconjugate of the present disclosure.

The effects on secondary tumor growth were shown in FIG. 6A. Three experiments were conducted with 5 mice per group. The effect of i.p. injection of Erb-(IL10)$_2$ alone was similar to that seen on primary tumors. However, although single RT 10 Gy treatment caused significant growth delay of the primary tumors, no effect was observed for secondary tumors (FIG. 6A).

In contrast, the combination of Erb-(IL10)$_2$ with RT resulted in significant further growth delay of secondary tumors, as compared to the results obtained with the administration of Erb-(IL10)$_2$ alone (P=0.0009, Erb-(IL10)$_2$ vs. RT 10 Gy+Erb-(IL10)$_{2=970.2±119.6}$ mm$^3$ vs. 253.9±71.6 mm$^3$ on days 26). Taken together, these results indicate that a single dose of local radiation (10 Gy) is unlikely to trigger an abscopal effect, but the combination of RT 10 Gy with Erb-(IL10)$_2$ can elicit significant antitumor effect on distant tumors.

8.2 Enhancement of Antigen-Specific T Cell Responses

To investigate the effects of the combination therapy in enhancing tumor antigen-specific T cell responses, the SW peptide was used to identify SIY-reactive CD8$^+$ T cells.

The enzyme-linked immunospot (ELISPOT) assay was used to quantify cells secreting interferon gamma (IFNγ), using 96-well plates. An ELISPOT kit was used (BD Biosciences Cat #551083) according to the manufacturer's instructions. Tumor-draining lymph nodes (DLNs) were removed to obtain single-cell suspensions as described. A 96-well ELISPOT plate was pre-coated with 5 µg/ml purified anti-mouse IFN-γ (BD Biosciences Cat #51-2525kc), overnight at 4° C. 5×10$^5$ lymph node cells per well were cocultured in the presence of 10 µg/ml SIY polypeptides (SL-9 GL Biochem Cat #057787) or ovalbumin (OVA) polypeptides (InvivoGen Cat #vac-sin), the latter was used as a negative control for antigen specificity. After 72 hours of incubation, cells were removed, 2 µg/ml biotinylated anti-mouse IFN-γ (BD Biosciences Cat #51-1818kz) was added, and the plate was incubated for 2 hours at room temperature. Spots were visualized using Streptavidin-HRP (BD Biosciences Cat #557630) and AEC substrate (BD Biosciences Cat #551951), followed by image analysis and spot enumeration. Each condition was tested in duplicate and the average value was shown. Tumors received RT 10 Gy, and 1 mg/kg Erb-(IL10)$_2$ was administered i.p., as previously described. Three days after the second administration of Erb-(IL10)$_2$, mice were sacrificed and tumor-DLNs were removed to acquire single cell suspensions and conduct ELISPOT assays.

Figure 6B:
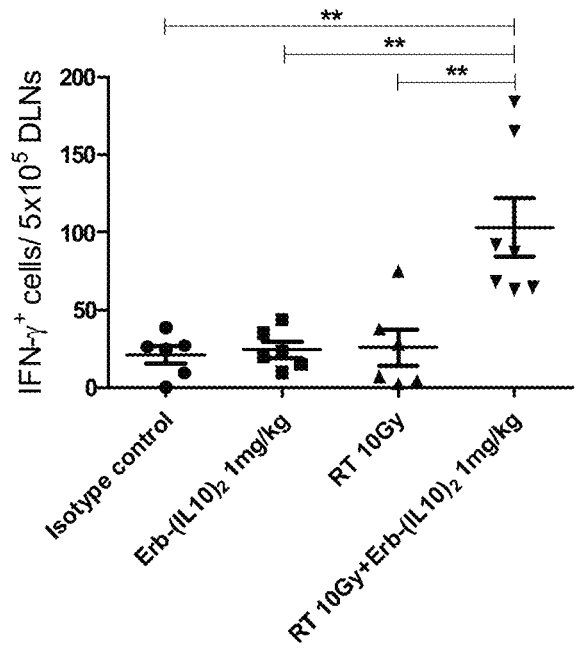

3 days after the second administration of Erb-(IL10)$_2$ (i.e., on day 19), lymphocytes from tumor-DLNs were isolated from the mice inoculated with B16-EGFR-SIY melanoma cells. Tumor-draining lymph node cells from each group of mice were activated in vitro with SIY or OVA peptides in the ELISPOT assay, and the number of IFN-γ-secreting cells was then determined, as shown in FIG. 6B. The number of SIY-specific IFN-γ-producing CD8+ T cells in DLNs of mice that received the combination treatment of RT and Erb-(IL10)$_2$ was significantly increased, compared with those treated with RT or Erb-(IL10)$_2$ alone (P=0.0026, isotype control vs. RT+Erb-(IL10)$_2$; P=0.0034, Erb-(IL10)$_2$ vs. RT+Erb-(IL10)$_2$; P=0.0064, RT vs. RT+Erb-(IL10)$_2$). Overall, these findings demonstrate that the combination of RT and Erb-(IL10)$_2$ therapy increases the effect of tumor control by improving the systemic activation of tumor-specific T cells in tumor-DLNs and by enhancing the functions of tumor antigen-specific T cells in the tumor microenvironment.

8.3 the Derivation of Activated T Cell after Treatment with the Combination Therapy FTY720 (SIGMA, Cat #SML0700-5MG) was used to test activation of T cells in the tumor microenvironment. FTY720 is a lipophilic immunomodulatory sphingosine-1-phosphate analog, it induces severe peripheral blood lymphopenia and sustains lymphopenia in mice by preventing lymphocytes to egress from lymph organs through agonist-induced receptor internalization.

B16-EGFR-SIY cells were inoculated s.c. into the both flanks of mice. Starting 10-day post B16-EGFR-SIY melanoma cell implantation, mice in the radiation therapy+Erb-(IL10)$_2$ group received their first i.p. injections. Then 3 days later, after the first administration of depletion antibodies or FTY720, lymphocytes suspensions were prepared from their peripheral blood, and labeled with APC-anti-mCD4 (clone GK1.5, BioLegend), FITC-anti-mCD8a (clone 53-6.7, BioLegend), FITC-anti-mCD3 (clone 17A2, BioLegend), or APC-anti-mNK1.1 (clone PK136, BioLegend). Tumor volumes on the both flanks were measured and monitored. Samples were analyzed on a Life Attune Flow Cytometer (Life), and data were analyzed. Representative data is shown in FIG. 6C-6F, based on results obtained from three experiments conducted with 5-6 mice per group.

Figure 6C:
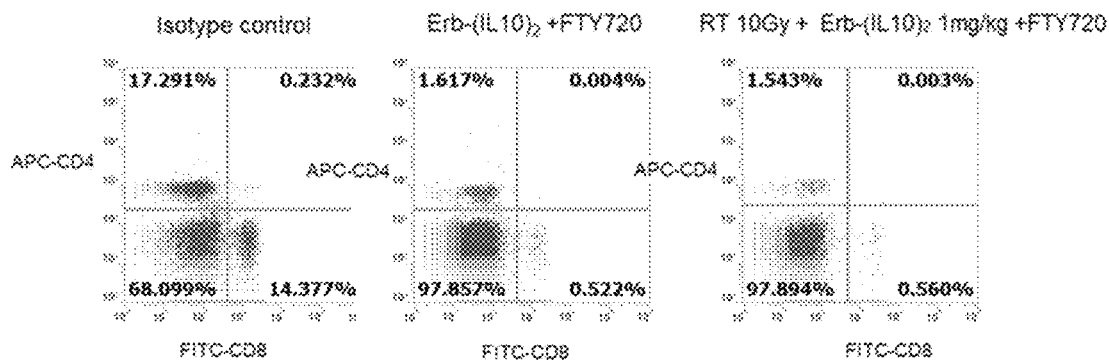

The distribution of CD4+ and CD8+ lymphocytes in the peripheral blood was assessed 3 days after the first administration of FTY720, it was found that the relative numbers of CD8+ T cells and CD4+ T cells declined to about 0.5% and 1.5%, respectively, as shown in FIG. 6C.

Figure 6D:
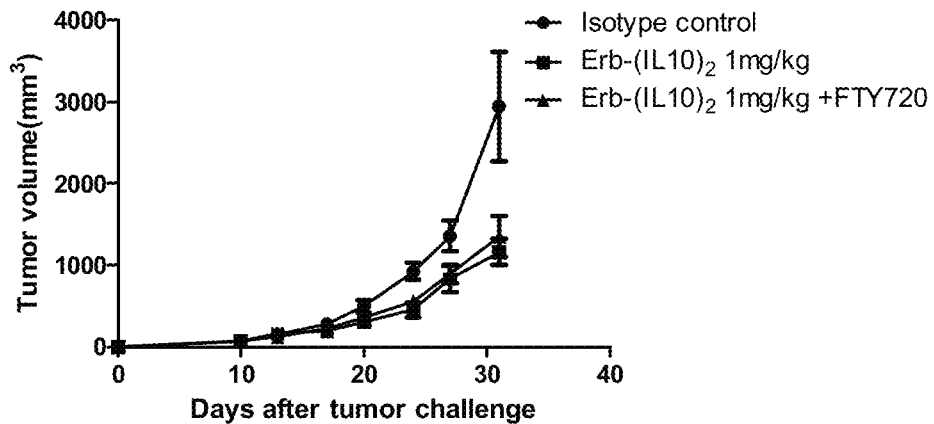
Figure 6E:
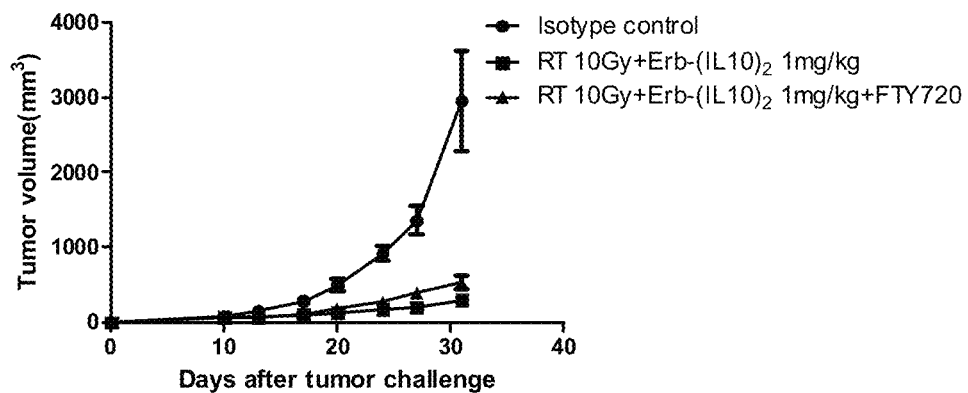
Figure 6F:
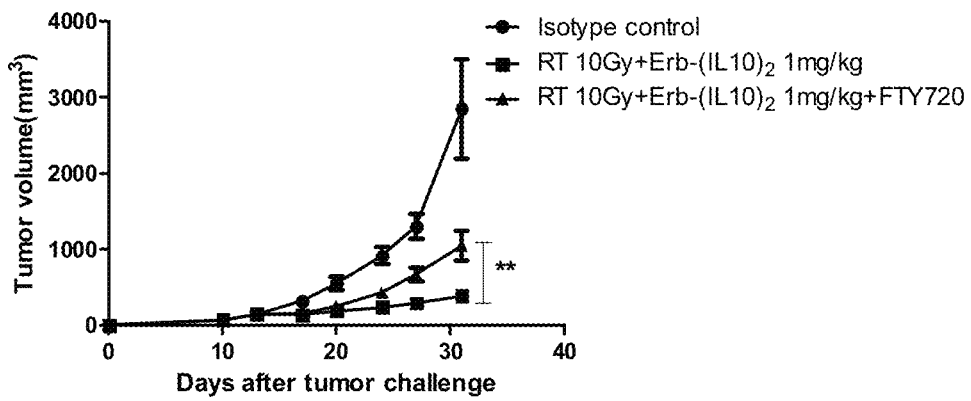

However, it was observed that the antitumor effect of Erb-(IL10)$_2$ 1 mg/kg alone was not diminished by FTY720 treatment, as shown in FIG. 6D. In the combination therapy (i.e., RT+Erb-(IL10)$_2$), FTY720 abrogated the anti-tumor effect significantly for the secondary tumors (P=0.0081, RT 10 Gy+Erb-(IL10)$_2$ 1 mg/kg vs. RT 10 Gy+Erb-(IL10)$_2$ 1 mg/kg+FTY720=392.5±33.9 mm$^3$ vs. 1052.4±197.5 mm$^3$ on days 31) (as shown in FIG. 6F) while had only marginal effect on the primary tumors (P=0.0665, RT 10 Gy+Erb-(IL10)$_2$ 1 mg/kg vs. RT 10 Gy+Erb-(IL10)$_2$ 1 mg/kg+FTY720=298.1±73.4 mm$^3$ vs. 537.9±90.4 mm$^3$ on days 31) (as shown in FIG. 6E). Therefore, the combination of RT with the immunoconjugate of the present disclosure activated T cells in the tumor microenvironment For the above experiments, similar resulted were obtained for Tmab-(IL10)$_2$, 28H1-(IL10)$_2$, Fc9-(IL10)$_2$, and (IL10-Fc)$_2$.

Example 9 the Effect of Cytotoxic Chemotherapy in Combination with the Immunoconjugate of the Present Disclosure

9.1 Effects of the Immunoconjugate According to the Present Disclosure in Combination with Doxorubicin The B16-EGFR-SIY control tumor model was obtained as described above in the Example 4. To compare the effects of Erb-(IL10)$_2$ in combination with doxorubicin, mice were divided into several groups with 5 mice per group: Group isotype control, treated with 1 mg/kg human IgG1 (20 μg/mouse); Group Erb-(IL10)$_2$, treated with 1 mg/kg (20 μg/mouse) Erb-(IL10)$_2$; Group doxorubicin, treated with 5 mg/kg (100 μg/mouse) doxorubicin; Group Erb-(IL10)$_2$+ doxorubicin, treated with 1 mg/kg Erb-(IL10)$_2$ plus 5 mg/kg doxorubicin. C57BL/6 mice were inoculated s.c. with B16-EGFR-SIY cells on day 0, Erb-(IL10)$_2$ was injected i.p. on the day 7, 10, 14 respectively; and doxorubicin was injected through tail vein on the day 7.

Figure 7A:
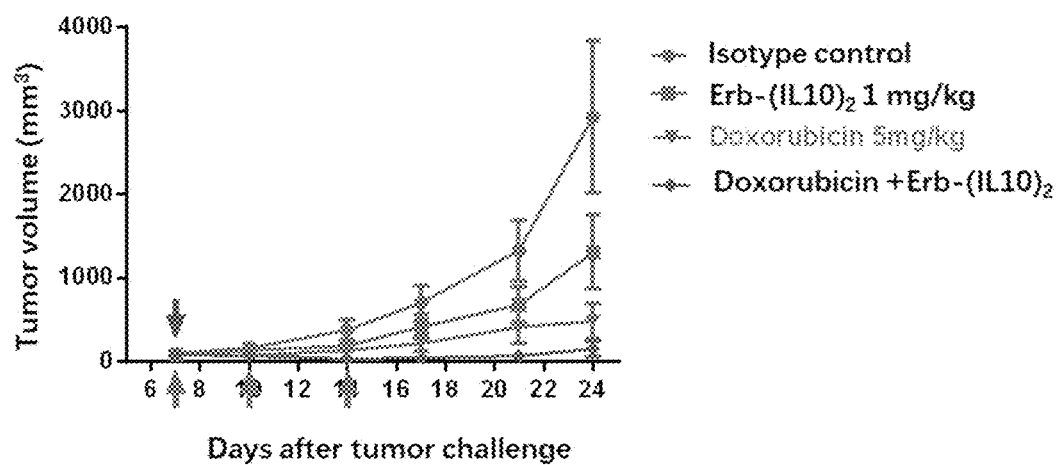
FIGS. 7A-7J illustrate the effect of various chemotherapies in combination with the immunoconjugate of the present disclosure.

The results are shown in FIG. 7A. It can be seen that a synergistic effect in controlling tumor growth was observed for the combination of Erb-(IL10)$_2$ with doxorubicin.

To compare Fc9-(IL10)$_2$ in combination with doxorubicin, mice were divided into several groups with 5 mice per group: Group isotype control, treated with 0.5 mg/kg human IgG1(10 μg/mouse); Group Fc9-(IL10)$_2$, treated with 0.5 mg/kg (10 μg/mouse) Fc9-(IL10)$_2$; Group doxorubicin, treated with 5 mg/kg (100 μg/mouse) doxorubicin; Group Fc9-(IL10)$_2$+doxorubicin, treated with 0.5 mg/kg Fc9-(IL10)$_2$ plus 5 mg/kg doxorubicin. C57BL/6 mice were inoculated s.c. with B16-EGFR-SIY cells on day 0, Fc9-(IL10)$_2$ was injected i.p. on the day 7, 14 respectively; and doxorubicin was injected through tail vein on the day 7.

Figure 7B:
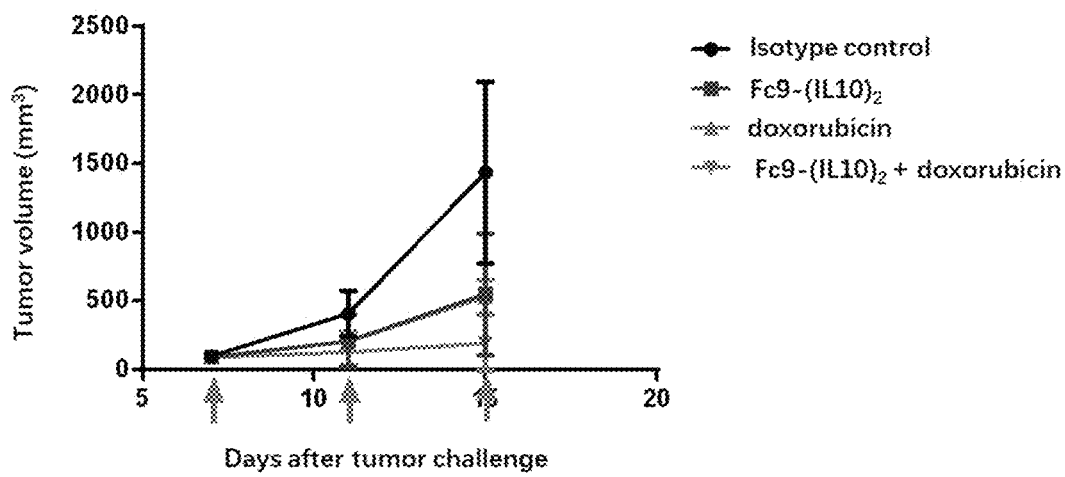

The results are shown in FIG. 7B. It can be seen that a synergistice effect in controlling tumor growth was observed for the combination of Fc9-(IL10)$_2$ with doxorubicin.

9.2 Effects of the Immunoconjugate According to the Present Disclosure in Combination with Oxaliplatin The B16-EGFR-SIY control tumor model was obtained as described above in the Example 4. To compare the effects of Erb-(IL10)$_2$ in combination with oxaliplatin, mice were divided into several groups with 5 mice per group: Group isotype control, treated with 0.5 mg/kg human IgG1(10 μg/mouse); Group Erb-(IL10)$_2$, treated with 0.5 mg/kg (10 μg/mouse) Erb-(IL10)$_2$; Group oxaliplatin, treated with 15 mg/kg (300 μg/mouse) oxaliplatin; Group Erb-(IL10)$_2$+ oxaliplatin, treated with 0.5 mg/kg Erb-(IL10)$_{2+15}$ mg/kg oxaliplatin. C57BL/6 mice were inoculated s.c. with B16-EGFR-SIY cells on day 0, Erb-(IL10)$_2$ was injected i.p. on the day 7, 10, 14 respectively; and oxaliplatin was injected through tail vein on the day 7.

Figure 7C:
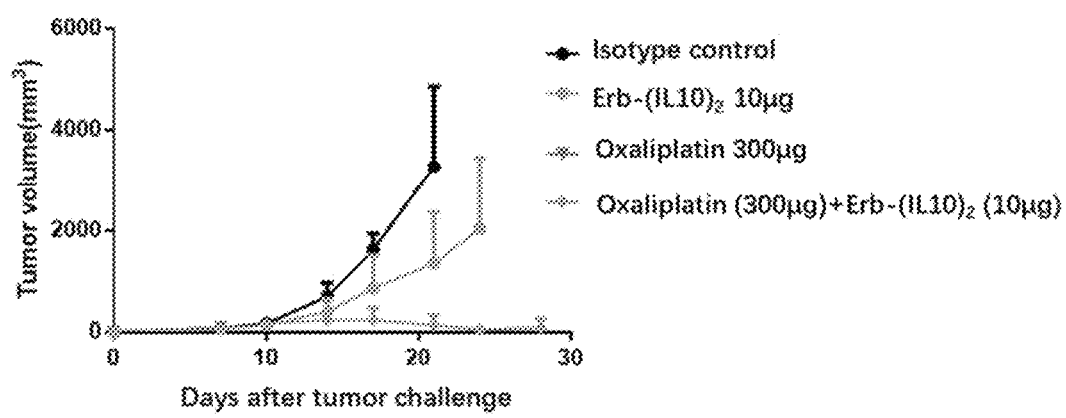

The results are shown in FIG. 7C. Due to the high toxicity of oxaliplatin, all of the mice in Group oxaliplatin were dead after 14 days (see FIG. 7I). It can be seen that a synergistice effect in controlling tumor growth was observed for the combination of ERB-(IL10)$_2$ with oxaliplatin.

To compare the effects of Fc9-(IL10)$_2$ in combination with oxaliplatin, mice were divided into several groups with 5 mice per group: Group Isotype control, treated with 0.5 mg/kg human IgG1 (10 μg/mouse); Group Fc9-(IL10)$_2$ treated with 0.5 mg/kg (10 μg/mouse) Fc9-(IL10)$_2$; Group oxaliplatin, treated with 15 mg/kg (300 μg/mouse) oxaliplatin; Group Fc9(IL10)$_2$+oxaliplatin, treated with 0.5 mg/kg Fc9-(IL10)$_{2+15}$ mg/kg (300 μg/mouse) oxaliplatin. C57BL/6 mice were inoculated s.c. with B16-EGFR-SIY cells on day 0, Fc9-(IL10)$_2$ was injected i.p. on the day 7, 10, 14 respectively; and oxaliplatin was injected through tail vein on the day 7.

Figure 7D:
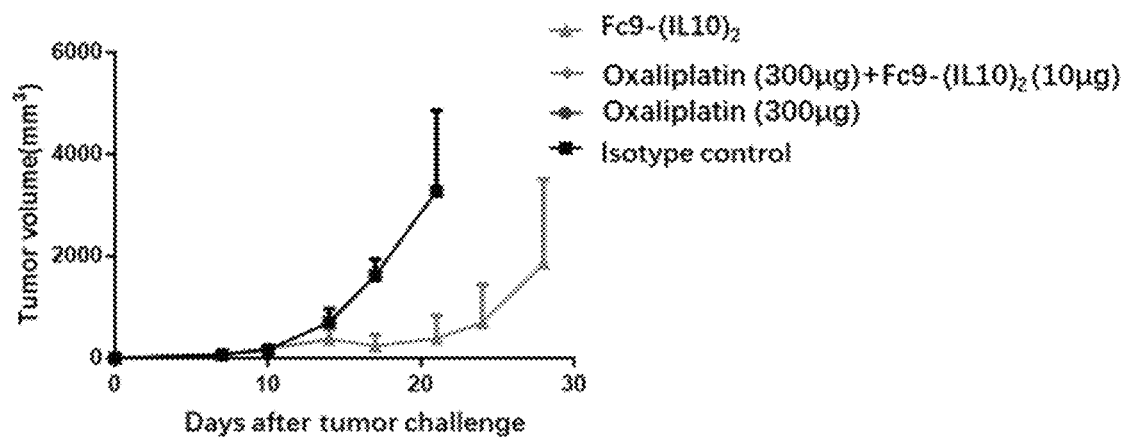

The results are shown in FIG. 7D. Due to the high toxicity of oxaliplatin, all of the mice in Group oxaliplatin and Group Fc9-(IL10)$_2$+oxaliplatin were dead after 14 days (see FIG. 7J). Thus, the synergistic effect cannot be compared between the groups.

9.3 Effects of the Immunoconjugate According to the Present Disclosure in Combination with CTX (Cyclophosphamide)

The B16-EGFR-SIY control tumor model was obtained as described above in the Example 4. To compare the effects of Erb-(IL10)$_2$ in combination with CTX, mice were divided into several groups with 5 mice per group: Group PBS, treated with PBS buffering; Group Erb-(IL10)$_2$, treated with 0.5 mg/kg (10 μg/mouse) Erb-(IL10)$_2$; Group CTX, treated with 100 mg/kg (2 mg/mouse) CTX; Group Erb-(IL10)$_2$+CTX treated with 0.5 mg/kg Erb-(IL10)$_2$ plus 100 mg/kg CTX. C57BL/6 mice were inoculated s.c. with B16-EGFR-SIY cells on day 0, Erb-(IL10)$_2$ was injected i.p. on the day 7, 10, 14 respectively; and CTX was injected through tail vein on the day 7.

Figure 7E:
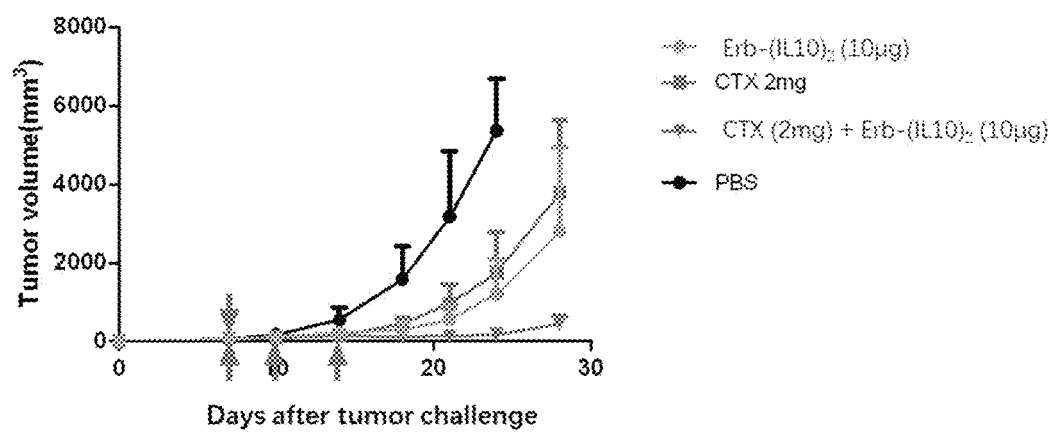

The results are shown in FIG. 7E. It can be seen that a synergistic effect in controlling tumor growth was observed for the combination of Erb-(IL10)$_2$ with CTX.

To compare the effects of Fc9-(IL10)$_2$ in combination with CTX, mice were divided into several groups with 5 mice per group: Group isotype control, treated with 1 mg/kg human IgG1(20 μg/mouse); Group Fc9-(IL10)$_2$, treated with 0.65 mg/kg (13 μg/mouse) Fc9-(IL10)$_2$; Group CTX, treated with 100 mg/kg (2 mg/mouse) CTX; Group Fc9-(IL10)$_2$+CTX treated with Fc9-(IL10)$_2$ plus 100 mg/kg CTX. C57BL/6 mice were inoculated s.c. with B16-EGFR-SIY cells on day 0, Fc9-(IL10)$_2$ was injected i.p. on the day 7, 10, 14 respectively; and CTX was injected through tail vein on the day 7.

Figure 7F:
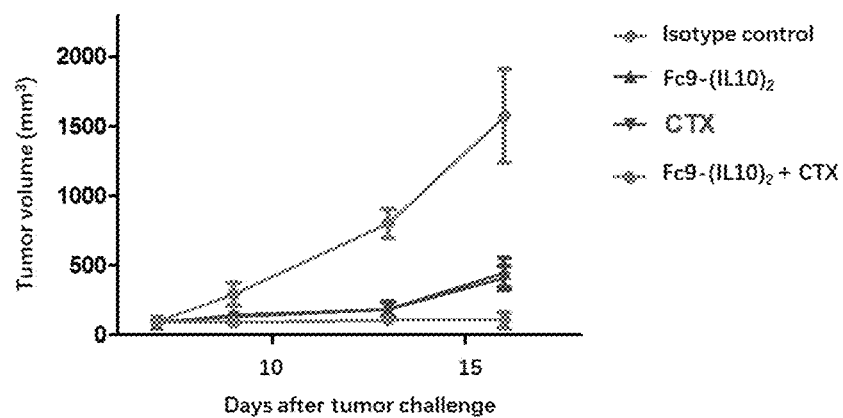

The results are shown in FIG. 7F. It can be seen that a synergistic effect in controlling tumor growth was observed for the combination of Fc9-(IL10)$_2$ with CTX.

9.4 Effects of the Immunoconjugate According to the Present Disclosure in Combination with Vinorelbine The B16-EGFR-SIY control tumor model was obtained as described above in the Example 4. To compare the effects of Erb-(IL10)$_2$ in combination with vinorelbine, the mice were divided into several groups with 5 mice per group: Group isotype control, treated with human IgG1 (10 μg/mouse); Group Erb-(IL10)$_2$, treated with 0.5 mg/kg (10 μg/mouse) Erb-(IL10)$_2$; Group vinorelbine, treated with 5 mg/kg (100 μg/mouse) vinorelbine; Group Erb-(IL10)$_2$+vinorelbine, treated with 0.5 mg/kg Erb-(IL10)$_{2+5}$ mg/kg vinorelbine; C57BL/6 mice were inoculated s.c. with B16-EGFR-SIY cells on day 0, Erb-(IL10)$_2$ was injected i.p. on the day 7, 10, 14 respectively; and vinorelbine was injected through tail vein on the day 7.

Figure 7G:
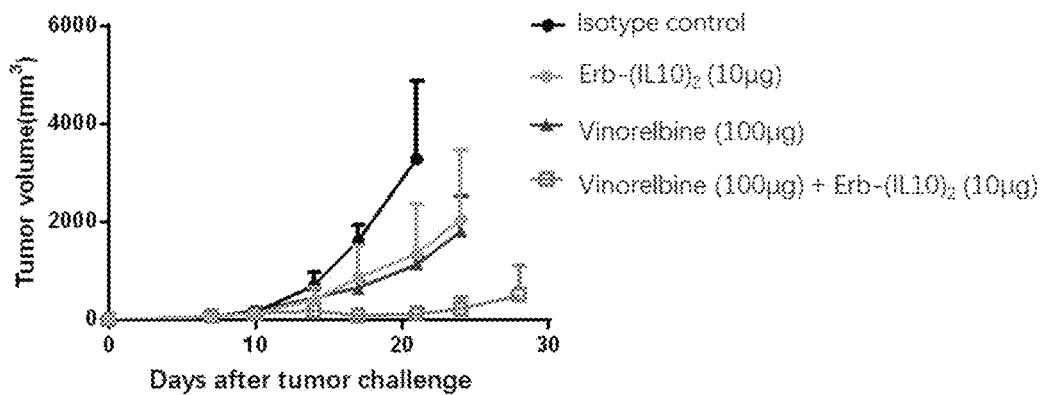

The results are shown in FIG. 7G. It can be seen that a synergistic effect in controlling tumor growth was observed for the combination of Erb-(IL10)$_2$ with vinorelbine.

To compare the effects of Fc9-(IL10)$_2$ in combination with vinorelbine, mice were divided into several groups with 5 mice per group: Group isotype control, treated with human IgG1(10 μg/mouse); Group Fc9-(IL10)$_2$, treated with 0.5 mg/kg (10 μg/mouse) Fc9-(IL10)$_2$; Group vinorelbine, treated with 5 mg/kg (100 μg/mouse) vinorelbine; Group Fc9-(IL10)$_2$+vinorelbine treated with 0.5 mg/kg Fc9-(IL10)$_{2+5}$ mg/kg vinorelbine. C57BL/6 mice were inoculated s.c. with B16-EGFR-SIY cells on day 0, Fc9-(IL10)$_2$ was injected i.p. on the day 7, 10, 14 respectively; and vinorelbine was injected through tail vein on the day 7.

Figure 7H:
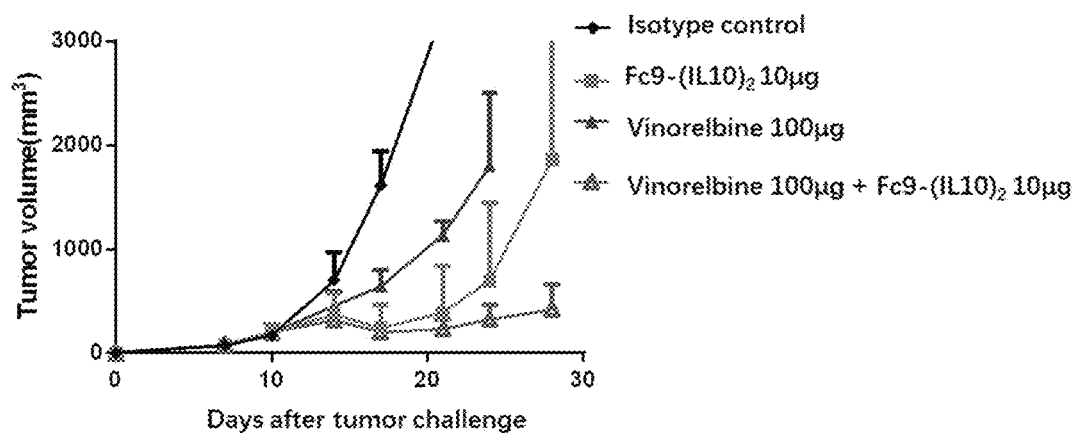

The results are shown in FIG. 7H. It can be seen that a synergistic effect in controlling tumor growth was observed for the combination of Fc9-(IL10)$_2$ with vinorelbine.

Figure 7I:
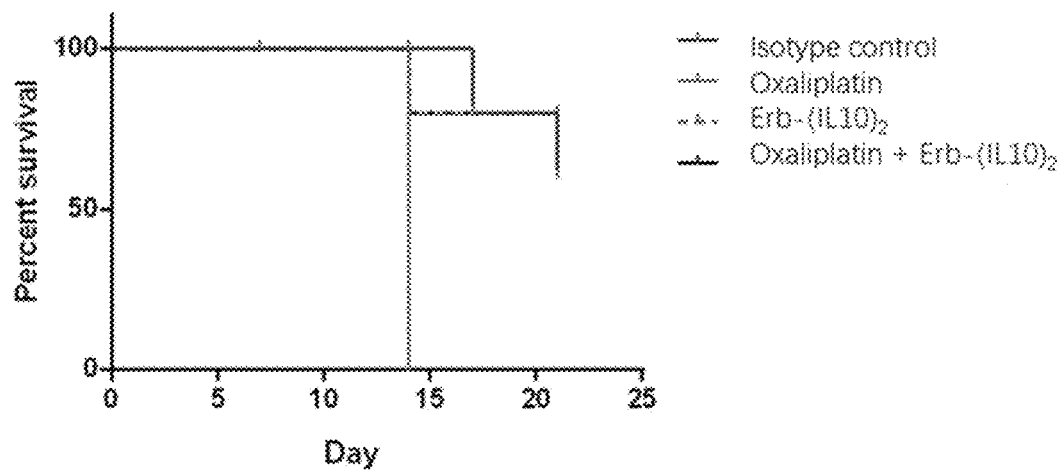

FIG. 7I shows the effects on survival rate for Erb-(IL10)$_2$, oxaliplatin, and the combination of Erb-(IL10)$_2$ with oxaliplatin.

Figure 7J:
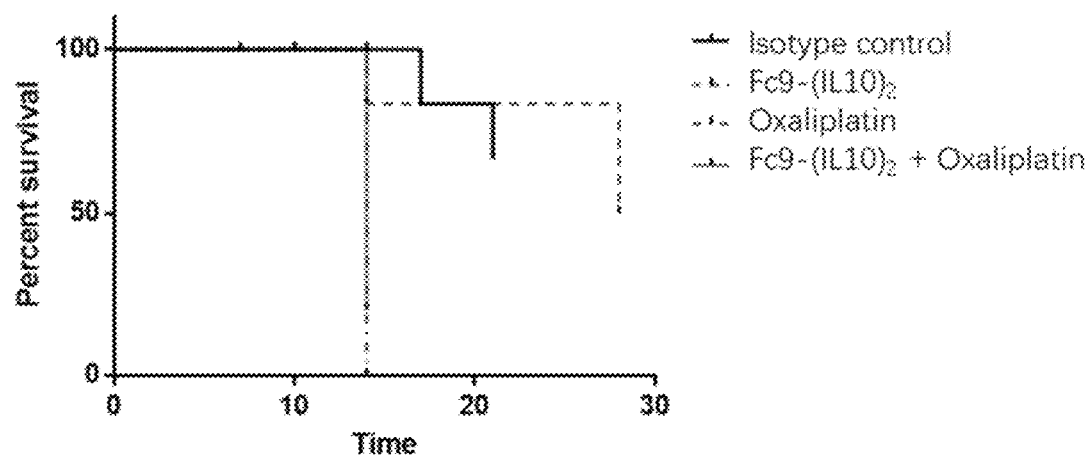

FIG. 7J shows the effects on survival rate for Fc9-(IL10)$_2$, oxaliplatin, and the combination of Fc9-(IL10)$_2$ with oxaliplatin.

For the above experiments, similar results were obtained for Tmab-(IL10)$_2$, 28H1-(IL10)$_2$, and (IL10-Fc)$_2$. In addition, it was found that the immunoconjugates of the present disclosure had (selective) synergistic effects when administered in combination with a variety of other chemotherapy drugs.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following embodiments define the scope of the invention and that methods and structures within the scope of these embodiments and their equivalents be covered thereby.

What is claimed is:

1. A composition comprising an immunoconjugate and a cytotoxic agent, wherein:
   said immunoconjugate comprises a first member and a second member different from said first member, wherein said first member comprises a first Fc subunit, and said second member comprises two interleukins fused to a second Fc subunit, and said first Fc subunit associates with said second Fc subunit to form a heterodimer;
   said two interleukins are fused to an amino-terminal amino acid of said second Fc subunit; wherein said two interleukins are two copies of IL10;
   wherein the amino acid sequence of a light chain comprised in the first member is SEQ ID NO: 37, and the amino acid sequence of a heavy chain comprised in the first member is SEQ ID NO: 39;
   wherein said cytotoxic agent comprises a radiation agent that emits X-ray radiation and/or electron beam radiation, said cytotoxic therapy comprises at least one dose of a radiation therapy at a dosage of Gy,
   or,
   wherein said cytotoxic agent is capable of inducing immunogenic cell death comprising oxaliplatin.

2. The composition according to claim 1, wherein said two copies of IL10 are fused to each other through a peptide linker to form an IL10 dimer, and the amino acid sequence of said peptide linker is SEQ ID NO: 49.

3. The composition according to claim 1, wherein said first Fc subunit and said second Fc subunit is an IgG Fc subunit.

4. The composition according to claim 1, wherein the amino acid sequence of the second member is SEQ ID NO: 50.

5. A method of treating cancer in a subject in need thereof, comprising administrating an immunoconjugate in combination with a cytotoxic therapy,
   wherein said immunoconjugate comprises a first member and a second member different from said first member, wherein said first member comprises a first Fc subunit, and said second member comprises two interleukins fused to a second Fc subunit, and said first Fc subunit associates with said second Fc subunit to form a heterodimer; said two interleukins are fused to an amino-terminal amino acid of said second Fc subunit; wherein said two interleukins are two copies of IL10;
   wherein the amino acid sequence of a light chain comprised in the first member is SEQ ID NO: 37, and the amino acid sequence of a heavy chain comprised in the first member is SEQ ID NO: 39; and the amino acid sequence of the second member is SEQ ID NO: 50;
   wherein said cytotoxic therapy comprises X-ray radiation and/or electron beam radiation, said cytotoxic therapy comprises at least one dose of a radiation therapy at a dosage of 10 Gy.

* * * * *